United States Patent
Deckelbaum et al.

(10) Patent No.: US 10,070,643 B2
(45) Date of Patent: Sep. 11, 2018

(54) REPERFUSION WITH OMEGA-3 GLYCERIDES PROMOTES DONOR ORGAN PROTECTION FOR TRANSPLANTATION

(71) Applicant: THE TRUSTEES OF COLUMBIA UNIVERSITY IN THE CITY OF NEW YORK, New York, NY (US)

(72) Inventors: Richard J. Deckelbaum, Hastings on Hudson, NY (US); Ravichandran Ramasamy, Ardsley, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 298 days.

(21) Appl. No.: 14/780,832

(22) PCT Filed: Mar. 28, 2014

(86) PCT No.: PCT/US2014/032279
§ 371 (c)(1),
(2) Date: Sep. 28, 2015

(87) PCT Pub. No.: WO2014/160989
PCT Pub. Date: Oct. 2, 2014

(65) Prior Publication Data
US 2016/0050909 A1    Feb. 25, 2016

Related U.S. Application Data

(60) Provisional application No. 61/806,391, filed on Mar. 28, 2013.

(51) Int. Cl.
*A01N 1/02* (2006.01)
*A61K 31/202* (2006.01)

(52) U.S. Cl.
CPC .......... *A01N 1/0226* (2013.01); *A61K 31/202* (2013.01)

(58) Field of Classification Search
CPC ........................ A01N 1/0226; A61K 31/202
See application file for complete search history.

(56) References Cited

U.S. PATENT DOCUMENTS 4,895,876 A    1/1990  Schweighardt et al.
5,089,268 A    2/1992  Katz
(Continued)

FOREIGN PATENT DOCUMENTS

EP    0033402    9/1983
EP    1408931    7/2002
(Continued)

OTHER PUBLICATIONS

Hospira, Inc., "Liposyn II Safflower Oil, Soybean Oil and Egg Phospholipids Injection, Emulsion", Jul. 12, 2012, pp. 1-19, Publisher: Hospira, Inc., Published in: http://dailymed.nlm.nih.gov/dailymed/drugInfo.cfm? setid=1c12b44c-f074-4a14-efad-4a6c743613cf.

(Continued)

*Primary Examiner* — Trevor Love
(74) *Attorney, Agent, or Firm* — Judith Evans; Beusse Wolter Sanks & Marie

(57) ABSTRACT

It has been discovered that isolated organs and tissues perfused/reperfused in perfusion buffer to which omega-3 glyceride oil had been added retain higher levels of function than if perfused/reperfused without the omega-3 glycerides. Isolated hearts reperfused ex vivo after induced ischemia in n-3 triglyceride perfusion emulsion maintained a normal heart rate and normal LVDP and showed a dramatically reduced frequency of arrhythmias compared to control hearts. Further, test hearts reperfused with n-3 oil triglycer- (Continued)

ide emulsion showed a decrease in creatine kinase and upregulation of certain beneficial proteins including the anti-apoptotic gene marker Bcl-2.

8 Claims, 24 Drawing Sheets

(56) References Cited

U.S. PATENT DOCUMENTS

| | | | |
|---|---|---|---|
| 5,160,759 | A | 11/1992 | Nomura et al. |
| 5,214,062 | A | 5/1993 | Mark et al. |
| 5,700,837 | A | 12/1997 | Trimbo |
| 6,020,020 | A | 2/2000 | Cain et al. |
| 6,306,908 | B1 | 10/2001 | Carlson et al. |
| 6,448,292 | B2 | 9/2002 | Koike et al. |
| 6,974,592 | B2 | 12/2005 | Yan |
| 7,935,729 | B2 | 5/2011 | Harbige et al. |
| 8,293,791 | B2 | 10/2012 | McCullough et al. |
| 8,410,181 | B2 | 4/2013 | Deckelbaum et al. |
| 8,536,232 | B2 | 9/2013 | Deckelbaum et al. |
| 2002/0160537 | A1 | 10/2002 | Kleinfeld |
| 2003/0144356 | A1 | 7/2003 | Goodale |
| 2003/0149118 | A1 | 8/2003 | Akashe et al. |
| 2003/0175403 | A1 | 9/2003 | Gurin |
| 2004/0247693 | A1 | 12/2004 | Carpentier et al. |
| 2007/0281993 | A1 | 12/2007 | Rozen et al. |
| 2010/0093856 | A1 | 4/2010 | Deckelbaum et al. |
| 2011/0206741 | A1 | 8/2011 | Lee et al. |
| 2012/0040934 | A1 | 2/2012 | Driscoll |
| 2012/0315618 | A1 | 6/2012 | Kravitz et al. |

FOREIGN PATENT DOCUMENTS

| | | |
|---|---|---|
| EP | 1279400 A1 | 1/2003 |
| GB | 2388026 | 11/2003 |
| WO | 198805261 | 7/1988 |
| WO | 1999026620 A1 | 6/1999 |
| WO | 1999056727 | 11/1999 |
| WO | 2004028470 A2 | 4/2004 |
| WO | 2005013908 A1 | 2/2005 |
| WO | 2007059431 A1 | 5/2007 |
| WO | 2008036353 A2 | 3/2008 |
| WO | 2009014452 A1 | 1/2009 |
| WO | 2010104575 A2 | 9/2010 |
| WO | 2011133841 A2 | 10/2011 |

OTHER PUBLICATIONS

Taha, "Buffers for the Physiological pH Range: Acidic Dissociation Constants of Zwitterionic Compounds in Various Hydroorganic Media", 2005, Page(s) Abstract, Publisher: Annali di Chimica, Published in: http://onlinelibrary.wiley.com/doi/10.1002/adic.200590001/abstract.

USPTO RO, "ISA/WO Written Opinion and Search Report PCT/US14/32279," dated Sep. 12, 2014.

IPO/CN: Second Office Action, Chinese Patent Application No. 2014800311494, dated Aug. 16, 2017, 6 pages.

Bazan, N., "Neuroprotectin D1 (NPD1): a DHA-derived mediator that protects brain and retina against cell injury-induced oxidative stress", Brain Pathol., Apr. 1, 2005, pp. 159-166, vol. 15, No. 2, Published in: https://www.ncbi.nlm.nih.gov/pubmed/15912889.

Bazan, N.G., "Omega-3 fatty acids, pro-inflammatory signaling and neuroprotection", Current Opinion in Nutrition and Metabolic Care, Mar. 1, 2007, pp. 136-141, vol. 10, No. 2, Published in: doi: 10.1097/MCO.0b013e32802b7030.

Billman, G., and Leaf, A., "The Effects of Omega-3 Fatty Acids on Ventricular Fibrillation Induced by Myocardial Ischemia,", Proceedings from the Scientific Conference on Omega-3 Fatty Acids in Nutrition, Vascular Biology, 1994, pp. 159-165, Publisher: American Heart Association, Published in: Houston, TX.

Billman, G., et al., "Prevention of ischemia-induced ventricular fibrillation by omega-3 fatty acids", Proc. Natl. Acad. Sci. USA, 1994, pp. 4427-4444, vol. 91, Publisher: National Academy of Sciences USA, Published in: http://www.pnas.org/content/91/10/4427.abstract?sid=65fe2449-68d8-4f17-862a-beea311dfbdf.

Cao, D., et al., "Chronic Administration of Ethyl Docosahexaenoate Decreases Mortality and Cerebral Edema in Ischemic Gerbils", Life Sciences, 2005, pp. 74-81, vol. 78, No. 1, Publisher: Elsevier, Published in: http://www.sciencedirect.com/science/article/pii/S0024320505009082.

ChemSpider, "Docosahexaenoic acid", pp. 1-2, Publisher Royal Society of Chemistry, Published in: http://www.chemspider.com/Chemical-Structure.393183.html (accessed 17:30, Jan. 6, 2016).

ChemSpider, "Eicosapentanoic acid", pp. 1-4, Publisher: Royal Society of Chemistry, Published in: http://www.chemspider.com/Chemical-Structure.393682.html.

Dornbierer, M., et al., "Early reperfusion hemodynamics predict recovery in rat hearts: a potential approach towards evaluating cardiac grafts from non-heart-beating donor", PLoS One, Aug. 21, 2012, pp. 1-9, vol. 7, No. 8, Published in: doi: 10.1371/journal.pone.0043642.

EPO, Extended Search Report, European Patent Application No. 14754815.0, dated Jun. 22, 2016, pp. 1-8.

Fiaccadori, E., et al., "Hemodynamic, Respiratory, and Metabolic Effects of Medium-Chain Triglyceride-enriched Lipid Emulsions Following Valvular Heart Surgery", Chest, 1994, pp. 1660-1667, vol. 106, No. 6, Publisher: American College of Chest Physicians, Published in: http://journal.publications.chestnet.org/article.aspx?articleid=1068168.

Healthnotes, "Fish Oil and Cod Liver Oil (EPA & DHA)", Wayback Machine, Oct. 25, 2004, pp. 1-6, Publisher: Healthnotes Inc., Published in: http://www.puritan.com/vf/healthnotes/HN_Live/Supp/Fish_Oil_htm.

IPO/CN: First Office Action, Chinese Patent Application No: 2014800311494, dated Oct. 9, 2016, 12 pages.

ISA/EPO, International Search Report and Written Opinion, International Patent Application No. PCTUS2006/060777, dated Apr. 13, 2007, pp. 1-11.

ISA/US: International Search Report and Written Opinion, International Patent Application No. US14/17523, dated Mar. 16, 2014, pp. 1-10.

Jung, U.J., et al., "Fatty acids regulate endothelial lipase and inflammatory markers in macrophages and in mouse aorta: a role for PPAR", Atheriosclerosis, Thrombosis, and Vascular Biology, Nov. 14, 2012, pp. 2929-2937, vol. 32, No. 12, Published in: doi.org/10.1161/ATVBAHA.112.300188.

Lim, S.N., et al., "Improved outcome after spinal cord compression injury in mice treated with docosahexaenoic acid", Exp Neurol, Jan. 1, 2013, pp. 13-27, vol. 239, Published in: http://www.sciencedirect.com/science/article/pii/S0014488612003779.

Mayurasadorn, K., et al., "Docosahexaenoic acid: brain accretion and roles in neuroprotection after brain hypoxia and ischemia", Current Opinion in Clinical Nutrition and Metabolic Care, Mar. 1, 2011, pp. 158-167, vol. 14, No. 2, Published in: doi: 10.1097/MCO.0b013e328342cba5.

Mooe, T., et al., "Ischemic Stroke after Acute Myocardial Infarction: A Population-Based Study", Stroke, 1997, pp. 762-767, vol. 28, Publisher: American Heart Association, Published in: stroke.ahajournals.org.

Murray-Taylor, F.M. et al., "n-3, but not n-6 lipid particle uptake requires cell surface anchoring", Biochemical and Biophysical Research Communications, Feb. 5, 2010, pp. 135-139, vol. 392, No. 2, Published in: http://www.sciencedirect.com/science/article/pii/S0006291X10000057.

Strokin, M., et al., "Neuroprotection of rat hippocampal slices exposed to oxygen-glucose deprivation by enrichment with docosahexaenoic acid by inhibition of hydrolysis of docosahexaenoic acid-containing phospholipids . . . ", Neuroscience, 2006, pp. 547-553, vol. 140, No. 2, Publisher: Elsevier, Published in: http://www.sciencedirect.com/science/article/pii/S0306452206002235.

Williams, J., et al., "N-3 Fatty Acid Rich Triglyceride Emulsions Are Neuroprotective after Cerebral Hypoxic-Ischemic Injury in Neonatal Mice", PLoS One, Feb. 20, 2013, pp. 1-11, vol. 8, No. 2,

(56) References Cited

OTHER PUBLICATIONS

Publisher: Public Library of Science, Published in: http://dx.doi.org/10.1371/journal.pone.0056233.
Arisue, A., et al., "Effect of an omega-3 lipid emulsion in reducing oxidative stress in a rat model of intestinal ischemia-reperfusion injury," Pediatr. Surg. Int., 2012, pp. 913-918, vol. 28.
EPO, "EP Extended Search Report Application No. 14775254.7," dated Aug. 31, 2016, 10 pages.
Callaghan, M. J., "Handbook of Modern Emergency Medicine", 1990, pp. 1-6, Publisher: Chengdu Press, Published in: China (translation of first page only).
IPO/CN: First Office Action, Chinese Patent Application No. 2014800224481, dated Nov. 22, 2016, pp. 1-21.

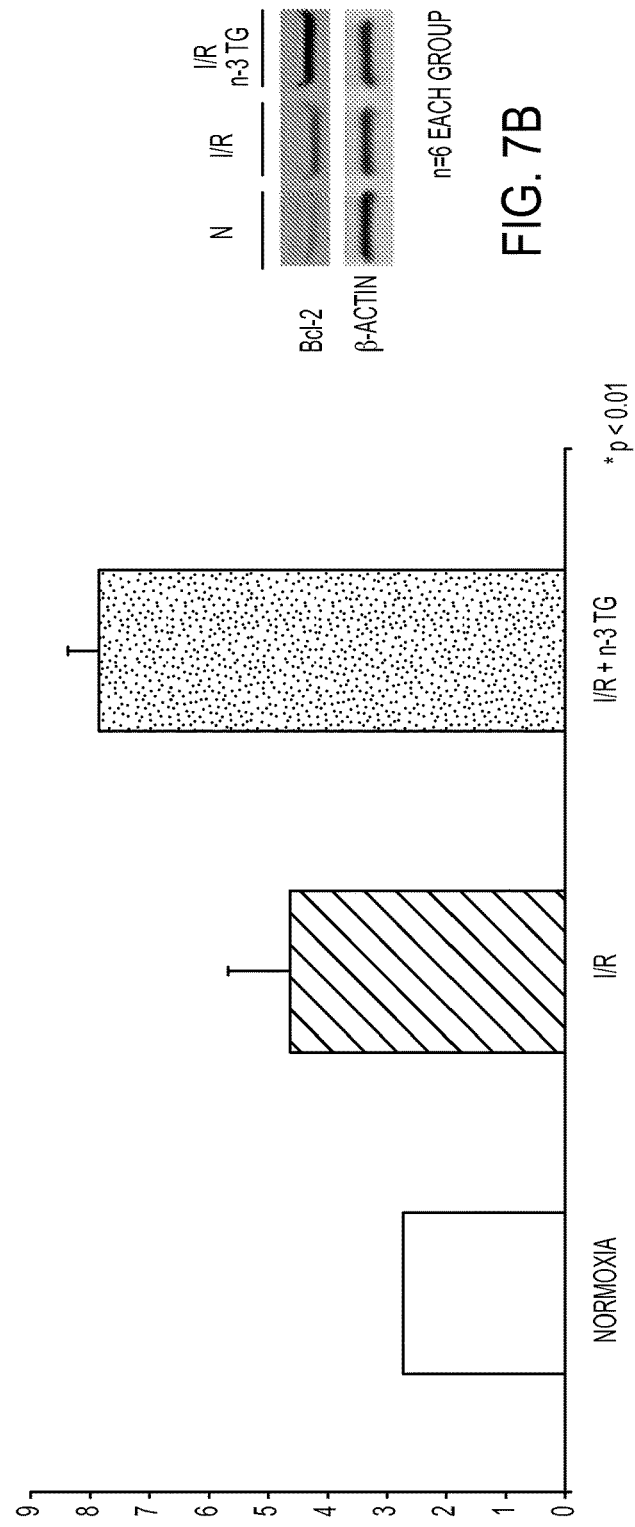

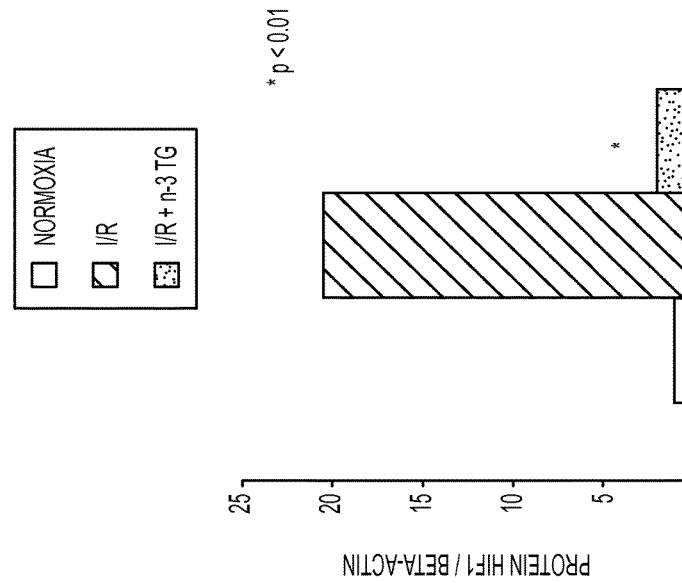
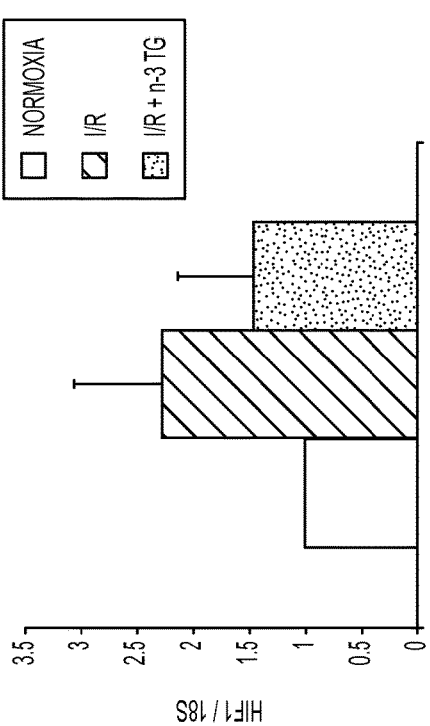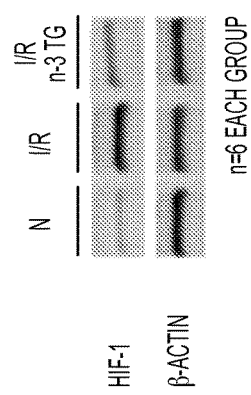
FIG. 8A
FIG. 8B
FIG. 8C

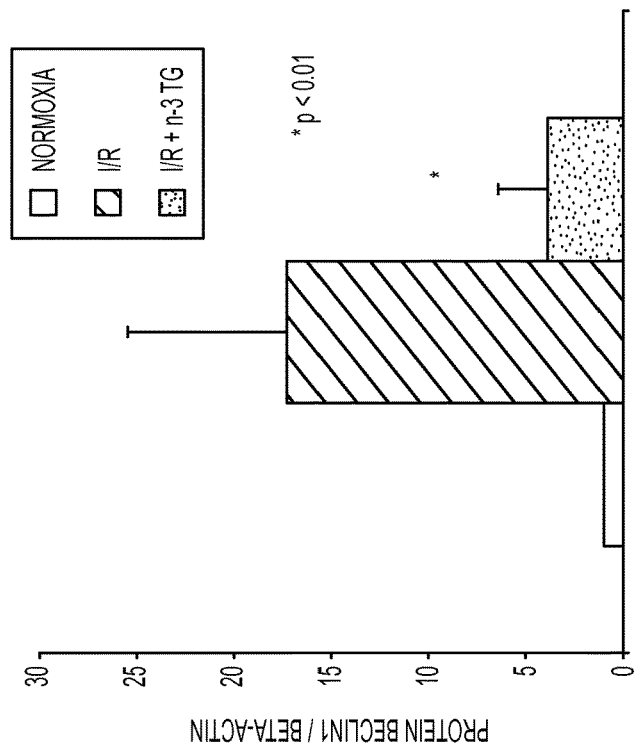
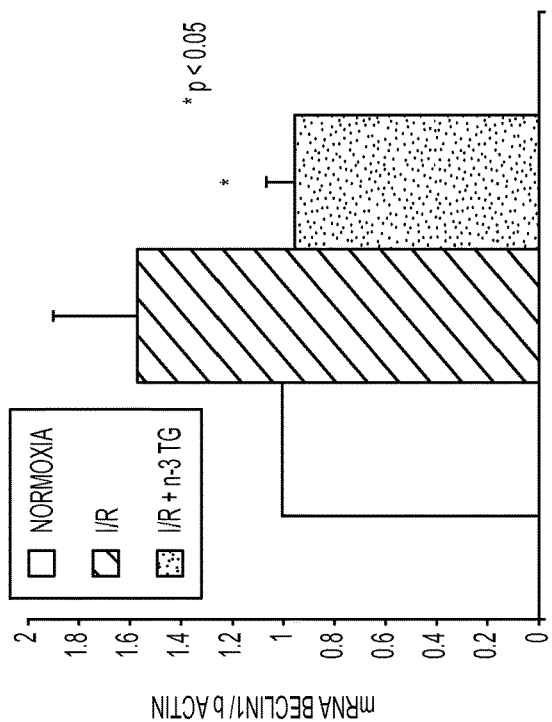
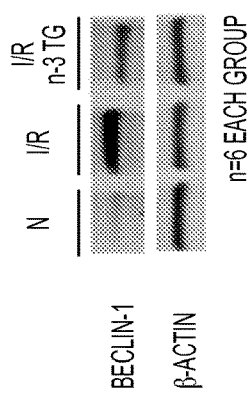
FIG. 9A
FIG. 9B
FIG. 9C

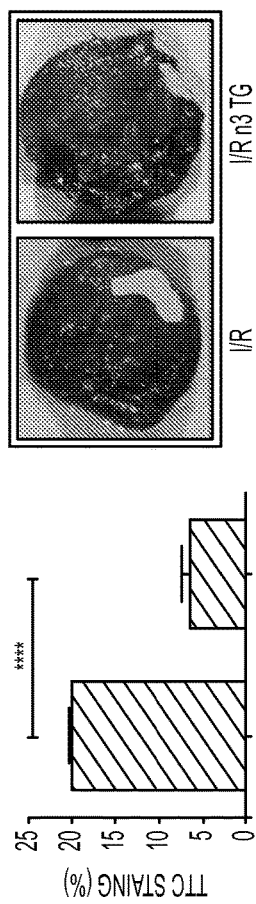
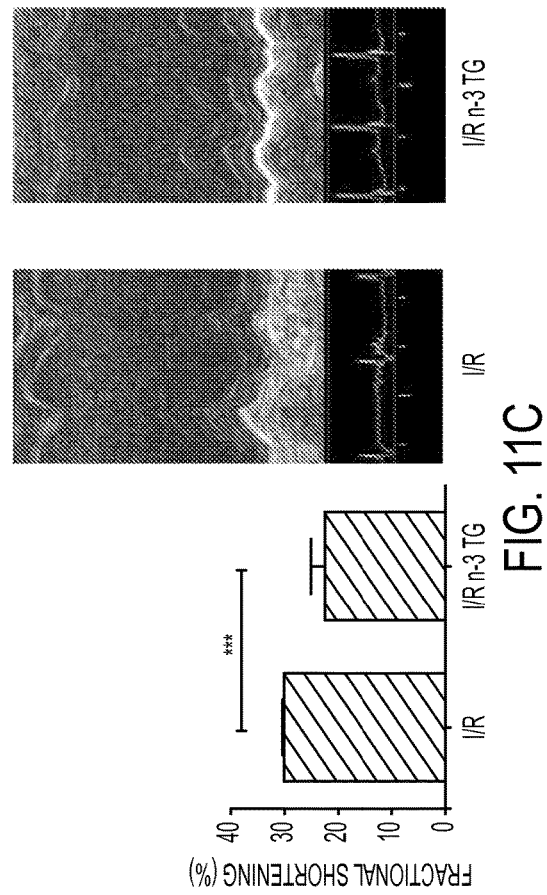
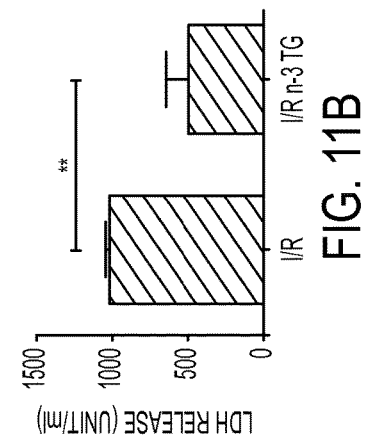
FIG. 11A
FIG. 11B
FIG. 11C

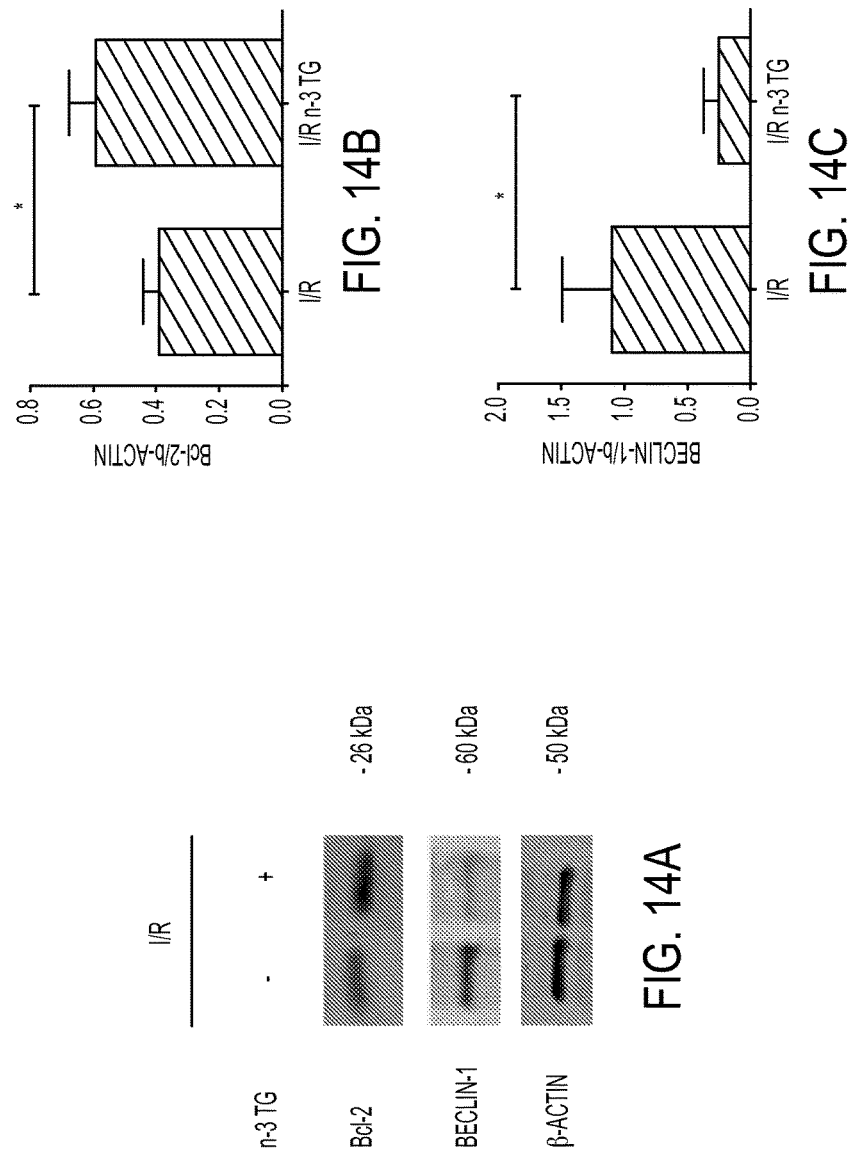

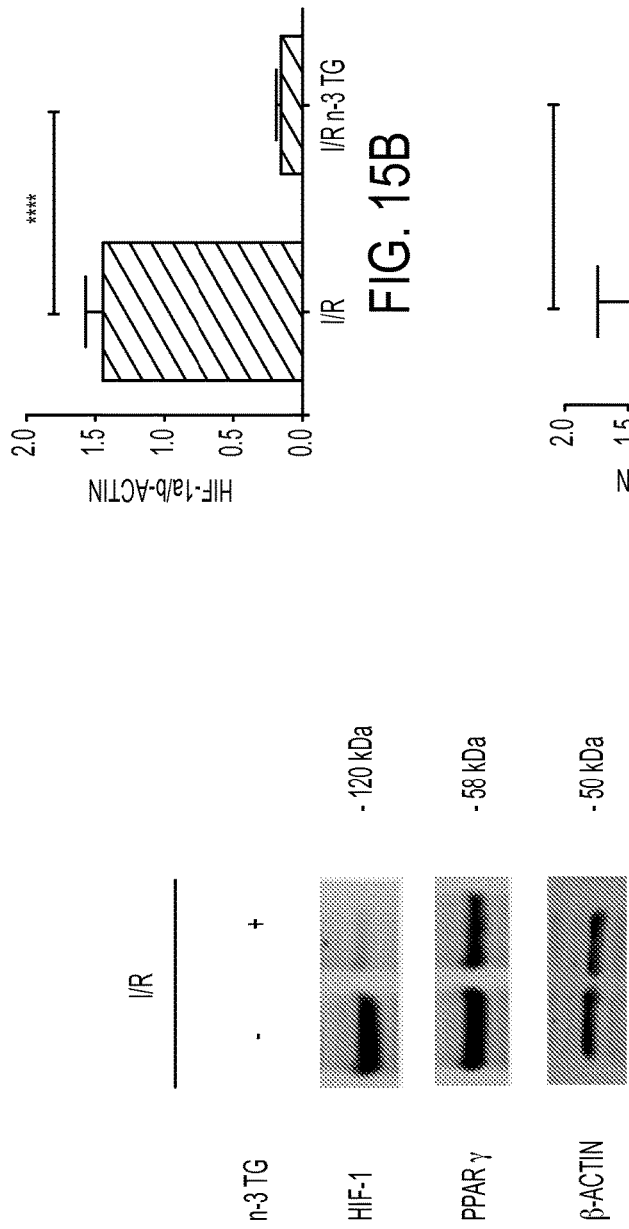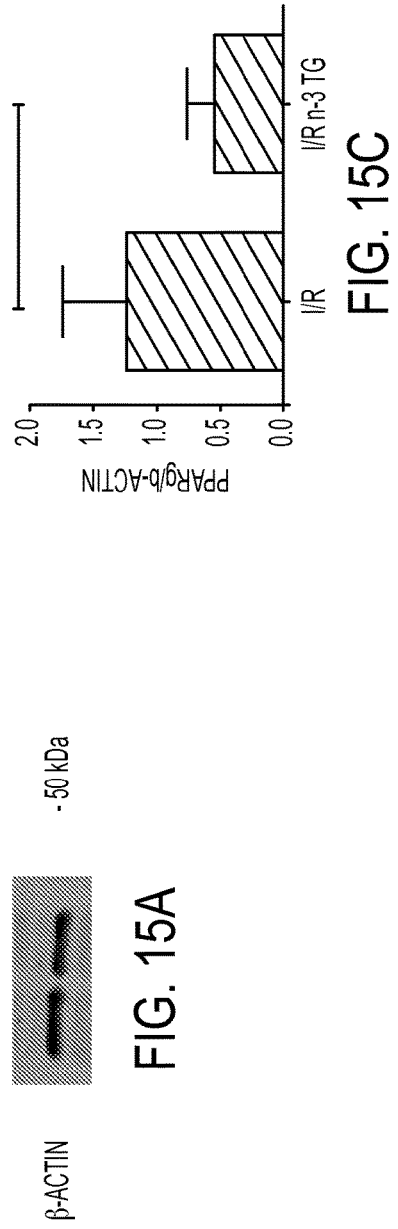

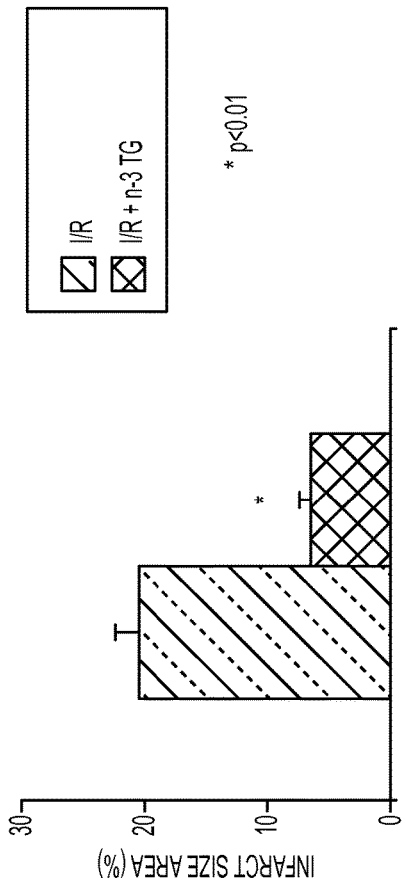
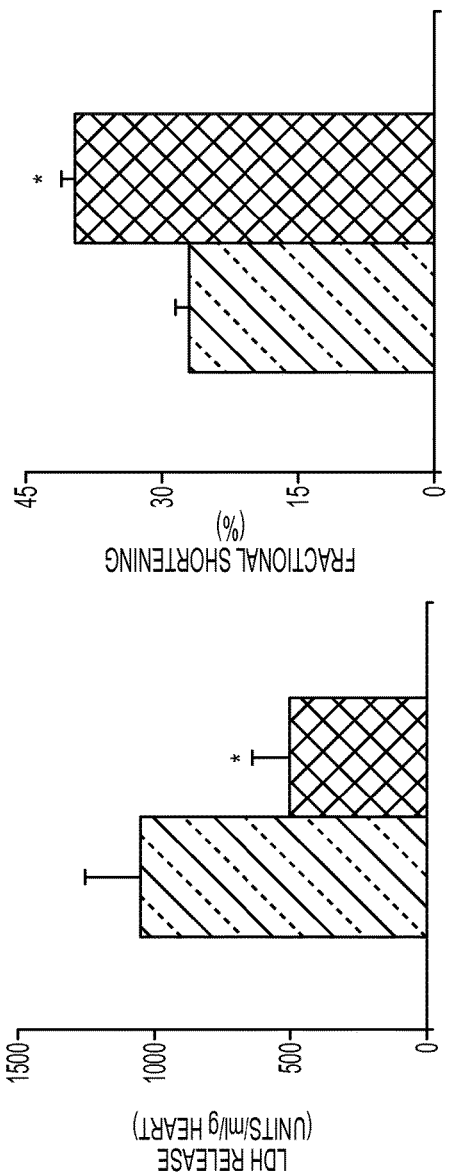
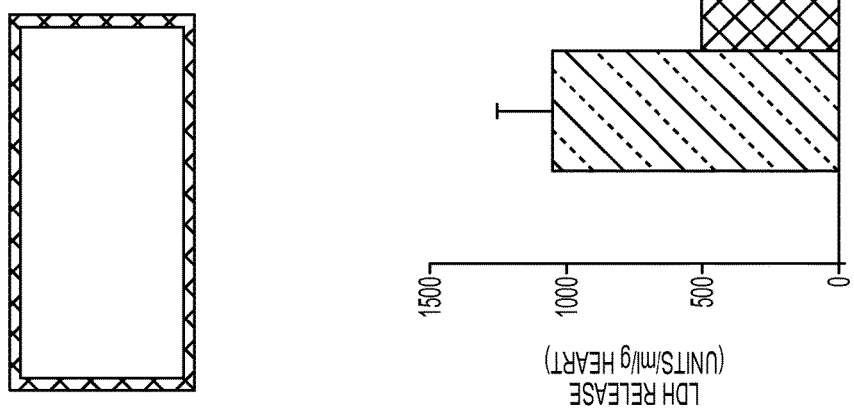
FIG. 23A
FIG. 23B
FIG. 23C

REPERFUSION WITH OMEGA-3 GLYCERIDES PROMOTES DONOR ORGAN PROTECTION FOR TRANSPLANTATION

CROSS-REFERENCE TO RELATED APPLICATIONS

This application is a 371 national stage application of PCT Application No. PCT/US14/032279, filed Mar. 28, 2014, and claims the benefit of U.S. Provisional Application No. 61/806,391, filed on Mar. 28, 2013; the entire contents of which are hereby incorporated by reference as if fully set forth herein.

STATEMENT OF GOVERNMENTAL INTEREST

This invention was made with government support under grant HL040404 awarded by the National Institutes of Health. The Government has certain rights in this invention.

BACKGROUND

The present invention provides preservation solutions useful for storing organs while awaiting implantation which extend the vitality of the organ and reduce damage to organ cells. The present invention also provides method for preserving organs which extend the maximum life of the organ before and during transplantation.

A great deal of research progress has been made over the years in understanding cellular mechanisms, as well as developing new transplantation techniques, for keeping organs viable not only during storage but also after reperfusion of these organs (e.g., minimization of ischemia/reperfusion injury). As a result, organ transplantation has become an established and effective technique. A significant factor limiting clinical application of organ transplantation is decrease in viability of the organ after removal from the donor.

Generally, the two most frequently used methods for preserving organs after removal from the donor are simple hypothermic storage and continuous pulsatile perfusion. With simple hypothermic storage, the organ is removed from the donor and cooled rapidly. This is usually achieved by a combination of cooling and short periods of perfusion to drop the organ temperature as quickly as possible to a temperature between 0° C. and 4° C., where it may be held for up to about six hours. While cold storage enables organs to be transplanted, the time during which the organ is viable is short. Cold storage decreases the rate at which intracellular enzymes, essential cellular components necessary for organ viability, degrade but does not stop metabolism entirely.

The second method of organ preservation which has undergone extensive investigation, continuous pulsatile perfusion, utilizes the following elements: (1) pulsatile flow, (2) hypothermia, (3) membrane oxygenation, and (4) a perfusate containing both albumin and lipids. Although being more technically complex and costly, continuous pulsatile perfusion provides significantly longer viability of the organ when compared to simple hypothermia.

Preserving organs at between 0° C. and 4° C. can result in damage to the organ during storage and upon reperfusion with a warm reperfusion solution. Injury to the organ occurs through damage to epithelial, endothelial and parenchymal cells. Although some of the solutions of the prior art have been useful to extend the storage time of donor organs and lessen injury to the organ upon reperfusion, cell injury still does occur frequently. It is desirable to extend the viable organ life and improve the quality of the transplanted organ. For example, using preservation solutions of the prior art, kidneys that have been in cold storage beyond 48 hours frequently cannot be used and must be discarded. Extending organ viability allows sufficient time for compatibility testing of the donor and recipient, and increased organ availability. It is also desirable to minimize damage to the organ upon reperfusion. Ischemia-reperfusion injury to transplanted organs preserved in solutions of the prior art commonly results in delayed graft function, and predisposes the graft to acute and chronic rejection.

There remains a need in the art for improved methods and compositions for conservation and preparation of organs and tissues for transplant.

SUMMARY

Certain embodiments are directed to omega-3 oil in water glyceride emulsions for perfusion of an organ or tissue ex vivo, wherein the emulsion comprises (a) a perfusion buffer suitable for organ or tissue preservation and transplantation, (b) less than 7% (preferably less than 2%) of an omega-3 oil by weight in grams per 100 ml of perfusion buffer, wherein the omega-3 oil (i) comprises from about 10% to about 99% omega-3 diglyceride, omega-3 triglyceride or combinations thereof by weight per total weight of the omega-3 oil, and at least about 20% to about 99% of the total acyl groups of the omega-3 diglycerides and triglycerides comprise EPA or DHA, and (ii) comprises less than 10% omega-6 fatty acids by weight per total weight of the omega-3 oil. The emulsion itself has (c) less than 10% omega-6 oil, and (d) the mean diameter of lipid droplets in the emulsion is from about 100 nm to less than about 5 microns, preferably from 100 nm to 500 nm.

Other embodiments are directed to methods of preserving isolated organs and tissues, comprising (a) providing the omega-3 oil in water emulsion of the invention, and (b) contacting (including perfusing, storing, and reperfusing) the isolated organ or tissue ex vivo with the emulsion for a duration of time at a temperature that preserves the organ or tissue until it is transplanted into a recipient or is otherwise used. Organs and tissues for use in the present methods perfusing, storing, and reperfusing) include liver, lung, skin, heart, heart valve, bone, bone marrow, blood vessels, lymph nodes, intestine, pancreas, teeth, gingiva, small bowel, colon, appendages (fingers, toes, arms, legs), scalp, epithelium or blood for transfusion.

Other embodiments are directed to methods for preserving or preparing an organ or tissue for transplantation or other use, comprising contacting (including perfusing, storing, and reperfusing) the organ or tissue ex vivo with the omega-3 emulsion of the invention for a duration of time at a temperature that preserves the organ or tissue until it is transplanted into a recipient or is otherwise used. Storage and perfusion/reperfusion temperatures can vary widely, typically from about 0° C. to about 37° C. In some embodiments the organ or tissue is contacted with the omega-3 glyceride perfusion emulsions of the invention by static cold storage or low temperature continuous perfusion/reperfusion, at a temperature within in a range of about −5° C. to about 10° C.

In some embodiments n-3 glyceride emulsions are added to storage solutions, and certain embodiments are directed to storage solutions comprising the emulsions. Omega-3 emulsions may also be added to matrices that may be used to preserve some tissues before transplant such as skin, and some embodiments are directed to these matrices comprising n-3 glyceride emulsions. Any perfusion buffer, storage solution or matrix used for preserving, storing, perfusing organs or tissues can be used in the embodiments, typically but not necessarily always at a physiologic pH.

BRIEF DESCRIPTION OF THE DRAWINGS

The present invention is illustrated by way of example, and not by way of limitation, in the following figures.

FIG. 7A-7B are graphs that illustrate Bcl-2, an anti-apoptotic marker, mildly increases after ischemia in controls, but n-3 TG added to the reperfusion buffer increased it much more. FIG. 7A is a bar graph that shows mRNA gene expression and FIG. 7B is a photograph that shows the actual protein measured by western blot.

FIG. 8A-8C are bar graphs that illustrate HIF1, associated with decreasing apoptosis and decreasing cell death, was down-regulated after reperfusion in n-3 TG emulsion as is shown both by gene expression in bar graphs (FIGS. 8A-8B) and by western blot analysis for HIF1 protein as shown in FIG. 8C (bottom left for western gel, bottom right for protein).

FIG. 9A-9C show that the autophagic marker Beclin-1 was decreased in ex vivo hearts after ischemia when n-3 TG was added to the reperfusion buffer. FIG. 9A is a bar graph that shows the level of Beclin-2 mRNA expression after H/I in control hearts and hearts reperfused after H/I with n-3 glyceride perfusion emulsion. FIG. 9B is a photograph that shows western blot analysis for Beclin-1 protein (bottom left for western gel, bottom right for protein). FIG. 9C is a bar graph that shows the level of Beclin-1 protein.

FIG. 10B is a photograph showing western blot analysis for PPAR gamma protein.

FIG. 11A-11C show the effects on hearts in vivo of acute n-3 TG emulsions administered after H/I in the in vivo left anterior descending coronary artery (LAD) occlusion model. Mice were subjected to LAD occlusion for 30 min followed by reperfusion period (48 h) in vivo with or without acute n-3 TG emulsion injection. FIG. 11A is a bar graph that shows that hearts isolated at 48 h of reperfusion and subjected to TTC staining n=3 mice/group. *P<0.05. FIG. 11B is a bar graph that shows total plasma LDH levels at 48 hrs. n=3 mice/group. *P<0.05. FIG. 11C is a bar graph that quantifies fractional shortening percentage detected by echocardiogram just before sacrifice at 48 hrs. n=3 mice/group. *P<0.05. Data represent means±SD.

FIG. 12A is a bar graph that shows myocardial ischemic injury by measuring left ventricular developed pressure (LVDP) recovery in hearts subjected to ischemia/reperfusion treated with or without n-3 TG emulsion during reperfusion. *P<0.05. FIG. 12B is a bar graph that shows the level of LDH release during reperfusion time. *P<0.05. Four hearts per group were studied. Data represent means±SD.

FIG. 13A is a photograph that shows western blot analysis of p-AKT and p-GSK3β in hearts subjected to ischemia/reperfusion injury with or without n-3 TG emulsion treatment. FIG. 13B is a bar graph that shows that p-AKT was increased by n-3 TG treatment. FIG. 13C is a bar graph that shows that GSK3b were increased by n-3 TG treatment. *P<0.05. Three hearts per group were studied. Data represent means±SD.

FIGS. 14A-14C illustrate markers for apoptosis and autophagy. FIG. 14A is a photograph that shows western blot analysis of Bcl-2 and Beclin-1 in hearts subjected to I/R injury with or without n-3 TG emulsion administered during reperfusion time. FIG. 14B is a bar graph that shows increased: Bcl-2 and FIG. 14C is a bar graph that shows decreased Beclin-1 protein expression in n-3 TG treated hearts. *P<0.05. Three hearts per group were studied. Data represent means±SD.

FIGS. 15A-15C illustrate examples of transcription factors expression. FIG. 15A is a photograph that shows western blot analysis of PPAR-γ and HIF-1a in hearts subjected to I/R injury with or without n-3 TG emulsion administered during reperfusion time. FIG. 15B is a bar graph that shows HIF-1a. FIG. 15C is a bar graph that shows PPAR-γ expression which were decreased by n-3 TG administration. *P<0.05. Three hearts per group were studied. Data represent means±SD.

FIG. 16A is a bar graph that shows LDH release (fold change) compared to I/R control (reported in FIG. 12A-12B). p-AKT inhibitor (10 μM LY-294002) increased LDH. Treatment with GSK3β inhibitor (3 μM SB216763) significantly inhibited LDH release. P<0.05. Data represent means±SD. FIG. 16B is a bar graph that illustrates LDH release (fold change) compared to n-3 TG I/R (reported in FIG. 12A-12B). p-AKT inhibitor abolished the beneficial effect of n-3 TG. GSK3β inhibitor (3 μM SB216763). Rosiglitazone treatment entirely reversed the protective effect of n-3 TG. P<0.05. Six hearts per group were studied. Data represent means±SD. * P<0.05 I/R vs treatments.

FIG. 18A is a micrograph that illustrates TTC-stained coronal sections of representative mouse brains from saline treated, n-3 TG treated and n-6 TG treated. The top panel shows images of coronal mouse brain sliced and stained with TTC (grey for living tissue and white for the infarcted tissue), and the lower panel shows the infarcted areas traced in black for quantification. FIG. 18B is a bar graph that illustrates percent of cerebral infarct volume from pre-H/I mice treated with n-3 TG emulsion (n=28) or n-6 TG emulsion (n=10) or saline control (n=27). FIG. 18C is a bar graph that illustrates percent of cerebral infarct volume after H/I in the post-H/I treatment protocol in mice treated with n-3 TG emulsion (n=18) or saline control (n=18). Each bar represents the mean±SEM of 5-7 independent experiments.

FIG. 19A illustrates mice subjected to 15 min ischemia followed by 24-hr reperfusion and received 2 i.p. administrations (immediately after ischemia and 1 hr of reperfusion) at 2 doses (0.1 g n-3 TG/kg and 0.375 g n-3 TG/kg). Each bar represents the mean±SEM of 5-7 independent experiments performed using the same H/I model. FIG. 19B are micrographs that illustrate TTC-stained coronal sections of representative mouse brains from saline treated, 0.1 g Tri-DHA, 0.375 g Tri-DHA, 0.1 g Tri-EPA and 0.375 g Tri-EPA. * p<0.05 compared to other groups except 0.1 g Tri-DHA/kg. ** p<0.05 compared to other groups except 0.375 g Tri-DHA/kg and 0.375 g Tri-EPA/kg.

FIG. 23A-23C are bar graphs that illustrate the reduction of acute MI in vivo after administration of n-3 TG. FIG. 23A is a bar graph that illustrates the reduction of infarct size area (%) for (left) control and (right) after administration of n-3 TG in the mouse heart after H/I injury. FIG. 23B is a bar graph that illustrates a decrease in LDH release which is a marker for heart cell damage for (left) control and (right) after administration of n-3 TG. FIG. 23C is a bar graph that illustrates n-3 TG maintenance of heart function via fractional shortening (%) for (left) control and (right) after administration of n-3 TG. Each bar represents the mean±SEM. * p<0.01.

Figure 1:
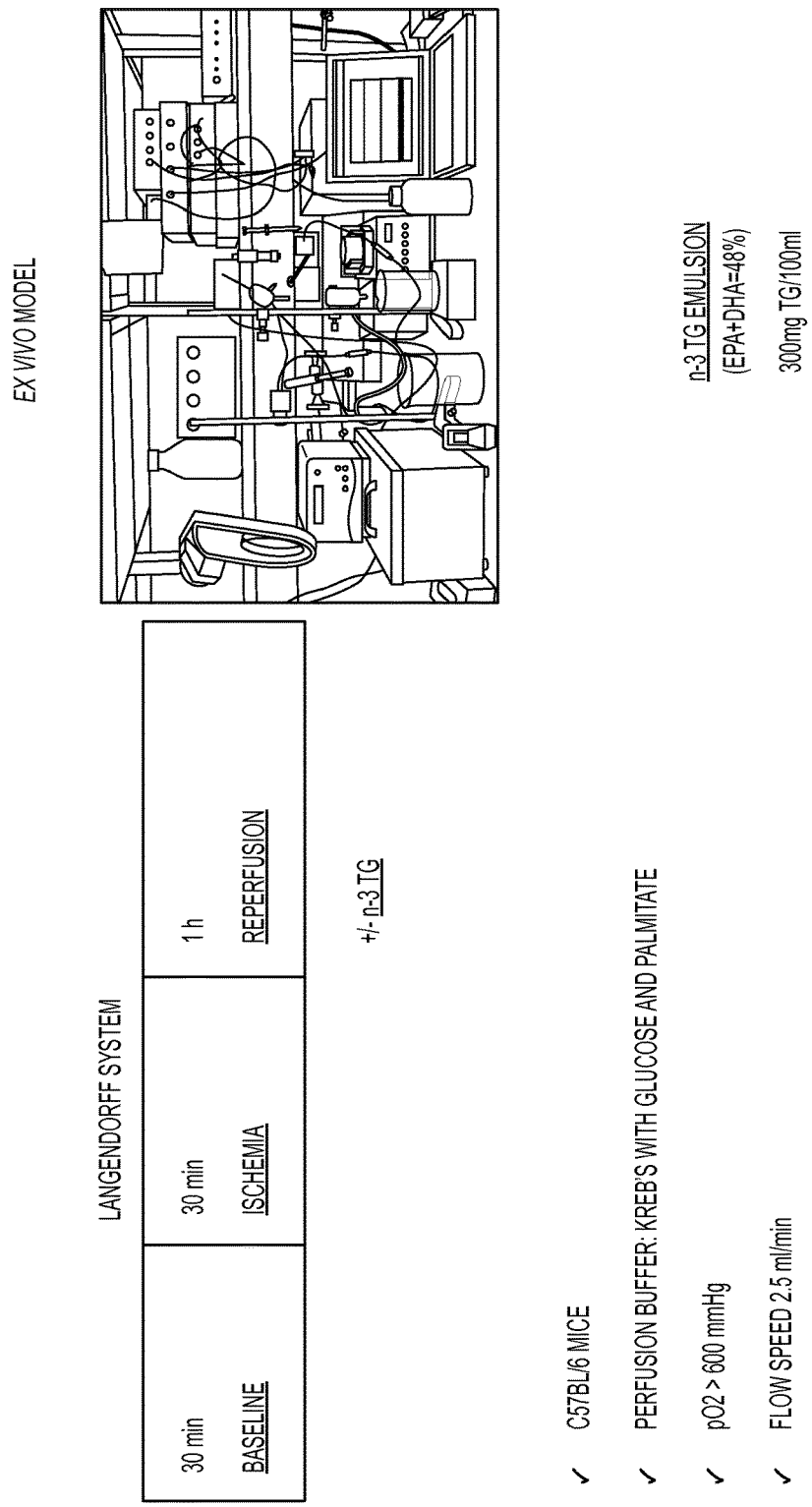
FIG. 1 is an illustration that shows the ex vivo Langendorff system (equipment and apparatus) used to study isolated C57BL/6 mouse hearts perfused immediately after isolation with a perfusion buffer containing KREBS solution with glucose. After a 30 min. period of ischemia, the perfused hearts were then reperfused with the same perfusion buffer with (test reperfusion emulsion) or without (control reperfusion buffer) an omega-3 (n-3) triglyceride (TG). In the example, the amount (concentration) of n-3 TG in the test reperfusion buffer was 300 mg n-3 TG/100 ml (final concentration of 0.3%) and 48% of the n-3 TG fatty acids (FA) were EPA and DHA.
Figure 2:
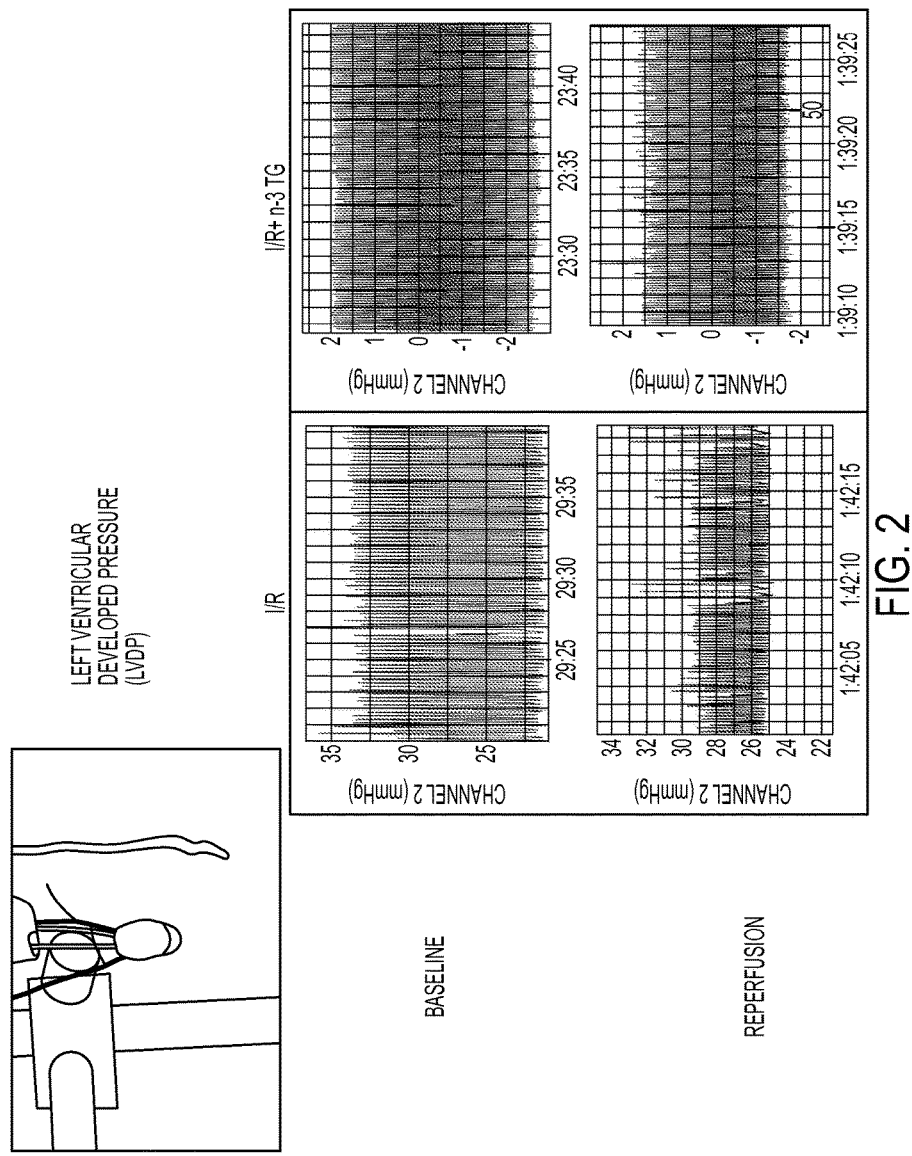
FIG. 2 is an illustration that includes graphs that show the effects of reperfusion with the test n-3 TG emulsion on left ventricular developed pressure (LVDP) after ischemia.

Before the present embodiments of the invention are described, it is to be understood that the inventions are not limited to the particular processes, compositions, or methodologies described, as these may vary. The terminology used in the description is for the purpose of describing the particular versions or embodiments only, and is not intended to limit the scope of the present invention. Unless otherwise defined, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein, are incorporated by reference in their entirety. Nothing herein is to be construed as an admission that the invention is not entitled to antedate such disclosure by virtue of prior invention.

DETAILED DESCRIPTION

In the following description, for the purposes of explanation, numerous specific details are set forth in order to provide a thorough understanding of the present invention. It will be apparent, however, to one skilled in the art that the present invention may be practiced without these specific details.

1. Definitions

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N. (2000).

As used herein "omega-3 di- or triglyceride oil" means an omega-3 oil comprising di- or triglycerides or combinations thereof, that have less than 10% omega-6 oil, preferably less than 5% omega-6 oil. As used herein, "omega-3 oils" means any omega-3 fatty acid, including free omega-3 fatty acids and omega-3 triglycerides, diglycerides and monoglycerides.

As used herein "omega-3 (n-3) oil-in-water perfusion emulsions" and "n-3 glyceride perfusion emulsions" are used interchangeably to mean n-3-containing emulsions for use as perfusion buffers for storing, perfusing, reperfusing or otherwise contacting an isolated organ or tissue, for example one intended for transplantation. The n-3 glyceride perfusion emulsions of the invention have less than 7% of an omega-3 oil and less than 10% omega-6 oil by weight in grams per 100 ml of buffer. The omega-3 oil in the emulsion comprises at least 20% omega-3 triglyceride (n-3 TG), omega-3 diglyceride (n-3 DG) or combinations thereof by weight per total weight of the omega-3 oil; less than about 10% omega-6 (n-6) fatty acids; and at least about 20% to about 100% of the total acyl groups of the omega-3 of the diglycerides or triglycerides consist of EPA and/or DHA.

As used herein, "omega-3 fatty acid" means a polyunsaturated fatty acid wherein one of the carbon-carbon double bonds is between the third and fourth carbon atoms from the distal end of the hydrocarbon side chain of the fatty acid. Examples of "omega-3 fatty acid" include a-linolenic acid (18:3n-3; α-ALA; $\Delta^{3,6,9}$), eicosapentaenoic acid (20:5n-3; EPA; $\Delta^{5,8,11,14,17}$), docosahexaenoic acid (22:6n-3; DHA) and docosapentaenoic acid (22:5n-3; DPA; $\Delta^{7,10,13,16,19}$), wherein EPA and DHA are most preferred. Omega-3 fatty acids having at least 20 carbon atoms are herein called "long chain omega-3 fatty acids."

As used herein, "omega-3 triglyceride" or "omega-3 diglyceride" or "omega-3 monoglyceride" refers to a triglyceride or a diglyceride or monoglyceride, respectively, comprising at least one omega-3 fatty acid esterified with a glycerol moiety. As used herein, the term "omega-3 tri/diglyceride" means that omega-3 fatty acid comprises an omega-3 triglyceride and/or a diglyceride or any combination thereof.

As used herein, the amount of omega-3 oil (or omega-6 oil) in the lipid-based oil-in-water emulsion is expressed by weight in grams of omega-3 (or omega-6 oil) per 100 mL emulsion.

As used herein, the amount of glyceride (mono-, di-, or triglyceride) in the omega-3 oil (or omega-6 oil) oil is expressed as the percentage of the glyceride by weight per total weight of the omega-3 (or omega-6 oil).

As used herein, the amount of fatty acid such as EPA or DHA in a glyceride (mono-, di-, or triglyceride) is expressed as the % of the total acyl groups of the respective glyceride.

As used herein, hypoxia refers to a shortage of oxygen in the body or in a specific organ or tissue.

As used herein, ischemia refers to insufficient blood flow to provide adequate oxygenation. The most common causes of ischemia are acute arterial thrombus formation, chronic narrowing (stenosis) of a supply artery that is often caused by atherosclerotic disease, and arterial vasospasm. As blood flow is reduced to an organ, oxygen extraction increases. When the tissue is unable to extract adequate oxygen, the partial pressure of oxygen within the +tissue fails (hypoxia) leading to a reduction in mitochondrial respiration and oxidative metabolism. Further, in many acute situations of organ ischemia-hypoxia (e.g., stroke, myocardial infarction, intestinal *volvulus*, etc.) the patient is far too ill to have oral or enteral administration of therapeutic agents and thus needs parenteral injections, such as from lipid emulsions for immediate action.

As used herein, hypoxia-ischemia refers to the occurrence of both hypoxia and ischemia in a tissue or organ.

As used herein "perfusion buffer" refers collectively to washout, preservation, intracellular and flush solutions devised and evaluated for cold storage of an isolated organ or tissue that has been removed from the body that is intended for transplantation. The isolated organ/tissue is perfused, reperfused, stored or otherwise contacted immediately after removal from the body with such a buffer or solution. The use of the term "intracellular" solutions is due to their resemblance, in some respects, to intracellular fluid.

As used herein, "perfusion" refers to perfusing an isolated organ or tissue after isolation from the body, and "reperfusion" refers to subsequent perfusions after the organ or tissue has undergone an ischemic event.

As used herein, "n-3 glyceride perfusion emulsions" of the present invention refer to perfusion buffers that comprise less than 7% n-3 oil by weight per 100 ml of emulsion, and less than 10% n-6 oil by weight per 100 ml of emulsion.

As used herein, the amount of n-3 oil (diglyceride, triglyceride) in the emulsion is expressed as % TG or DG by weight per total weight of the n-3 oil.

As used herein, "tissue" is used herein to mean any controlled medical support product or biological substance such tissues, biological specimens or other medical products that require special conditions during transport.

As used herein, an "organ" is a collection of cells and tissues joined in a structural unit to serve a common function. Organs include any organ that can be transplanted including the heart, kidneys, liver, lungs, pancreas, intestine, and *thymus*. Tissues include bones, tendons (both referred to as musculoskeletal grafts), composite tissue allografts, cornea, skin, heart valves, nerves and veins. A "transplant organ" as used herein may refer to an organ that is also a donor organ and/or an organ that is intended for transplantation. "Transplant organ" may refer to a donor organ that has yet to be transferred to a recipient.

As used herein, "reperfusion damage" or "reperfusion injury" are used interchangeably herein to refer to damage caused with restoration of blood supply to hypoxic-ischemic (H/I) tissues either in vivo after an ischemic event or ex vivo in isolated organs and tissues. An ischemia-reperfusion injury can be caused, for example, by a natural event (e.g., restoration of blood flow following a myocardial infarction), a trauma, or by one or more surgical procedures or other therapeutic interventions that restore blood flow to a tissue or organ that has been subjected to a diminished supply of blood. Such surgical procedures include, for example, coronary artery bypass graft surgery, coronary angioplasty, organ transplant surgery and the like.

2. SUMMARY OF EMBODIMENTS

It has been discovered that isolated hearts reperfused for an hour ex vivo after 30 min. of induced ischemia, retained dramatically higher function when reperfused in buffer to which omega-3 triglyceride oil had been added. The isolated hearts were reperfused with a dilute n-3 glyceride perfusion emulsion having 0.3% n-3 triglyceride oil in grams/100 ml of perfusion buffer. Hearts reperfused in the n-3 triglyceride emulsion maintained a normal heart rate and normal left ventricular developed pressure (LVDP) and showed a dramatically reduced frequency of arrhythmias compared to control hearts. Further, test hearts reperfused n-3 oil triglyceride emulsion showed a decrease in creatine kinase and upregulation of certain beneficial proteins including the anti-apoptotic gene marker Bcl-2. Reperfusion with the n-3 triglyceride perfusion emulsion also down-regulated harmful proteins including HIF1 (a marker for autophagy which may increase cell death), PPAR gamma (associated with some pro-inflammatory responses in heart), and Beclin 1 (an autophagic marker). These ex vivo results using a 0.3% n-3-TG-containing emulsion to reperfuse isolated hearts after induced ischemia are consistent with observations presented in Examples 3-5 showing that in vivo administration of various n-3 triglyceride (TG) and diglyceride-(DG) oil-in-water emulsions to animals having suffered hypoxia/ischemia dramatically reduced reperfusion injury the brain and heart.

While not wishing to be bound by theory, it is believed that the omega-3 fatty acid content of cell membranes of certain isolated organs (such as the heart, lungs and brain) and tissues can be preserved and also increased by being stored, perfused, reperfused or otherwise contacted with omega-3 di- and tri-glyceride emulsions. It has been speculated that n-3 diglycerides are hydrolyzed faster than triglycerides, and that 1, 2-diglycerides are also highly bioactive molecules. It has been speculated that diglyceride emulsion droplets are more efficiently taken up by organs than triglyceride emulsion droplets.

Based on the collective results described herein, certain embodiments of the invention are directed to new omega-3 oil-in-water perfusion glyceride emulsions (herein also "n-3 glyceride (TG or DG) perfusion emulsions") that comprise less than 7% n-3 TG- or DG-oil by weight in grams per 100 ml of emulsion, wherein the n-3 oil is mixed with perfusion buffer. Any standard perfusion buffer for preserving, storing and perfusing/reperfusing isolated organs and tissues ex vivo can be used in the n-3 glyceride perfusion emulsions of the invention. The perfusion buffers are based on a balanced isotonic solution that typically includes sodium, potassium, calcium and magnesium ions, as well as glucose and sodium bicarbonate, in a physiologically acceptable amount. Certain of these types of solutions are well known in the art. The omega-3 glyceride perfusion emulsions of the invention are nontoxic and stable for extended periods of time.

Certain other embodiments are directed to methods of preserving an isolated organ or tissue by contacting it with an n-3 glyceride perfusion emulsion of the invention ex vivo, for example for a predetermined duration of time (typically 1 to 24 hours) at a predetermined temperature. Storage and perfusion/reperfusion temperatures can vary widely, typically from about 0° C. to about 37° C. In some embodiments the organ or tissue is contacted with the omega-3 glyceride perfusion emulsions of the invention by static cold storage or low temperature continuous perfusion/reperfusion, at a temperature within in a range of about −5° C. to about 10° C.

In an embodiment, the new n-3 glyceride perfusion emulsions comprise:
  (a) a perfusion buffer suitable for organ or tissue preservation and transplantation,
  (b) less than 7% of an omega-3 oil by weight in grams per 100 ml of perfusion buffer, wherein the omega-3 oil
    (i) comprises from about 10% to about 99% omega-3 diglyceride, omega-3 triglyceride or combinations thereof by weight per total weight of the omega-3 oil, wherein about 20% to about 99% of the total acyl groups of the diglycerides or triglycerides consist of EPA or DHA, and
    (ii) comprises less than 10% omega-6 fatty acids by weight per total weight of the omega-3 oil,
  (c) less than 10% of an omega-6 oil, and
  (d) the mean diameter of lipid droplets in the emulsion is less than about 5 microns.

The omega-3 glyceride perfusion emulsions of the invention can have:
  (a) from about 0.5 to about 1%, 1-3%, 3-5% or 5-less than 7% omega-3 oil;
  (b) from about 10% to about 20%, from 20% to about 40%, from 40% to about 60% and from 60-99% of the n-3 oil can be TG or DG; and
  (c) from about 20% to 50%, from 50% to 75%, from 75% to 90%, from 90% to 95% or from 95% to 100% of the total acyl groups of the omega-3 diglycerides or triglycerides consisting of EPA or DHA.

In some embodiments the mean diameter of lipid droplets in the emulsion is less than about 5 microns, less than 1 micron or less than 500 nm.

In certain embodiments, the omega-3 oil is fish oil, synthetic omega-3 oil or a combination thereof. Other embodiments of new perfusion emulsions are described below in more detail. In certain embodiments, the omega-3 oil is about 10% to about 97% omega-3 TG and at least 30%, 40% or 50% of the total acyl groups on the TG are DHA (herein "Tri-DHA perfusion emulsions"); however, this can vary widely, up to 99%. A specific example is the "TG90-DHA30" Tri-DHA emulsion that was administered in vivo following H/I to reduce reperfusion injury at a concentration of 10% omega-3 oil by weight in grams per 100 ml of emulsion, wherein the omega-3 oil is >90% triglyceride (TG) by weight per total weight of the omega-3 oil, and in which up to about 30% of the total acyl groups are DHA. In other embodiments the omega-3 oil is at least 20%, 40%, 60% DG and at least 30%, 40% or 50% of the total acyl groups on the TG are DHA (herein "Tri-DHA perfusion emulsions"); however, this can vary widely, up to 99%.

The omega-3 TG- and DG-perfusion emulsions of the present invention are not naturally occurring. For example, there is no omega-3 oil found in nature that comprises at least 20% omega-3 diglycerides wherein at least 20% of the total acyl-groups of the omega-3 di- or tri-glycerides consist of EPA or DHA. The highest percentage EPA plus DHA in an omega-3 oil is found in sardine and anchovy oil, where the combined percentage EPA and DHA might be as high as only 27% to 28%. Racine R A, Deckelbaum R J., Curr Opin Clin Nutr Metab Care. 2007 March; 10(2):123-8. Extraordinary measures have to be taken to obtain a triglyceride (TG) or a diglyceride (DG) n-3 oil in which more than 20% of the total acyl groups are either EPA or DHA, such as hydrolyzing the fatty acids off of fish oil n-3 triglycerides. The DHA and EPA are then purified and separated from other fatty acids in the preparation, and then the DHA and/or EPA are re-esterified back onto a glycerol molecule to make an n-3 DG or TG wherein more than 20% of the fatty acids are DHA and EPA.

Sources of omega-3 fatty acids may be from any suitable source such as from fish oils, other oils or may be synthesized. Although EPA and DHA are preferred omega-3 fatty acids, other omega-3 fatty acids may be used such as docosapentaenoic acid. Suitable exemplary fish oils for use in the present perfusion/reperfusion emulsions include oils from cold-water fish such as salmon, sardine, mackerel, herring, anchovy, smelt and swordfish. Fish oils generally contain glycerides of fatty acids with chain lengths of 12 to 22 carbons. Non-naturally occurring, highly purified fish oil concentrates obtained, for example, from sardine, salmon, herring and/or mackerel oils may have an eicosapentaenoic acid (EPA) content of from about 20 to 40 wt.-%, and a docosahexaenoic acid (DHA) content of >10% based on the fatty acid methyl esters of the fish oil concentrate as determined by gas chromatography (percent by area). U.S. Pat. No. 6,159,523 discloses a method for making fish oil concentrates. Generally, the amount of the polyunsaturated fatty acids of the omega-6 series (such as linoleic acid) in natural fish oils is low, i.e. less than 10%, and typically less than 5%. In the described n-3 perfusion/reperfusion emulsions of the present inventions, the amount of omega-6 oil in the overall emulsions is less than 10% by weight in grams per 100 ml of perfusion buffer, wherein the omega-3 oil, preferably less than 5%; and the amount of omega-6 oil in the omega-3 oil of the emulsion is also less than 10% by weight in grams per 100 ml of perfusion buffer, wherein the omega-3 oil, preferably less than 5%. N-3 TG with more than about 25% of the total acyl groups of the TG consisting of DHA or EPA is typically synthesized and/or purified.

3. BACKGROUND

Much of the injury to transplanted organs occurs not during ischemia, but during reperfusion. This finding has led to many advances in organ preservation aimed at preventing this type of injury. Furthermore, some of the events that occur during reperfusion may result in enhanced immunogenicity of the graft. Oxygen free-radicals generated during reperfusion are a major cause of the reperfusion injury, but cytokines and nitric oxide also play a role.

Damage to organs during transplantation typically occurs in two phases. The first, the warm ischemic phase, includes the time from the interruption of circulation to the donor organ to the time the organ is flushed with hypothermic preservation solution. In multiorgan recovery, the organs are cooled before they are removed. The second, the cold ischemic phase, occurs when the organ is preserved in a hypothermic state prior to transplantation into the recipient. The stability of the membrane to chemical and water permeability depends on the integrity of the lipid bilayer and on tight control of temperature, pH, and osmolarity which are disrupted by ischemia. Lowering the temperature causes a phase transition of lipids and results in profound changes in membrane stability. In addition, it drastically alters the function of membrane-bound enzymes. Hypothermia-induced structural changes in the membrane increase permeability, which contributes to cell swelling. Therefore, organ-preservation solutions are hypertonic to minimize these alterations.

Until relatively recently, the primary solution used for cold-storage preservation of the kidneys was Euro-Collins solution. Its formulation provides a hyperosmolar environment with an intracellular electrolyte composition intended to reduce cellular swelling. In combination with hypothermia, kidneys can be safely stored in this solution for up to 36-48 hours before transplantation. Groenewoud A F, Thorogood J. A preliminary report of the HTK randomized multicenter study comparing kidney graft preservation with HTK and EuroCollins solutions. HTK Study Group. *Transpl Int.* 1992; 5 Suppl 1:S429-32.

There are currently two modes of preservation methods for kidneys and livers: static and dynamic. Simple cold storage (SCS) is the main method for static storage while hypothermic machine perfusion (HMP), normothermic machine perfusion (NMP) and oxygen persufflation (OP) comprise the methods for dynamic preservation. Of these four methods, only SCS and HMP are approved clinically for kidneys and only SCS for livers. The remaining methods are in various stages of pre-clinical and early clinical studies. The first successful human preservation of a kidney for 17 hours: Lee, et al, Organogenesis. 2009 July-September; 5(3): 105-112. *Hypothermic machine perfusion (HMP) preservation.* Hypothermic machine perfusion was developed for kidneys to extend both preservation time and preservation quality.

The kidney is the most widely transplanted organ with the longest history of preservation research. Simple SCS can reliably provide good early function in the majority of grafts where storage times over 36 h have not been required within modern integrated transplant networks. Revolutionary new designs for kidney perfusion machines and a shift towards marginal donors led to a re-evaluation of HMP. A prospective multi-centre trial has demonstrated a clear outcome benefit for both delayed graft function and graft survival at 1 year. The perfusate used was a formulation of University of Wisconsin (UW) solution, where lactobionate was replaced by gluconate. The introduction of UW solution allowed good preservation of liver to be extended to around 15 h. Guibert, E., et al., Transfus Med Hemother. April 2011; 38(2): 125-142.

The mainstay of clinical lung preservation has been simple hypothermic immersion of inflated lungs following flush of the pulmonary artery with chilled preservation solution. Low potassium solutions such as the Wallwork solution have been favoured. The routine application of lung inflation during preservation renders the lungs capable of some aerobic metabolic activity and has led to increased interest in including NHBD donor lungs for clinical preservation. There are occasions where lungs and heart are cold preserved en bloc using cold carioplogic arrest of the heart followed by pulmonary flush of a second preservation solution (such as Euro-Collins solution) for the lungs. Guibert. E. et al. (2011).

There are two steps in cardiac SCS. First cardiac activity is stopped in a controlled fashion by flushing the vascular bed of the organ with chilled cardiaplegic solution to cool and wash out the blood. Solutions such as St. Thomas' cardiaplegic solution are used in the majority of centres. Then hearts are generally also topically cooled with chilled sterile saline before packing and storage in ice to provide satisfactory preservation in the range of 4-6 h. Instead of storing and packing in saline, the n-3 glyceride perfusion emulsions of the present invention can be used to improve preservation.

In principle, cold flush storage or preservation is based upon the premise that temperature reduction to near but not below the ice point (e.g., about 0° C.) precludes the need to support metabolism to any significant extent, and that the correct distribution of water and ions between the intracellular and extracellular compartments can be maintained by physical rather than metabolic means. During a period that metabolic pumps are inactivated, the driving force for transmembrane ion flux is the difference in ionic balance between intracellular and extracellular fluid. The driving force for water uptake (cell swelling) is the impermeant intracellular anions. Thus changes can be prevented or restricted by manipulating the extracellular environment to abolish chemical potential gradients. On this basis, a variety of flush, or organ and tissue washout solutions have been devised and evaluated for cold storage. These solutions are often referred to as "intracellular" solutions due to their resemblance, in some respects, to intracellular fluid. The n-3 perfusion/reperfusion emulsions are types of washout, preservation, intracellular and flush solutions.

Generally, the two most frequently used methods for preserving organs after removal from the donor are simple hypothermic storage and continuous pulsatile perfusion. With simple hypothermic storage, the organ is removed from the donor and cooled rapidly. This is usually achieved by a combination of cooling and short periods of perfusion to drop the organ temperature as quickly as possible to a temperature between 0° C. and 4° C. where it may be held for up to about six hours or significantly longer, even up to 72 hours in some cases. The duration depends in part on the organ or tissue. While cold storage enables organs to be transplanted, the time during which the organ is viable is short. Cold storage decreases the rate at which intracellular enzymes, essential cellular components necessary for organ viability, degrade but does not stop metabolism entirely.

The second method of organ preservation which has undergone extensive investigation, continuous pulsatile perfusion, utilizes the following elements: (1) pulsatile flow, (2) hypothermia, (3) membrane oxygenation, and (4) a perfusion buffer. Although being more technically complex and costly, continuous pulsatile perfusion provides significantly longer viability of the organ when compared to simple hypothermia.

Preserving organs at between 0° C. and 4° C. can result in damage to the organ during storage and upon reperfusion, with a warm reperfusion solution. Injury to the organ occurs through damage to epithelial and endothelial cells. Although some of the solutions of the prior art have been useful to extend the storage time of donor organs and lessen injury to the organ upon reperfusion, cell injury still does occur frequently. It is desirable to extend the viable organ life and improve the quality of the transplanted organ. Extending organ viability allows sufficient time for compatibility testing of the donor and recipient, and increased organ availability. Ischemia-reperfusion injury to transplanted organs preserved in solutions of the prior art is still often associated with loss of viability such as delayed graft function, and predisposition to acute and chronic rejection.

The principle design elements of organ and tissue perfusion/reperfusion buffers include adjusting the ionic balance (notably of the monovalent cations) and raising the osmolality by including an impermeant solute to balance the intracellular osmotic pressure responsible for water uptake.

Prior to 1988, a standard solution for clinical preservation of organs and tissues was Collins solution, which includes potassium phosphate, magnesium sulfate and glucose. In recent years, however, this has been superseded either by a modified version called "Euro-Collins" in which the magnesium sulfate is omitted, or more extensively by the University of Wisconsin solution (UW solution) in which much of the phosphate anion has been replaced with lactobionate, and in which glucose has been replaced with raffinose. These larger molecules appear to improve protection against adverse effects of cell swelling during hypothermic storage, as compared to prior solutions.

Preservation solutions are designed to prevent or inhibit various mechanisms which cause injury to the organ, and thus they perform one or more (and preferably all) of the following functions: (1) prevent or restrict intracellular acidosis, (2) prevent the expansion of intracellular space, (3) prevent injury from oxygen-derived free radicals, especially during reperfusion, (4) enable the regeneration of high-energy phosphate compounds during reperfusion, (5) sustain appropriate metabolic requirements and prevent the rapid changes in intracellular ions including $N^+$, $—H^+$ and $Ca^{2+}$ following reperfusion.

4. SUMMARY OF RESULTS AND EMBODIMENTS OF THE INVENTION

The following is a summary of results of experiments described in the Examples of this application.

Perfusion of Isolated Hearts Ex Vivo with n-3 Glyceride Perfusion Emulsions Reduced Reperfusion Damage after an Ischemic Event (Details in Example 2)

An ex vivo model using hearts removed from C57BL/6 mice and perfused in the well-known Langendorff system was used. After a period of 30 min of induced ischemia, hearts were reperfused for 1 hour. Control hearts reperfused perfusion buffer without n-3 triglycerides, showed that heart rate was reduced, LVDP was markedly decreased, and arrhythmias were observed. Test hearts were reperfused in perfusion buffer with n-3 triglycerides ("n-3 TG perfusion emulsion") which maintained a normal heart rate, normal LVDP, and dramatically reduced the occurrence of arrhythmias. Hearts perfused with n-3 triglycerides had close to 100% (or normal) recovery.

After 1 hour of reperfusion with the test n-3 triglyceride reperfusion buffer, there was over a 90% recovery of LVDP compared to only a 40% LVDP recovery in the control reperfusion buffer. In addition, heart rate recovery was improved with n-3 triglyceride reperfusion buffer;

Markers of myocardial infarction such as creatine kinase were markedly decreased in the reperfusion of isolated hearts in the test n-3 triglyceride reperfusion buffer. Increases in level of the anti-apoptotic gene marker, Bcl-2, and in expression of Bcl-2 mRNA were also shown. In contrast, both the level of protein and mRNA for HIF1, a marker for autophagy which may increase cell death, were down-regulated after reperfusion with the test n-3 triglyceride reperfusion buffer.

Another autophagic marker, Beclin 1, was also decreased in terms of protein expression and mRNA expression after reperfusion with buffer containing n-3 glycerides.

PPAR gamma protein expression, associated with pro-inflammatory responses in heart, is markedly increased after reperfusion in control hearts but decreased after reperfusion containing n-3 glycerides.

To summarize, including n-3 glycerides in the perfusion buffer during reperfusion after induced ischemia decreased the marker of myocardial infarction creatine kinase, and upregulated beneficial proteins including the anti-apoptotic gene marker Bcl-2. Reperfusion with perfusion buffer including N-3 TG downregulated of harmful proteins including HIF1 (a marker for autophagy which may increase cell death), PPAR gamma (associated with pro-inflammatory responses in heart), and Beclin 1 (an autophagic marker) were down-regulated.

Administration of n-3 TG Emulsions In Vivo Reduced Reperfusion Injury after H/I (Details are in Examples 3 and 4)

As used herein "Tri-DHA" means n-3 triglyceride emulsions rich in DHA having at least 30% DHA; often over 90% of the TG fatty acids are DHA. TG90-DHA30 emulsion that was administered in vivo following H/I to reduce reperfusion injury at a concentration of 10% omega-3 fish oil by weight in grams per 100 ml of emulsion, wherein the omega-3 oil is >90% triglyceride (TG) by weight per total weight of the omega-3 oil, and in which up to about 30% of the total acyl groups of the TG are DHA.

Effects of in vivo administration of n-3 TG emulsions rich in DHA (specifically "TG90-DHA30") on blood triglyceride levels after injection indicated that TG levels were substantially increased up to three-fold higher at 1.5 hours compared to baseline, followed by a decrease of levels to baseline at 3 and 5 hours due to the fact that n-3 TG had entered into the blood stream and was being catabolized.

Figure 17:
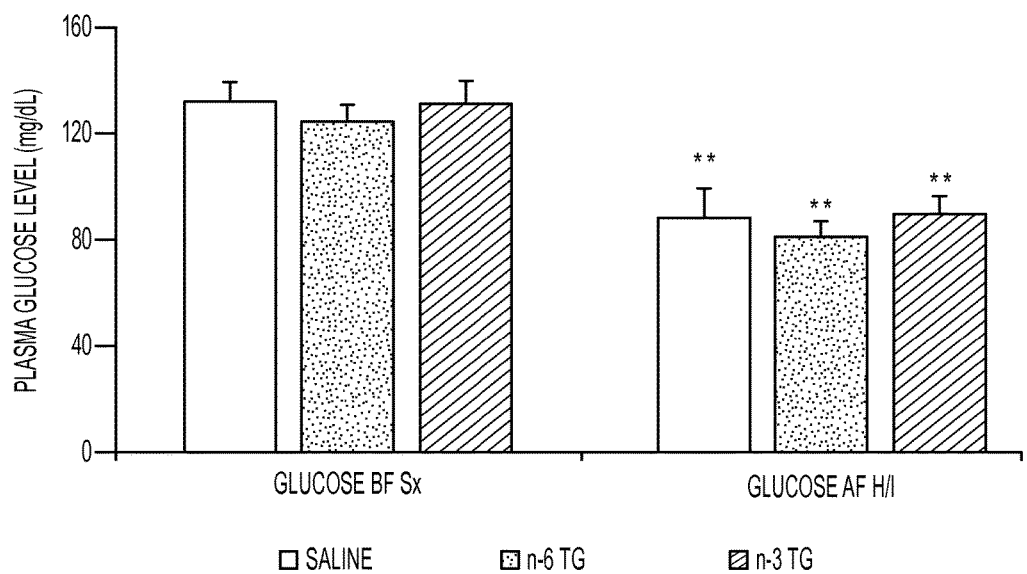
FIG. 17 illustrates plasma glucose concentrations (mg/dL) in non-fasting mice (p10) in post-H/I treatment of n-3 TG or n-6 TG or vehicle (saline) comparing to the time between before H/I and after H/I. **p<0.001 (n=5-9 in each group).

After H/I it was determined that there was no difference in blood glucose levels among TG90-DHA30 vs. n-6 TG vs. saline control; and no difference was observed in capillary bleeding times in n-3 TG90-DHA30 treated mice as compared to saline controls. FIG. 17.

n-3 TG did not change cerebral blood flow after H/I since very similar blood flow levels were maintained in neonatal H/I mice whether they were saline-treated or n-3 TG90-DHA30-treated.

n-3 TG90-DHA30 but not n-6 TG protected the brain against H/I injury as evidenced by the subcortical region of the brain where infarct volume was substantially decreased in n-3 TG treated mice but a significant increase in infarct volume occurred with n-6 TG emulsion injection.

In immediate post-H/I treatment the total brain infarct area was significantly reduced almost 50% in the n-3 TG90-DHA30 post H/I treated group.

DHA but not EPA was neuroprotective after H/I as evidenced by total infarct size reduction by a mean of 48% and 55% with treatment of 0.1 and 0.375 g TG wherein the DHA=99% of the total acyl groups on the TG, respectively, compared with saline control. However, neuroprotection was not observed with Tri-EPA injection wherein the EPA=99% of the total acyl groups on the TG at either of the two doses compared with saline treatment.

No protective effect from TG90-DHA30 after a 4-hour delay in treatment was observed compared with control, but TG90-DHA30 administered at 0 hour immediately post-H/I, and then delayed 1-hr, and 2-hr post stroke showed similar reduced brain infarct volumes (~50%) compared to control.

Effects of H/I and TG90-DHA30 treatment on brain and neuronal cell loss were measured for long-term outcome at 8 weeks after H/I insult and it was found that neuroprotection after injury and TG90-DHA30 injection that was observed 24 hours after H/I can be seen histologically approximately 2 months after the initial stroke insult.

5. METHODS OF PERFUSION AND REPERFUSION

The n-3 glyceride perfusion emulsions of the present invention are designed to preserve and store the organ (or tissue) with the preservation solution and reperfuse with preservation solution prior to implantation. Typically, the surgeon removes the organ and connects it to a perfusion apparatus comprising tubing and pumps. The preservation solution is then perfused through the organ while gassed with oxygen and carbon dioxide while it is awaiting implantation into a patient. A perfusion rate of from about 25 to about 150 mL/hour, or about 50 mL/hour, at 1° C. has been found to be effective. However, routine experimentation can optimize this process and varies according to the temperature of duration of organ/tissue storage. Organ perfusion can occur at either a constant flow or pressure.

The preservation solution can be used at all temperatures ranging from 0° C. to normal body temperature, 37° C. The duration of perfusion/reperfusion and the temperature is selected in order to optimize the process of sustaining, maintaining or improving the viability of the organ/tissue while being stored, for example before and/or during transplantation. In an embodiment of a method of the present invention, organs/tissues can be used at predominately hypothermic temperatures, to provide a decrease in organ metabolism, lower the energy requirements, delay the depletion of high energy phosphate reserves and accumulation of lactic acid and retard the morphological and functional deterioration associated with disruption of blood supply. Alternatively, a method for storing a particular organ may be selected that first employs mid-normothermic to normothermic temperatures to improve the viability of the organ and/or tissue until an organ and/or tissue meeting a predetermined threshold viability index is obtained (which may vary from organ to organ), thereafter hypothermic temperatures may be employed to provide a decrease in organ metabolism, lower the energy requirements, delay the depletion of high energy phosphate reserves and accumulation of lactic acid and retard the morphological and functional deterioration associated with disruption of blood supply.

Exemplary organ perfusion methods are described in US 20040237693; US 20090311663; US 20110173023; 20120315618; and 20100278934.

Organ perfusion apparatus are available to perfuse one or more organs simultaneously, at normothermic, near-normothermic, mid-normothermic and hypothermic temperatures (hereinafter, normothermic, near-normothermic, mid-normothermic and hypothermic perfusion modes).

Plasma-like electrolytes as base for oxygen carrying molecules and other substrates are sometimes necessary for optimized "normothermic" perfusion Cryo-Concentrated Intracellular Base plus permeating or non-permeating cryoprotective additives can be used for sub-zero preservation of cells and tissues.

In embodiments, multiple n-3 glyceride perfusion/reperfusion emulsions that are not identical can be perfused/reperfused into the organ or tissue.

In embodiments, the n-3 glyceride perfusion emulsions are administered/perfused to the organ (or tissue) while it is maintained in a predetermined temperature range, such as from about 10° C. to about 37° C., or from about 15° C. to about 37° C., or from about 20° C. to about 37° C., or from about 20° C. to about 30° C., or from about 20° C. to about 25° C.

Ex vivo perfusion of an isolated organ (or tissue) includes treatment of the organ (or tissue) that has endured a period or periods of ischemia and/or apoxia with the n-3 glyceride emulsions of the invention. Ex vivo treatments may involve performing surgical techniques on an organ, such as cutting and suturing an organ, for example to remove necrotic tissue.

The above methods may be used for mammalian organs, including humans, including small organs from a child as well as large or adult organs.

The optimum perfusate regimen/therapy and/or temperature mode for maintaining, restoring, and improving the viability of isolated organs/tissues in order to meet a predetermined threshold viability index, may vary from organ to organ and tissue to tissue, and may depend on the condition or state the organ/tissue was received in (e.g., differences include heart-beating donors versus non-heart beating donors and amount of time the organ has been out of the body).

In embodiments, depending on the particular organ therapy decision and the decision regarding whether to transplant the organ, normothermic perfusion may be preceded by and/or followed by hypothermic perfusion, near-normothermic perfusion, or mid-normothermic perfusion or combinations thereof. Such perfusion conditions may also be employed in vivo as well as in vitro prior to removal of the organ from the donor.

6. OMEGA-3 OILS

Lipid generally refers to a group of natural substances which are soluble in hydrocarbon and insoluble in water. Lipids include any fat-soluble (hydrophobic) naturally-occurring molecules. The term is more specifically used to refer to fatty-acids and their derivatives (including tri-, di-, and monoglycerides and phospholipids) as well as other fat-soluble sterol-containing metabolites such as cholesterol.

Chemically, fatty acids can be described as long-chain monocarboxylic acids the saturated examples of which have a general structure of $CH_3(CH_2)_nCOOH$. The length of the carbon chain usually ranges from 12 to 24, always with an even number of carbon atoms. When the carbon chain contains no double bonds, it is a saturated chain. If it contains one or more such bonds, it is unsaturated. The presence of double bonds reduces the melting point of fatty acids. Furthermore, unsaturated fatty acids can occur either in cis or trans geometric isomers. In a vast majority of naturally occurring fatty acids, the double bonds are in the cis-configuration.

Polyunsaturated fatty acids (PUFA) include omega-6 (also known as w-6 or n-6) and omega-3 (also known as ω-3 or n-3) polyunsaturated fatty acids. The designation as omega-3 or omega-6 is based on the fatty acid structure, namely the distance of the first unsaturated bond from the methyl (omega) end of the fatty acid molecule. Omega-3 polyunsaturated fatty acids mainly include cis-20:5($\Delta 5,8,11,14,17$)-eicosapentaenoic acid (EPA); cis-22:5($\Delta 7,10,13,16,19$)-docosapentaenoic acid (DPA); cis-22:6($\Delta 4,7,10,13,16,19$)-docosahexaenoic acid (DHA); and cis-18:3($\Delta 3,6,9$)-a-linoleic acid. Omega-6 polyunsaturated fatty acids mainly include cis-18:2($\Delta 9,12$)-linoleic acid and cis-20:4($\Delta 5, 8, 11, 14$)-arachidonic acid.

Glycerol is a chemical compound with the formula $HOCH_2CH(OH)CH_2OH$. Glycerides are lipids possessing a glycerol (a crude name for which is propan-1, 2, 3-triol) core structure with one or more fatty acyl groups, which are fatty acid-derived chains attached to the glycerol backbone by ester linkages.

A diglyceride ("DG"), also known as a diacylglycerol, is a glyceride consisting of two fatty acid chains covalently bonded to a glycerol molecule tough ester linkages. A triglyceride ("TG") (also known as triacylglycerol or triacylglyceride) is a glyceride in which the glycerol is esterified with three fatty acids. An acyl group is a function group derived by the removal of one or more hydroxyl group and oxoacid.

Triglycerides ("TG") may also be classified as having a long or medium chain length. Long chain triglycerides preferably contain fatty acids with 14 or more carbons, while medium chain triglycerides preferably contain fatty acids with 6 to 12 carbons. Long chain triglycerides may include omega- and omega-6 fatty acids. Medium chain triglycerides have saturated fatty acids and thus do not contain omega-6 or omega-3 fatty acids. Long chain triglycerides (LCT) and medium chain triglycerides (MCT) may serve as energy sources. Medium chain triglycerides may influence the metabolism of emulsion droplets because of their fast hydrolysis and other properties (i.e. enhancing particle binding to cells, changing cell membrane properties).

The human body is capable of synthesizing certain types of fatty acids. However, long chain omega-3 and omega-6 are designated as "essential" fatty acids because they cannot be produced by the human body and must be obtained through other sources. For example, fish oils from cold-water fish have high omega-3 polyunsaturated fatty acids content with lower omega-6 fatty acid content. Table 1 was supplied by the manufacturer of the n-3 Tri-DHA oil Fresenius Kabi, and it describes the make-up of the n-3 Tri-DHA used in some of the experiments described herein. Table 1 estimates (in column 2) that the n-3 fish oil comprises a range of 1-7% in gm/100 ml Linoleic acid (C18: 2n-6), and 1-4% Arachidonic acid (C20: 4n-6), which together have a theoretical upper limit of 11%. However, to date no fish oil used as a major source of omega-3 fatty acids has been reported that has over 10% omega-6 fatty acids. The di- and tri-glyceride omega-3 emulsions of the present invention when made from fish oil, use fish oil with 10% or less omega-6 fatty acid. Most vegetable oils (i.e., soybean and safflower) have high omega-6 polyunsaturated fatty acids (most in the form of 18:2 ($\Delta^{9,12}$)-linoleic acid) content but low omega-3 (predominantly 18:3 ($\Delta^{9,12,15}$)-α-linolenic acid) content.

Methods of synthesizing di- and triglycerides rich in n-3 fatty acids are well known in the art, and are disclosed, for example, in U.S. Pat. Nos. 2,206,168; 2,626,952; 3A10, 881; 3,634,473; 3,097,098; 3,551,464; 4,018,806; 5,106,542; 5,130,061; 5,142,071; 5,142,072; 5,959,128; 5,434,280; 6,004,611; 6,337,414; 6,537,787; 6,749,881; and 7,081,542 all of which are incorporated herein by reference. Thus, the diglycerides and triglycerides may be obtained by transesterification of various oils (such as fish oil or rapeseed oil) containing omega-3 unsaturated acyl-groups, and/or monoenoic acyl-groups with glycerol. Di- and triglycerides may also be obtained by esterification of a fatty acid derived from such an oil with glycerol. In the n-3 glyceride perfusion emulsions of the present invention, the omega-3 di- and triglycerides are typically derived from fish oil, or synthesized so as to contain less than about 3% omega-6 fatty acids. Fish oils include natural fish oils, processed fish oils, highly purified fish oil concentrates or (re)esterified (synthetic) fish oils, including (re-)esterification of omega-3-fatty acids from cold water fish oil by triglyceride hydrolysis, purification and concentration of the resultant omega-3-fatty acids with glycerol. Processed fish oils are described in European published patent application EP-A-0298293, which is incorporated herein by reference in its entirety.

Suitable exemplary fish oils include oils from cold-water fish such as salmon, sardine, mackerel, herring, anchovy, smelt and swordfish. Fish oils generally contain glycerides of fatty acids with chain lengths of 12 to 22 carbons. Highly purified fish oil concentrates obtained, for example, from sardine, salmon, herring and/or mackerel oils may have an eicosapentaenoic acid (EPA) content of from about 9-10 or up to ~20% of total TG fatty acids, and a docosahexaenoic acid (DHA) content of 10% up to ~20% based on the fatty acid methyl esters analyses of the fish oil concentrate as determined by gas chromatography (percent by area). U.S. Pat. No. 6,159,523, incorporated herein by reference in its entirety, discloses a method for making fish oil concentrates. Generally, the amount of the polyunsaturated fatty acids of the omega-6 series (such as linoleic acid) in natural fish oils is low, i.e. less than 10%, typically less than 5% of total fatty acids by weight.

Also, trans-esterification reactions may be performed by chemical means (such as using an alkali catalyst, i.e. sodium methoxide). Or, di- and triglycerides may be prepared by enzymatic approaches with lipases. The resulting glyceride may be further processed by isomerase to yield a 1,2 or 1,3-glyceride.

Omega-3 EPA and DHA may be obtained from any source. For example, EPA or DHA may be synthetic, isolated from natural products such as krill oil, or obtained from fish oil by alkaline hydrolysis. Fish oil is currently and generally the least expensive source of EPA and DHA.

Based on the total amount of acyl groups, in certain embodiments at least about 20% to 99% of the total acyl-groups of the omega-3 diglycerides or triglycerides comprise EPA or DHA.

In other embodiments, the new omega-3 glyceride perfusion emulsions of the present invention may further comprise from about 0% to about 10% of monoglycerides of DHA and/or EPA. The monoglycerides of DHA and/or EPA are from about 0% to about 10%, or from about 0% to about 2%, based on the total amount of lipid.

New omega-3 glyceride perfusion emulsions of the present invention may also further comprise from about 0% to about 20% total free unsaturated fatty acids by weight. Typically the unsaturated fatty acids are from about 0% to about 5%, or from about 0% to about 2%, based on the total amount of fatty acids by weight in the lipid phase. In certain embodiments of the invention, omega-3 glyceride perfusion emulsions comprise medium chain triglycerides (MCT). These omega-3 glyceride perfusion emulsions may contain as a percent of total n-3 lipid, and from 0% to 90% medium chain di- or triglycerides of total glycerides, or from about 0% to about 60%, or from about 40% to about 60% of total glycerides. Medium chain di- or triglycerides may contain fatty acids with 6 to 12 carbons. The medium-chain triglycerides ("MCT") administered with the lipid emulsions serve mainly as a source of energy; they contain saturated fatty acids and hence contain neither the omega-6 nor omega-3 essential fatty acids. Because of their fast hydrolysis as well as other properties (enhancing particle binding to cells), MCT may have a positive effect on the metabolism of emulsion particles.

7. PHARMACEUTICAL FORMULATIONS OF N-3 GLYCERIDE PERFUSION EMULSIONS

Omega-3 glyceride perfusion emulsions of the present invention have less than 7% of an omega-3 oil by weight in grams per 100 ml of perfusion buffer, with embodiments ranging from about 0.5 to about 1%, 1-3%, 3-5% or 5-less than 7% omega-3 oil weight in grams per 100 ml of perfusion buffer. In the ex vivo heart example, herein, the amount was only 0.3%. Significantly higher % n-3 emulsions (7-35% n-3 oil weight in grams per 100 ml of perfusion buffer) are used for in vivo administration to reduce reperfusion injury after H/I because the concentration is diluted in the body. Organs and tissues stored in the n-3 glyceride perfusion emulsions of the present invention can be perfused/reperfused with emulsions having much lower n-3 oil content.

The omega-3 oil in the new perfusion emulsions comprises from about 10% to about 99% omega-3 diglyceride, omega-3 triglyceride or combinations thereof by weight per total weight of the omega-3 oil. However, this amount can vary widely. For Example the Tri-DHA emulsions administered in vivo in Example 3 had >90% of TG fatty acids as DHA. In certain embodiments the amount of TG or DG ranges from about 10% to about 20%, from 20% to about 40%, from 40% to about 60% and from 60-99%. About 20% to about 99% of the total acyl groups of the omega-3 of the diglycerides or triglycerides consist of EPA or DHA, and this can range from about 20% to 50%, from 50% to 75%, from 75% to 90%, from 90% to 97% of the total acyl groups of the omega-3 diglycerides or triglycerides consisting of EPA or DHA.

Omega-3 glyceride perfusion emulsions of the present invention may contain a stabilizing or isotonizing additive; usually glycerol is added. Preferred stabilizing or isotonizing additives include glycerol, sorbitol, xylitol or glucose. Glycerol is most preferred.

In addition to perfusion buffer, omega-3 glyceride perfusion emulsions may contain conventional auxiliary agents and/or additives, such as emulsifiers, emulsifying aids (co-emulsifiers), stabilizers, antioxidants, and isotonizing additives. Emulsifiers may include physiologically acceptable emulsifiers (surfactants) such as phospholipids of animal or vegetable origin. Examples of phospholipids are egg yolk lecithin, a biologic phospholipid, a phosphatidylcholine with fixed fatty acyl chain composition, a glycophospholipid or a phosphatidylethanolamine. Other lecithins, such as soy lecithin may be used. Particularly preferred are purified lecithins, especially soybean lecithin, egg lecithin, or fractions thereof, or the corresponding phosphatides. The emulsifier content may vary according to industry standards from about 0.02% to about 2.5%, or from about 0.6% to about 1.5% and most of about 1.2%, based on the total weight of the emulsion. In one embodiment the emulsifier is 1.2 mg of egg yolk lecithin/100 ml emulsion.

Alkali metal salts, such as sodium salts, of long chain, $C_{16}$ to $C_{28}$ fatty acids may also be used as emulsifying aids (co-emulsifiers). The co-emulsifiers are employed in concentrations of from about 0.005% to about 0.1%, or about 0.02% to about 0.04%, based on the total weight of emulsion. Further, cholesterol may be added in combination with other co-emulsifiers may be employed as an emulsifying aid in a concentration of from about 0.005% to about 0.1%, or from about 0.02% to about 0.04%, based on the total weight of emulsion.

Omega-3 glyceride perfusion emulsions may further comprise an effective amount of an antioxidant, such as vitamin E, in particular a-tocopherol (the most active isomer of vitamin E in humans) as well as gamma tocopherol, and/or ascorbyl palmitate as antioxidants and thus for protection from peroxide formation. The total amount of alpha tocopherol may be up to 1000 mg per liter. In a preferred embodiment the total amount of said antioxidant is from about 10 mg to about 1000 mg, more or from about 25 mg to about 1000 mg, or from about 100 mg to 500 mg, based on 100 g of lipid.

Preparation of the n-3 glyceride perfusion emulsions are known in the art. Omega-3 lipid-based perfusion emulsions according to the invention are oil-in-water (o/w) emulsions in which the outer continuous phase is the perfusion buffer purified or sterilized for use to store organs/tissues. Such n-3 glyceride perfusion emulsions may be obtained by standard methods, i.e. by mixing the oil components followed by emulsification and sterilization. The pH value of the lipid emulsion may be adjusted to a physiologically acceptable value, preferably to a pH of from about 6.0 to about 9.0, more preferably from about 6.5 to about 8.5. Auxiliary agents and additives may be added to the oil mixture prior to emulsification or prior to sterilization.

Omega-3 glyceride perfusion emulsions according to the invention can be prepared by known standard procedures.

Typically, first the lipids, emulsifier and other auxiliary agents and additives are mixed and then filled up with water with dispersing. The water may optionally contain additional water-soluble components (e.g. glycerol).

Lipid particles in the perfusion emulsions of the present invention may have a median particle size of less than 1 µm, more preferably 100 to 500 nm.

Examples below are perfusion buffers available currently that can be used in the n-3 glyceride perfusion emulsions of the present invention and related methods. Marketed Products:

AQIX® RS-I Solution™ (Aqix Ltd) AQIX® RS-I solution uniquely replicates the tissue fluid present in all human organs, without adding extracts of human or animal serum for donor organ transplantation perfusion. AQIX® RS-I is in pre-clinical development ahead of CE marking as a Class 3 medical device for use in the transport, storage and/or functional evaluation of organs prior to transplantation.

Machine Perfusion Solution-Belzer UW™ (Bridge to Life Ltd) Machine Perfusion Solution-Belzer UW® is intended for the in vitro flushing and temporary continuous machine perfusion preservation of explanted kidneys.

STEEN Solution™ (XVIVO Perfusion AB) The circuit perfusion of the lung mimics in-vivo conditions; the ventilated lung is perfused with a 15% deoxygenated suspension of red cells in STEEN Solution™ and the critical parameters of gaseous exchange, pulmonary vascular resistance and other key variables under normothermic conditions are monitored.

Liver Perfusion Medium™ (Life Technologies Corporation) Liver Perfusion Medium is a buffered, balanced salt solution formulated to cleanse the liver of blood, prevent clotting, and initiate loosening of cell-to-cell contact.

Other perfusion/reperfusion solutions are described in: 20090311663; U.S. Pat. Nos. 4,879,283 and 4,798,824. These patents cover the widely used organ preservation solution commercially available under the trade name VIASPAN™ marketed by Barr Laboratories.

Additionally, other agents that assist in conserving and preparing an organ or tissue for transplant may be added to an n-3 glyceride perfusion/reperfusion emulsion of the present invention such as any one or more of the following agents: antibiotics, VEGF, KGF, FGF, PDGF, TGF, IGF-1, IGF-2, IL-1, prothymosin and/or thymosin 1 in an effective amount. Other buffers include:

Phosphate-Buffered Sucrose Solution

This solution contains sucrose 140 mmol/L and sodium hydrogen and dihydrogen phosphate as buffers. In experimental studies, it preserved dog kidneys for 3 days. It is not commonly used today.

University of Wisconsin Solution

University of Wisconsin (UW) solution was developed for liver, kidney, and pancreas preservation. It has been considered the standard for renal and hepatic preservation, effectively extending the ischemic time for kidneys and livers and allowing them to be transported considerable distances to waiting recipients. UW solution has also been successfully applied to small-bowel and heart preservation. The composition of the solution is complex. Analysis of its various components has shown that some may be omitted or replaced with results similar to that of the original solution. The solution has an osmolality of 320 mmol/kg and pH 7.4 at room temperature and is composed of the following:
Potassium 135 mmol/L
Sodium 35 mmol/L
Magnesium 5 mmol/L
Lactobionate 100 mmol/L
Phosphate 25 mmol/L
Sulphate 5 mmol/L
Raffinose 30 mmol/L
Adenosine 5 mmol/L
Allopurinol 1 mmol/L
Glutathione 3 mmol/L
Insulin 100 U/L
Dexamethasone 8 mg/L
Hydroxyethyl starch (HES) 50 g/L
Bactrim 0.5 ml/LHES conveys no advantage to the solution when used for cold storage, and it, in fact, adds to the viscosity of the solution as well as to the expense. HES-free derivatives of the solution have given similar, if not better, clinical results than those of the original formulation. The lactobionate is the major effective component of the solution. Its insoluble nature maintains the colloid oncotic pressure of the solution, delaying or preventing equilibration of the solution across the cell membrane, and thus delaying the development of cellular edema. The lowered concentration of potassium improves the flushing efficiency of the solution by removing the vasoconstrictive effect of the high potassium solution. Glutathione is unstable in solution and effective as an oxygen free-radical scavenger only if it is added immediately before use. Adenosine and allopurinol help in this function.

Celsior Solution

Celsior is a recently developed extracellular-type, low-viscosity (due to the absence of HES) preservation solution that couples the impermeant, inert osmotic carrier from UW solution (by using lactobionate and mannitol) and the strong buffer from Bretschneider HTK solution (by using histidine). The reduced glutathione in Celsior solution is the best antioxidant available. The solution was specifically designed for heart transplantation. It is being currently used in clinical lung, liver, and kidney transplantations and it is under investigation for pancreas transplantation.

The contents of Celsior solution are as follows:
Sodium 100 mmol/L
Potassium 15 mmol/L
Magnesium 13 mmol/L
Calcium 0.25 mmol/L
Lactobionate 80 mmol/L
Glutathione 3 mmol/L
Glutamate 20 mmol/L
Mannitol 60 mmol/L
Histidine 30 mmol/L Kyoto ET Solution Researchers at Kyoto University developed a new solution that contains a high sodium concentration, a low potassium concentration, trehalose, and gluconate. The solution is chemically stable at room temperature. It is being investigated for skin storage and lung preservation in a rat model. ET Kyoto solution is also being actively investigated in clinical trials for transplantation of the lungs, heart, and other organs.

Its constituents include the following:
Sodium 100 mmol/L
Potassium 44 mmol/L
Phosphate 25 mmol/L
Trehalose 41 mmol/L
HES 30 gm/L
Gluconate 100 mmol/L

8. EXAMPLES

Example 1: Materials and Methods

All research studies were carried out according to protocols approved by the Columbia University Institutional Animal Care and Use Committee (IACUC) and in accordance with the Association for Assessment and Accreditation of Laboratory Animal Care guidelines.

General Method of Preparation of a Diglyceride (DG) and Triglyceride (TG) Emulsions.

Phospholipid-stabilized emulsions of n-3 (DG and/or TG) are typically prepared with fish oil DG and/or TG (synthetic oils can also be used), and egg yolk phospholipid. In an embodiment the amount of n-3 oil in the perfusion emulsions is as low as 0.05%.

Each emulsion contained the desired amount of n-3 oil, a diglyceride or a triglyceride, which is typically emulsified by 1.2 g of egg yolk lecithin, and 2.5 g of glycerol/100 mL water. The emulsion lipids are mixed in doubly distilled water (30 g of water) and dispersed by means of an Ultra-Turrax (Janke and Kunkel K G, Staufen, West Germany) for 10 min; water is added to give a final volume of 100 mL, and emulsions are dispersed for an additional 10 min. Subsequently, the dispersion is homogenized by ultrasound in a cooling cell with a Labsonic 2000 homogenizer for 10 min at an energy input of 200 W. The emulsions are then sealed in 5 mL vials under N2, and thereafter kept at 4° C. in some processes for industrial production emulsion volumes of up to 3-500 ml may be made. Mean particle sizes are determined by laser spectroscopy, and are similar in both size and homogeneity with mean diameters between 290 and 300 nm. If the emulsions obtained still contain lipid particles having a diameter that is too large, the average droplet sizes of emulsions may be further reduced by additional homogenization, e.g., by using a high-pressure homogenizer.

Animal Care

All studies in heart were performed with the approval of the Institutional Animal Care and Use Committee at Columbia University, and New York University School of Medicine, and conform to the *Guide for the Care and Use of Laboratory Animals* published by the US National Institutes of Health (NIH Pub. No. 85-23, 1996). C57BL6 mice (weight between 25-30 g and 12-14 weeks old) were obtained from Jackson Laboratories for our studies. Mice were kept in an animal care facility for a week prior to the studies. All mice were fed a normal chow diet (Teklad Global diets, Harlan Laboratories).

Reagents

The primary antibodies used were Bcl-2, Beclin-1, PPAR-γ, p-AKT, total-AKT, p-GSK-3β, total-GSK-3β (Cell Signaling, USA); and β-actin (BD Biosciences Pharmingen, USA). The secondary antibodies used were anti-rabbit IRdye800, anti-mouse IRdye700 (1:50,000 dilution). SB216763 (3 µM), Rosiglitazone (6 mg/kg body weight) were purchased from Sigma-Aldrich, USA. Phosphatidylinositol 3-kinase (PI3K)/AKT inhibitor LY-294002 (10 µM) was purchased from Calbiochem. The doses of the inhibitors and agonist used in this study were based on publications in the literature.[1] n-3 fish oil-based emulsion (10 g of TG/100 mL) was commercially prepared intravenous phospholipid-stabilized emulsions, and contained high concentrations of n-3 FA as previously described[2,3] n-3 TG emulsion was rich in EPA (up to 28%) and DHA (up to 30%).

Example 2: Ex Vivo Ischemia and Reperfusion with n-3 Glyceride Perfusion Emulsion A. Materials and Methods Experiments were carried out and modified for use in mice hearts.[1,2] C57BL6 mice weighting between 25-30 g and 12-14 weeks old were anesthetized by injecting ketamine/xylazine cocktail [80 mg/kg and 10 mg/kg respectively]. The hearts were rapidly excised and then were retrograde perfused through the aorta in a non-recirculating mode, using an isovolumic perfusion system through Langendorff technique (LT), with Krebs-Henseleit buffer, containing (in mM) the following: 118 NaCl, 4.7 KCl, 2.5 $CaCl_2$, 1.2 $MgCl_2$, 25 $NaHCO_3$, 5 Glucose, 0.4 Palmitate, 0.4 BSA, and 70 mU/l insulin. Perfusion $pO_2$>600 mmHg was maintained in the oxygenation chamber.

Evidence supporting the methods and products of the invention has been established in an ex vivo model using hearts rapidly removed from ketamine/xylazine anesthetized 12-14 weeks old C57BL/6 mice weighing between 25-30 g that were retrograde perfused in a non-recirculating mode, using an isovolumic perfusion system through the well-known Langendorf System (FIG. 1). In this system isolated mouse hearts were initially perfused with a perfusion buffer containing KREB's solution containing (in mM) the following: 118 NaCl, 4.7 KCl, 2.5 $CaCl_2$, 1.2 $MgCl_2$, 25 $NaHCO_3$, 5 Glucose, 0.4 Palmitate, 0.4 BSA, and 70 mU/l insulin. Perfusion $pO_2$ at a pressure greater than 600 mmHg and a flow speed of 2.5 ml/min was maintained in the oxygenation chamber. The experimental plan included an equilibration baseline period of 30 min normoxic perfusion followed by 30 min global zero-flow ischemia (induced ischemia) and 60 min of reperfusion. The flow rate was 2.5 ml/min. The perfusion apparatus was tightly temperature controlled for maintaining heart temperatures at 37+/−0.1° C. under all conditions. Baseline measurements were taken after 30 minutes of perfusion with the KREB's solution.

After the induced ischemia, control hearts were reperfused using the same Kreb's buffer. Test hearts were reperfused in Kreb's buffer plus 0.3% n-3 TG oil. The test omega-3 (n-3) triglyceride perfusion emulsion used to reperfuse test hearts was prepared using standard industry methods for the production of the therapeutic emulsions in water. A 10% omega-3 triglyceride emulsion was obtained containing 10 ml n-3 triglyceride (TG) that contained 48% fatty acids as EPA or DHA per 100 ml water. This 10% TG emulsion was emulsified by egg yolk lecithin, 1.2 g/100 ml. TG fatty acid (FA) composition (by weight) of the emulsion used in experiments 1-9 was as determined by gas liquid chromatography and was as follows for the n-3 emulsion: C14:0, 5.4%; C16:0, 14.8%; C16:1, 8.4%; C18:0, 2.8%; C18:1, 12.7%; C18:2 (n-6), 2.6%; C18:3 (n-3), 0.8%; C20:1, 1.2%; C20:4 (n-6), 1.9%; C20:5 (EPA, n-3), 18.3%; C22:1, 0.2%; C22:4, 0.6%; C22:5, 2.6%; and C22:6 (DPA, n-3), 27.7. To make the test emulsion that was used to reperfuse the isolated hearts after the induced ischemia, 300 mg 10% n-3 TG emulsion was diluted in 100 ml Kreb's perfusion buffer to make a 0.3% n-3 TG perfusion emulsion, referred to in the summary of results as the test n-3 triglyceride reperfusion emulsion. The methods of the present invention use the n-3 glyceride perfusion emulsions of the invention that have from about 0.05% n-3 glyceride up to less than 7% n-3 glyceride.

Left Ventricular Developed Pressure (LVDP)

Left ventricular developed pressure (LVDP) was continuously monitored using a latex balloon placed on the left ventricle and connected to a pressure transducer (Gould Laboratories; Pasadena, Calif.). Cardiac function measurements were recorded on a 2-channel ADI recorder. A catheter inserted in the left ventricle of the isolated heart was used to measure left ventricular developed pressure (LVDP) as well as cardiac rhythm in the ex vivo reperfusion experiments described.

Assay of Lactate Dehydrogenase (LDH)

Myocardial injury was assessed by measuring the release of lactate dehydrogenase (LDH) from the effluent in the ex vivo I/R system and from blood samples in the in vivo LAD system, using the commercially available enzymatic kits (Pointe Scientific, INC, MI USA) as published earlier.[1,2]

Western Blot Analysis

The tissue and cell protein concentration was determined using a DC Protein Assay kit (Bio-Rad). Equal amounts of protein were separated by SDS-PAGE (4-12% gradient gels), and proteins were loaded to a nitrocellulose membrane (Invitrogen). After blocking nonspecific binding with the Odyssey blocking buffer (Li-Cor Biosciences), membranes were incubated overnight at 4° C. with target primary antibodies (1:1,000 dilution), according to the manufacturer's instructions. Successively, membranes were incubated with infrared labeled secondary antibodies for 1 h at room temperature. The bound complex was visualized using the Odyssey Infrared Imaging System (Li-Cor; Lincoln, Nebr.). The images were analyzed using the Odyssey Application Software, version 1.2 (Li-Cor) to obtain the integrated intensities.

Statistical Analysis

Data were expressed as the mean±SD. For assessing the difference between values. the Student's t test was used. A value of $p<0.05$ was considered statistically significant.

Figure 24:
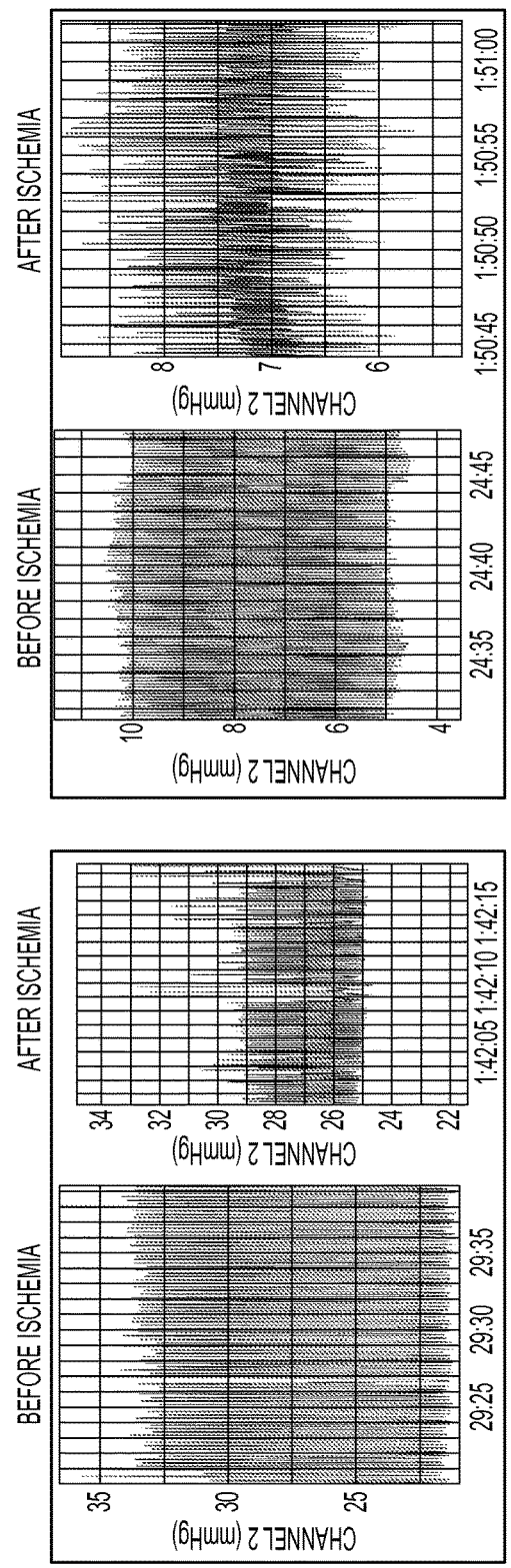
FIG. 24 are LVDP graphs of marked increases of arrhythmias after ischemia observed in the Langendorff system by pressure recording in control hearts perfused and reperfused with their "basic" buffer. Results are shown for 2 different representative hearts.
Figure 25:
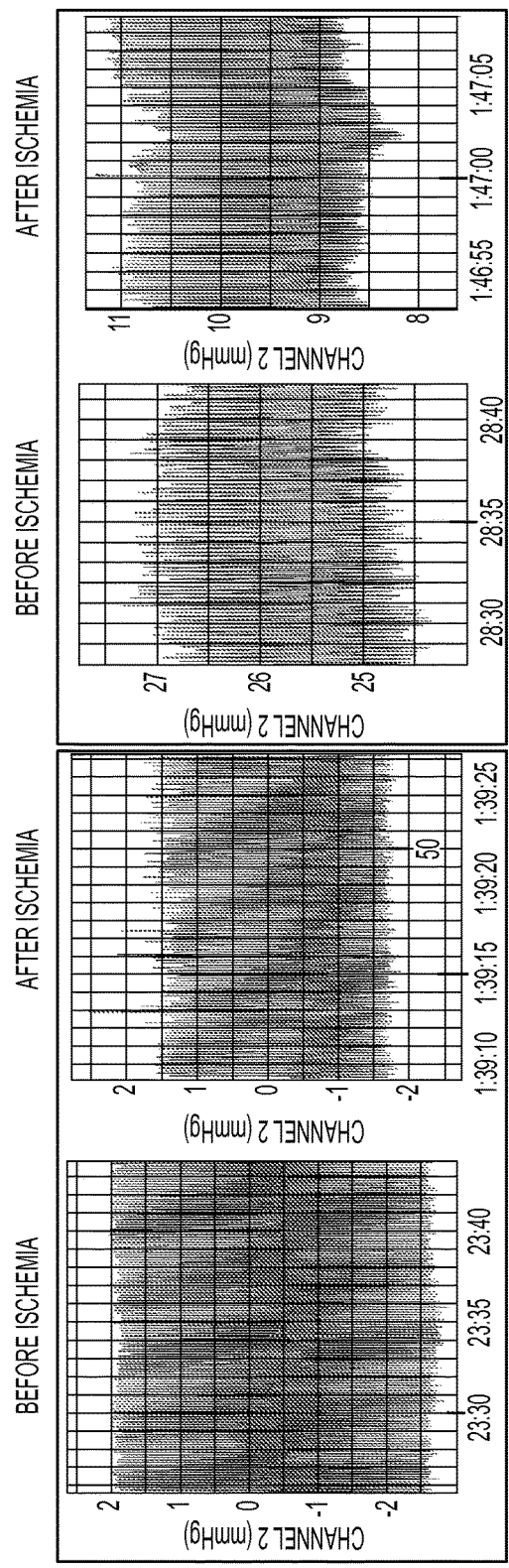
FIG. 25 are LVDP graphs in the Langendorff system for n-3 TG treated hearts showing a normal heart rate, normal LVDP, and very few arrhythmias compared to the control hearts in FIG. 24. Results are shown for 2 different representative hearts.

B. Results of Reperfusion of Isolated Hearts Ex Vivo with n-3 Glyceride Emulsion Reduces Reperfusion Injury after an Ischemic Event After 1 hour of reperfusion following induced ischemia, the heart rate and LVDP were markedly decreased, and arrhythmias were observed by pressure recording in control hearts. FIG. 24. By contrast test hearts reperfused with the above-described n-3 triglyceride perfusion emulsion maintained a normal heart rate, normal LVDP, and no or very few arrhythmias. FIG. 25.

Figure 3:
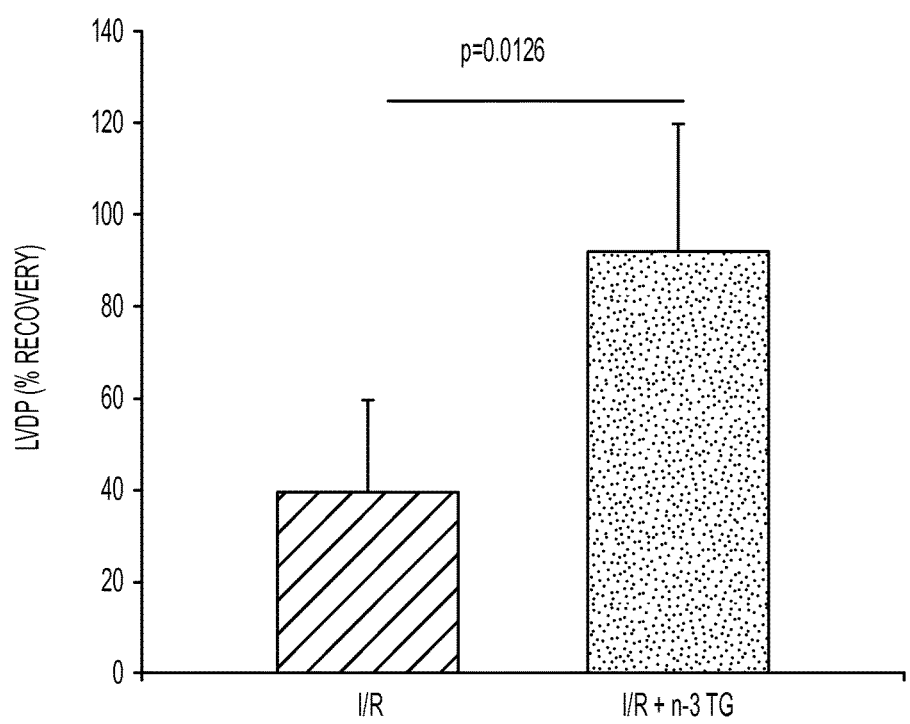
FIG. 3 is a bar graph that illustrates LVDP recovery vs. baseline further showing that test reperfusion emulsion with n-3 TG resulted in almost 100% recovery vs. control reperfusion buffer without n-3 TG~40%.
Figure 5:
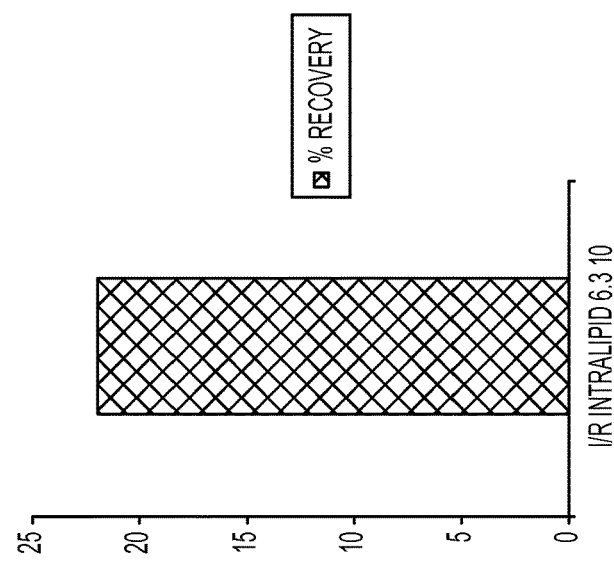
FIG. 5 is a bar graph that illustrates infusion of an n-6 triglyceride emulsion Intralipid,™ decreased recovery after ischemia from 40% to only 22%. This suggests that n-6 glycerides may actually have adverse effects on cardiac tissue recovery after ischemia.
Figure 4:
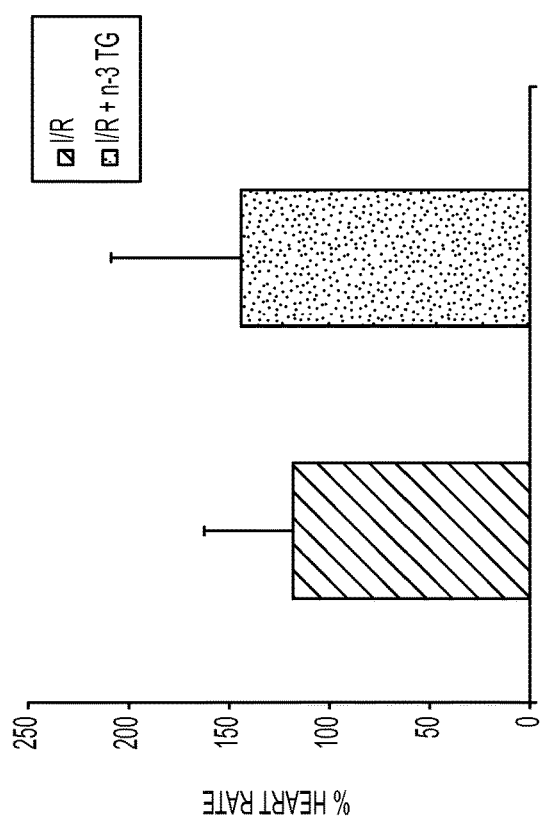
FIG. 4 is a bar graph that illustrates an increase in % heart rate after n-3 TG emulsion administration.

Specifically, after 1 hour of reperfusion with the n-3 triglyceride emulsion, there was over a 90% recovery of LVDP compared to only a 40% LVDP recovery in the control heart. FIG. 3. Heart rate recovery was also improved with reperfusion in the n-3 triglyceride emulsion. In a separate experiment, a 0.3% perfusion emulsion comprising the n-6 TG Intralipid™ was tested. FIG. 5.

Figure 6:
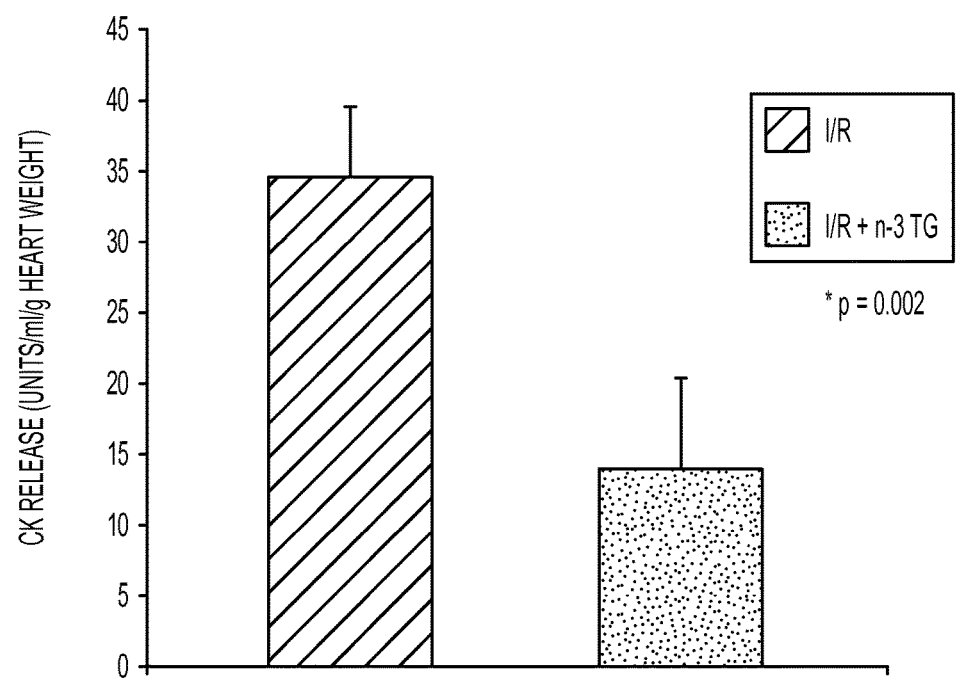
FIG. 6 is a bar graph that illustrates n-3 TG markedly decreased creatine kinase levels in the perfusion solution, a measure of heart tissue injury, after ischemia.

Myocardial tissue injury was also assessed by measuring the release of lactate dehydrogenase (LDH) from the effluent in the ex vivo I/R system and from blood samples in the in vivo left anterior descending coronary artery ligation model system (LAD), using the commercially available enzymatic kits (Pointe Scientific, INC, MI USA) as published earlier. Creatine kinase which is an additional marker of myocardial infarction was markedly decreased in isolated hearts that were reperfused in the test n-3 triglyceride emulsion (FIG. 6). To determine if n-3 TG protects hearts by modulating changes in key signaling pathways linked to I/R injury, p-AKT, pGSK-3β, and Bcl-2 were probed in myocardial tissue by western blotting.

Figure 10A:
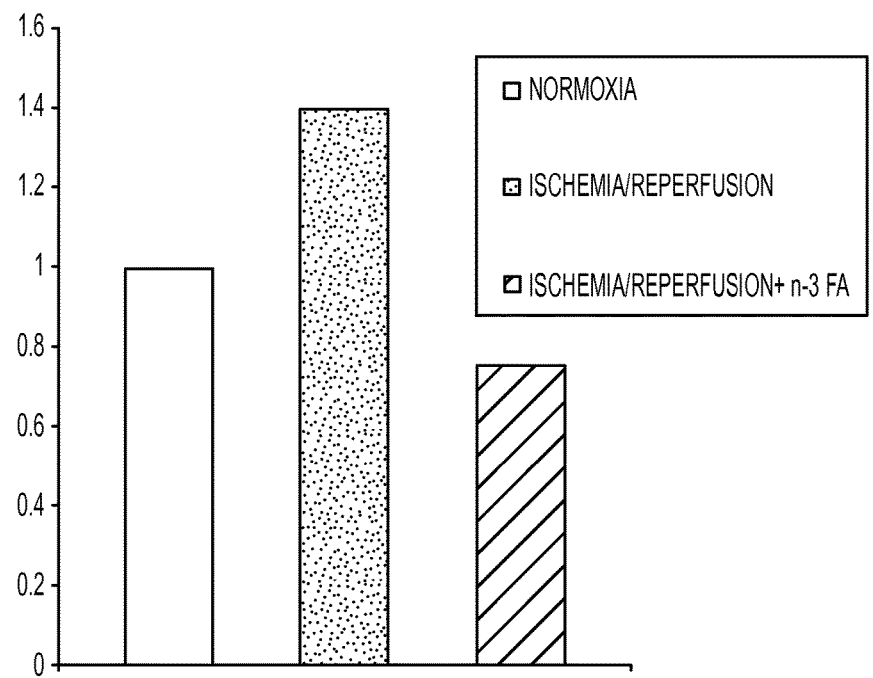
FIG. 10A-10B show that PPARγ protein expression increase after I/R (ischemia after the initial baseline perfusion followed by reperfusion in Control buffer) but decreased by inclusion of n-3 TG in the reperfusate as shown in the bar graph represented by FIG. 10A.
Figure 10B:
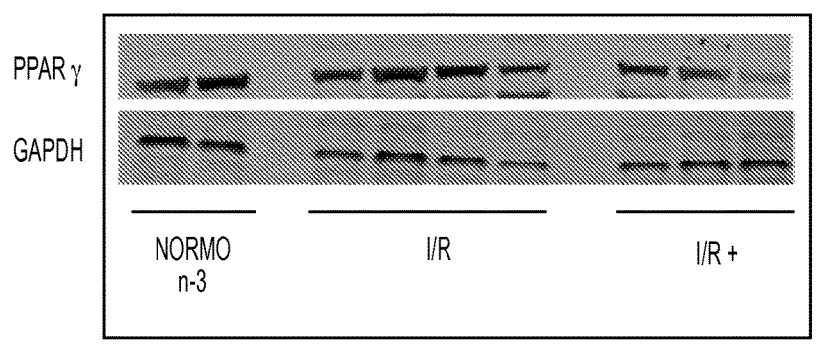

Since Bcl-2 interacts with Beclin-1, and influences autophagy, as shown in FIG. 14A-14C, n-3 TG treated hearts showed a significant reduction in Beclin-1 protein expression, with concomitant increase of Bcl-2 protein expression. Further, the level of the anti-apoptotic gene marker Bcl-2 and expression of Bcl-2 mRNA were also increased in test n-3 emulsion-reperfused hearts compared to control hearts (FIG. 7A-7B). Next, hypoxia-inducible factor 1 (HIF-1), which is a key mediator of adaptive responses to decreased oxygen availability in ischemia, was examined. HIF-1 protein expression (FIG. 15A-15C) increased rapidly after ischemia. Another positive result showed that the level of protein and mRNA for HIF-1, a marker for autophagy which may increase cell death, were down-regulated after test hearts were reperfused with the n-3 triglyceride emulsion, compared to controls (FIG. 8A-8C). Another autophagic marker, Beclin 1, was also decreased in terms of protein expression and mRNA expression after reperfusion with buffer containing n-3 triglycerides (FIG. 9A-8C). Finally, Western blot analysis showed that PPAR gamma protein expression, associated with pro-inflammatory responses in heart, was markedly increased after reperfusion in control hearts but decreased in test hearts that were reperfused in n-3 emulsion (FIG. 15A) (FIG. 10A-10B).

The above findings tested in isolated, living, intact mammalian heart ex vivo, show that including n-3 glycerides in a perfusion (or reperfusion) buffer for donor organs significantly preserved healthy function as indicated by a decrease in creatine kinase, and upregulation of beneficial proteins including the anti-apoptotic gene marker Bcl-2. N-3 glycerides further resulted in downregulation of potentially harmful proteins including HIF1 (a marker for autophagy which may increase cell death), PPAR gamma (associated with some pro-inflammatory responses in heart), and beclin 1 (an autophagic marker).

Although only a 0.3% n-3 triglyceride perfusion emulsion was tested ex vivo using the Langendorf system, the n-3 glyceride perfusion emulsions can have higher amounts of up to but less than 7% n-3 oil, preferably 0.5-1%, 1-2%, 2-5% or 5-7%, and they can have n-3 triglyceride, n-3 diglyceride and combinations thereof. In previous studies for which some of the results are included in Examples 4 and 5, it was shown that n-3-TG and n-3-DG-emulsions were very effective in reducing or preventing reperfusion damage in vivo after hypoxia/ischemia. See also Deckelbaum, U.S. Ser. No. 11/558,568 and U.S. Ser. No. 13/336,290; U.S. Ser. Nos. 61/767,248, 12/441,795 (U.S. Pat. No. 8,410,181), Ser. Nos. 13/783,779, 13/953,718, and 14/102,145. Thus it is expected that n-3 glyceride perfusion emulsions of the present invention can be made using the n-3 DG and TG formulations that were administered in vivo.

Figure 12B:
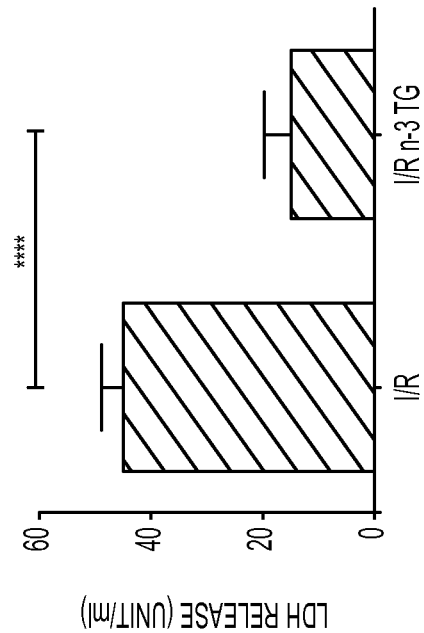
FIG. 12A-12B shows the effect of n-3 TG emulsion on an ex vivo ischemia/reperfusion model.
Figure 12A:
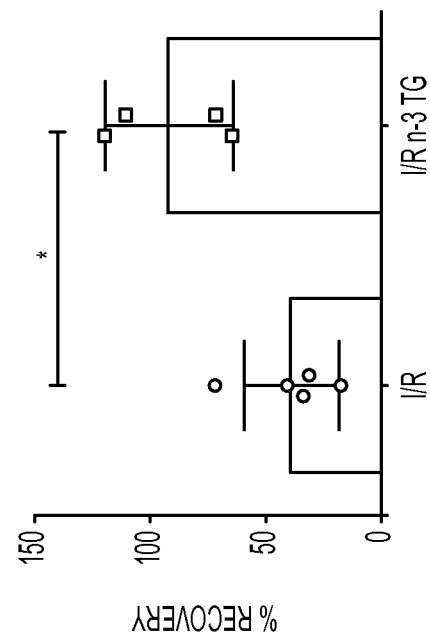

Acute intervention (reperfusion) with 0.3% n-3 TG perfusion emulsion in the ex vivo perfused heart (I/R model) after induced ischemia showed that including n-3 TG significantly improved LVDP recovery after I/R (FIG. 12A), compared to control hearts. Reperfusion of the heart with KREB'S buffer+n-3 TG maintained normal rhythm and LVDP was nearly restored to 100% similar to pre-ischemia time. During reperfusion period, heart perfusates were collected to detect LDH release, as markers of ischemic injury. LDH release appeared significant different between n-3 TG treated and control hearts, showing that acute n-3 TG treatment exhibits a protective role (FIG. 12B).

Figure 13B:
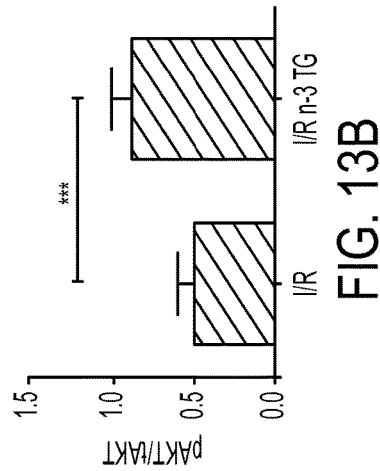
FIGS. 13A-13C illustrate signaling pathways.
Figure 13C:
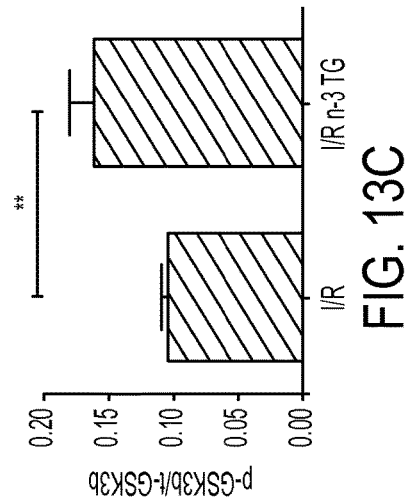
Figure 13A:
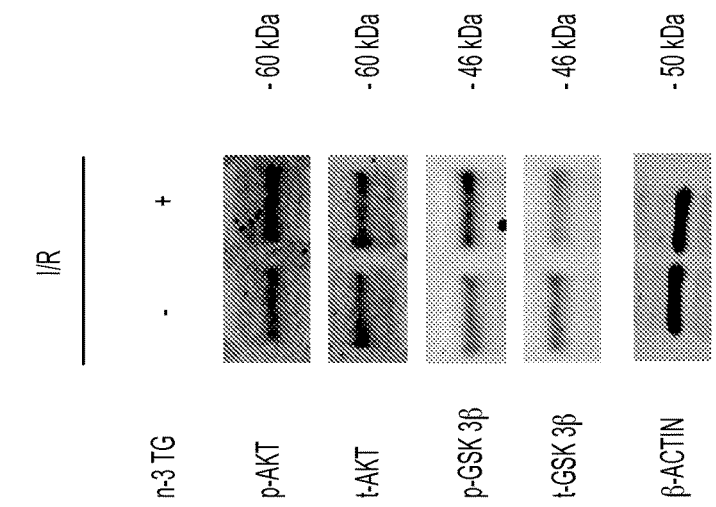
Figures 16A, 16B:
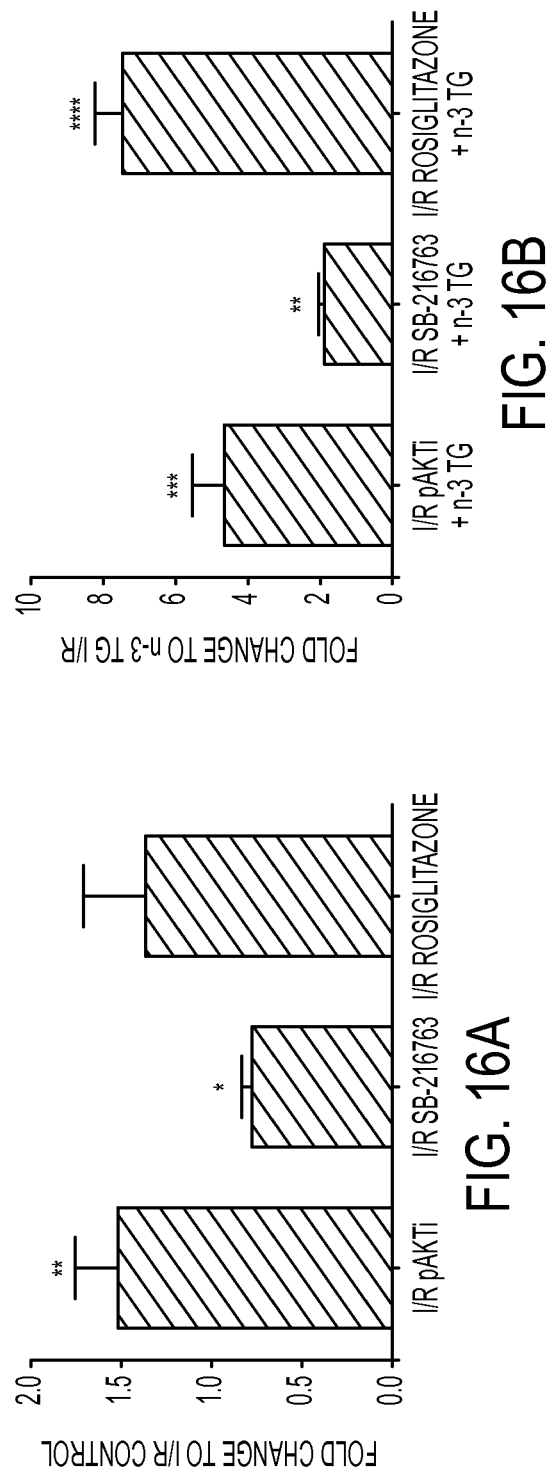
FIGS. 16A-16B are bar graphs that show release of the injury marker LDH.

To determine if n-3 TG protects hearts by modulating changes in key signalling pathways linked to I/R injury, p-AKT, p-GSK-3β, and Bcl-2 were probed after induced ischemia Reperfusion with 0.3% n-3 triglyceride perfusion emulsion (0.3% n-3 TG) significantly increased phosphorylation of AKT and GSK3β (FIG. 13A-13C), and Bcl-2 protein expression (FIG. 14A-14C), indicating that n-3 TG reduced apoptosis by activating the PI3K-AKT-GSK3β signalling pathway and anti-apoptotic protein Bcl-2. Since Bcl-2 interacts with Beclin-1[3,4] and influences autophagy, as shown in FIG. 14A-14C, the expression of Beclin-1 increased after ischemia/reperfusion condition; 0.3% n-3 TG treated hearts showed a significant reduction in Beclin-1 protein expression, with concomitant increase of Bcl-2 protein expression as we mentioned above. To establish the link between n-3 TG and PI3K/AKT and GSK3β pathways in I/R injury, hearts were treated with GSK-3β inhibitor SB216763 (3 μM) or Phosphatidylinositol 3-kinase (PI3K)/AKT inhibitor LY-294002 (10 μM); each of them was added at the beginning of the baseline period and continued throughout ischemia and reperfusion. The doses of the inhibitors used in this study were based on publications in the literature[1]. LDH release was significantly reduced by 0.3% n-3 TG, and the protection thus afforded was abrogated by the PI3K/AKT inhibitor, LY-294002 (FIG. 16A-16B). Treatment with SB-216763 plus 0.3% n-3 TG emulsion significantly inhibited LDH release compared to I/R control hearts (FIG. 16A-16B).

Next, hypoxia-inducible factor 1 (HIF-1) was investigated, which is a key mediator of adaptive responses to decreased oxygen availability in ischemia. HIF-1α protein expression (FIG. 15A-15C) increased rapidly after ischemia. Inclusion of 0.3% n-3 TG in perfusion buffer during reperfusion significantly inhibited the protein expression of HIF-1α. Previous studies showed that n-3 fatty acids, in contrast to saturated fatty acids, are able to lower macrophages and arterial endothelial lipase and inflammatory markers and these effects are linked to PPAR-γ[5]. Accordingly, the potential association of PPAR-γ and n-3 TG acute treatment in I/R condition was examined. Western blot analysis showed that in n0.3% n-3 TG reperfused hearts protein expression of PPAR-γ was significantly lower compared to the control hearts (FIG. 15A-15C).

In order to establish the link between PPAR-γ and n-3 TG effect, mice were treated with Rosiglitazone (6 mg/kg body weight, IP injection), a common agonist of PPAR-γ, 30 min before I/R injury in the isolated perfused hearts. These hearts were perfused with Krebs-Henseleit buffer without or with n-3 TG emulsion during reperfusion time. LDH release was significantly higher in Rosiglitazone plus n-3 TG treated hearts vs Rosiglitazone treated hearts (FIG. 16A-16B). These data indicate that PPAR-γ reduction is linked to cardioprotection afforded by n-3 TG during I/R.

Taken together, these results show that PI3K/AKT, GSK-3β and PPAR-γ are pathways modulating n-3 TG cardioprotection.

REFERENCES CITED FROM EXAMPLE 2

1. Ananthakrishnan, R., et al., Aldose reductase mediates myocardial ischemic-reperfusion injury in part by opening mitochondrial permeability transition pore. Am J Physiol Heart Circ Physiol, 2009. 296(2): p. H333-41.
2. Hwang, Y. C., et al., Central role for aldose reductase pathway in myocardial ischemic injury. FASEB J, 2004. 18(11): p. 1192-9.
3. Griendling K K, and FitzGeral G A. (2003) Oxidative stress and cardiovascular injury: part I: Basic mechanisms and in vivo monitoring of ROS. Circulation, 108, 1912-1916.
4. Marczin N, El-Habashi N, Hoare G S, Bundy R E, and Yacoub M. (2003) Antioxidants in myocardial ischemia-reperfusion injury: Therapeutic potential and basic mechanisms. Archives of Biochemistry and Biophysics, 420, 222-236.
5. Deckelbaum R J, Torrejon C. (2012) The omega-3 fatty acid nutritional landscape: health benefits and sources. J Nutr.

Example 3: In Vivo Administration of Omega-3 Triglyceride DHA Emulsions Reduced Post Hypoxia-Ischemia Cardiac and Cerebral Reperfusion Injury A. Materials and Methods
Lipid Emulsion
Four different types of lipid emulsions were tested. Omega-3 (n-3) triglyceride fish oil-based and omega-6 (n-6) soy oil-based emulsions were commercially prepared intravenous phospholipid-stabilized emulsions. The omega-3 triglyceride contained high concentrations of n-3 fatty acids (FA) as described.[1, 2] (See Table 1.) These omega-3 triglyceride emulsions, referred to as "n-3 TG," have 10% omega-3 fish oil (n-3) having less than 10% omega-6 oil by weight in grams per 100 ml of emulsion, wherein the omega-3 oil is >90% triglyceride (TG) by weight per total weight of the omega-3 oil, and in which up to about 30% % of the total acyl groups are DHA and up to about 28% % are EPA. The n-3 TG emulsions are also called "TG90-DHA30." Other emulsions having pure (99%) DHA or pure (99%) EPA was also tested as described. For doses of injected n-3 TG emulsions, an amount was calculated to achieve an administration containing 50% of the total TG-FA as DHA and EPA (Table 1). Thus, 1 gm of TG emulsions is expressed as 0.5 gm n-3 TG.

The n-6 TG emulsions, referred to in the experiments in Example 3, comprise 20% omega-6 oil (n-6) by weight in grams per 100 ml of emulsion, 0% DHA, 0% EPA and 55% TG from linoleic acid (Table 1). These n-6 TG emulsions were produced from soy bean oil rich in n-6 FA: linoleic acid constituting about 55% of total FA.

TABLE 1

Fatty Acid Composition of Lipid Emulsions[1]

| Source | n-3 TG (g/100 ml) [herein "n-3 TG90-DHA30"] g/100 mL | n-6 TG (g/100 ml) g/100 mL |
|---|---|---|
| Soybean oil | — | 20 |
| Fish oil | 10 | — |
| Egg phosphatidylcholine | 1.2 | 1.2 |
| Glycerol | 2.5 | 2.25 |
| FA (% of total FA by weight) | % | % |
| Palmitic acid (C16:0) | 2.5-10 | 7-14 |
| Stearic acid (C18:0) | 0.5-2 | 1.4-5.5 |
| Oleic acid (C18:1n-9) | 6-13 | 19-30 |
| Linoleic acid (C18:2n-6) | 1-7 | 44-62 |
| Arachidonic acid (C20:4n-6) | 1-4 | <0.5 |
| α-linolenic acid (C18:3n-3) | 2 | 4-11 |
| Eicosapentaenoic acid (C22:6n-3) | 12.5-28.2 | — |
| Docosahexaenoic acid (C22:6n-3) | 14.4-30.9 | — |

[1]Data provided by Fresenius Kabi AG; FA, Fatty acids.

Pure Tri-DHA (99% DHA) and Tri-EPA (99% EPA) emulsions were also made; they were VLDL-sized and laboratory-made with TG oil and egg yolk phospholipid using sonication and centrifugation procedures that are known in the art.[3, 4] Briefly, 200 mg of triglyceride-DHA oil>99% or Tri-EPA oil>99% was mixed with a 5:1 weight ratio of egg yolk phosphatidylcholine (40 mg). The mixture was fully evaporated under $N_2$ gas, and was further desiccated under vacuum overnight at 4° C. The dried lipids were resuspended in 1 mL of lipoprotein-free buffer (LPB) (150 mmol/L NaCl, 0.5 ml of 0.1% glycerol and 0.24 mmol/L EDTA, pH 8.4, density 1.006 g/mL) at 60° C. with added sucrose (100 mg/1 mL LPB) to remove excess phospholipid liposomes. The lipid emulsions were then sonicated for 1 hr at 50° C., 140 W under a stream of $N_2$ using a Branson Sonifier model 450 (Branson Scientific, Melville, N.Y.). After sonication, the solution was dialyzed in LPB for 24 hr at 4° C. to remove sucrose. The final emulsions comprising VLDL-sized particles were analyzed for the amount of TG and PL by enzymatic procedure using GPO-HMMPS, glycerol blanking method (Wako Chemicals USA, Inc., Richmond, Va.) and choline oxidase-DAOS method (Wako Chemicals USA, Inc., Richmond, Va.). The TG: phospholipid mass ratio was 5.0±1.0:1 similar to that of VLDL-sized particles. The emulsions were then stored under argon at 4° C. and were used within 2 weeks of preparation.

A specific example is of Tri-DHA was tested: "TG90-DHA30" that was administered in vivo following H/I to reduce reperfusion injury. Tri-DHA and Tri-EPA were purchased from Nu-Chek Prep, Inc. (Elysian, Minn.). Egg yolk phosphatidylcholine was obtained from Avanti Polar-Lipids, Inc. (Alabaster, Ala.).

B. Cardiac Reperfusion Injury is Reduced by Administration of n-3 Triglycerides

In Vivo Left Anterior Descending Coronary Artery (LAD) Occlusion

In vivo murine model of ischemia-reperfusion injury: Prior to surgery, mice were anesthetized with isoflurane inhalation (4% induction followed by 1-2.5% maintenance). Subsequent to anaesthesia, mice were orally intubated with polyethylene-60 (PE-60) tubing, connected to a mouse ventilator (MiniVent Type 845, Hugo-Sachs Elektronik) set at a tidal volume of 240 µL and a rate of 110 breaths per minute, and supplemented with oxygen. Body temperature was maintained at 37° C. A median sternotomy was performed, and the proximal left coronary artery (LAD) was visualized and ligated with 7-0 silk suture mounted on a tapered needle (BV-1, Ethicon). After 30 min of ischemia, the prolene suture was cut and the LAD blood flow was restored. Immediately after, intraperitoneal (IP) injection of n-3 TG emulsion (1.5 g/kg body weight) was performed and the second injection was done after 60 min of reperfusion. Control animals received IP injection of saline solution following the same time course. The chest wall was closed, and mice were treated with buprenorphine and allowed to recover in a temperature-controlled area[4,5].

Echocardiogram

In vivo transthoracic echocardiography was performed using a Visual Sonics Vevo 2100 ultrasound biomicroscopy system. This high-frequency (40 MHz) ultrasound system has an axial resolution of ~30-40 microns and a temporal resolution of >100 Hz. Baseline echocardiography images was obtained prior to myocardial ischemia and post-ischemic images were obtained after 48 hours of reperfusion. The mice were lightly anesthetized with isoflurane (1.5-2.0 L/min) in 100% $O_2$ and in vivo transthoracic echocardiography of the left ventricle (LV) using a MS-400 38-MHz microscan transducer was used to obtain high resolution two dimensional mode images. Images were used to measure LV end-diastolic diameter (LVEDD), LV end-systolic diameter (LVESD), LV ejection fraction (EF) and LV fractional shortening (FS) as published earlier[4,5].

Infarct Size Measurement

Myocardial infarct size determination: At 48 h of reperfusion mice were re-anesthetized, intubated, and ventilated using a mouse ventilator. A catheter (PE-10 tubing) was placed in the common carotid artery to allow for Evans blue dye injection. A median sternotomy was performed and the LAD was re-ligated in the same location as before. Evans blue dye (1.25 ml of a 7.0% solution) was injected via the carotid artery catheter into the heart to delineate the non-ischemic zone from the ischemic zone. The heart was then rapidly excised and fixed in 1.5% agarose. After the gel solidified, the heart was sectioned perpendicular to the long axis in 1-mm sections using a tissue chopper. The 1-mm sections was placed in individual wells of a six-well cell culture plate and counterstained with 1% TTC for 4 min at 37° C. to demarcate the nonviable myocardium. Each of the 1 mm thick myocardial slices was imaged and weighed. Images were captured using a Q-Capture digital camera connected to a computer. Images were analysed using computer-assisted planimetry with NIH Image 1.63 software to measure the areas of infarction and total risk area[4,5].

C. Results of 3 TG Administration Reduces Infarct Size and Improved Cardiac Function in LAD Model.

To test the effect of acute n-3 TO administration in myocardial ischemic injury, mice were subjected to 30 min of ischemia induced by LAD occlusion; coronary flow was then restored and myocardial functional recovery during reperfusion was assessed. IP injection of n-3 TG emulsion was administered immediately after ischemia at the onset of reperfusion and at 60 min into reperfusion. At the end of 48 h of reperfusion, sections of heart were stained with TTC to quantify the extent of I/R damage in both groups. FIG. 11A shows quantification of the infarct area in mice hearts from saline treated compared to n-3 TG treated group, Myocardial infarct size was significantly reduced ($p<0.05$) in n-3 TG emulsion treated mice (vs saline treated mice). The total area at risk was similar for both groups. Plasma LDH release, a key marker of myocardial injury, was significantly reduced in n-3 TG treated mice. FIG. 11B. These data indicate that acute treatment of n-3 TG during reperfusion markedly reduces injury due to myocardial infarction in mice.

Echocardiography assessment showed substantial differences in fractional shortening (% FS) between control and n-3 TG treated mice. A significant recovery of FS was observed in n-3 TG treated group vs saline treated controls ($p<0.01$) (FIG. 11C). These data along with infarct size changes and LDH levels reduction reveal that acute n-3 TG treatment protects mice from myocardial ischemia-reperfusion injury and improves heart function.

REFERENCES CITED IN EXAMPLE 3

1. Oliveira F L, Rumsey S C, Schlotzer E, Hansen I, arpentier Y A, et al. (1997) Triglyceride hydrolysis of soy oil vs fish oil emulsions. JPEN J Parenter Enteral Nutr 21: 224-229.
2. Qi K, Seo T, Al-fiaideri M, Worgall T S, Vogel T, Carpentier Y A, Deckeibatim. R J. (2002) Omega-3 triglycerides modify blood clearance and tissue targeting pathways of lipid emulsions. Biochemistry. 41(9): 3119-27.
3. Qi K, Al-Haideri M, Seo T, Carpentier Y A, Deckelbaum R J (2003) Effects of particle size on blood clearance and tissue update of lipid emulsions with different triglyceride compositions. JPEN J Parenter Enteral Nutr 27: 58-64.
4. Schwiegelshohn B, Presley J F, Gorecki M, Vogel T, Carpentier Y A, et al. (1995) Effects of apoprotein E on intracellular metabolism of model triglyceride-rich particles are distinct from effects on cell particle update. J Biol Chem 270: 1761-1769.
5. Ananthakrishnan, R., et al., Aldose reductase mediates myocardial ischemia-reperfusion injury in part by opening mitochondrial permeability transition pore. Am J Physiol Heart Circ Physiol, 2009. 296(2): p. H333-41.
6. Hwang, Y. C., et al., Central role for aldose reductase pathway in myocardial ischemic injury. FASEB J, 2004. 18 (11): p. 1192-9.

Example 4: In Vivo Administration of Triglycerides with High DHA Content after Cerebral Hypoxia-Ischemia Reduces Reperfusion Injury A. Materials and Methods
Amounts of n-3 TG in the Lipid Emulsions are as Described Above.
Induction of Unilateral Cerebral H/I Three-day-old C57BL/6J neonatal mice of both genders were purchased from Jackson Laboratories (Bar Harbor, Me.) with their birth mother. The Rice-Vannucci model of H/I was used and modified to p10 neonatal mice.[5] Briefly, on postnatal day 10 H/I was induced by the ligation of the right common carotid artery, which was further cauterized and cut under isoflurane anesthesia. The investigator was blinded to the lipid emulsion treatment during the surgery and after the surgery. The entire surgical procedure was completed within 5 min for each mouse. Pups were then allowed to recover with their dams for 1.5 hr. Surrounding temperature during experiments was kept at 28° C. Mice were then exposed to systemic hypoxia for 15 min in a hypoxic chamber in a neonatal isolette (humidified 8% oxygen/nitrogen, Tech Air Inc., White Plains, N.Y.).[5] The ambient temperature inside the chamber during hypoxia was stabilized at 37±0.3° C. To minimize a temperature-related variability in the extent of the brain damage, during the initial 15 hr of reperfusion mice were kept in an isolette at the ambient temperature of 32° C.

Quantification of Brain Infarction

After 24 hr of reperfusion, the animals were sacrificed by decapitation and brains were immediately harvested. 1-mm coronal slices were cut by using a brain slicer matrix. Slices were then immersed in a PBS solution containing 2% triphenyl-tetrazolium chloride (TTC) at 37° C. for 25 min. TTC is taken up into living mitochondria, which converts it to a red color.[6] Thus, viable tissue stains brick-red, and nonviable (infarcted) tissue can be identified by the absence of staining (white). Using Adobe Photoshop and NIH Image J imaging applications, planar areas of infarction on serial sections were summed to obtain the volume ($mm^3$) of infarcted tissue, which was divided by the total (infarcted+non-infarcted) volume of the hemisphere ipsilateral to carotid artery ligation, and expressed as a percentage of total volume.

Experimental Groups

H/I brain injury was induced in different groups of animals, which received specific treatments before and after H/I injury. Animals followed different treatment protocols.

Protocol 1: Pre-H/I treatment of n-3 TG (containing both DHA and EPA) or n-6 TG emulsions.

Two doses of n-3 TG or n-6 TG emulsions or vehicle (saline, equal volumes/kg) were administered to non-fasting rodents at a fixed dose of 3 mg of n-3 or n-6 TG-FA per mouse for each injection (equivalent to a maximum of 1.5 g of total TG/kg; p10 mice weighed 4-6 gm for these experiments). The first dose was i.p. administered immediately after surgery, and the second immediately at the end of the 15 min hypoxic period. Volumes injected for TG emulsions and saline were always equal.

Since n-3 emulsions contain low concentrations of alpha-tocopherol as an anti-oxidant agent, in separate experiments an equivalent dose of pure alpha-tocopherol to match the content of n-3 emulsion content (0.8 g/L) was given to neonatal mice by i.p. injection of alpha-tocopherol (Vital E®, Intervet, Schering Plough) at a dose of 5 mg alpha-tocopherol/kg body weight, the amount contained in each i.p. injection of the n-3 TG emulsions.

Protocol 2: Post-H/I Treatment of n-3 TG (Containing Both DHA and EPA).

Two doses of the commercially available n-3 TG emulsion or saline were i.p. injected into non-fasting rodents at 0.75 g of n-3 TG/kg body weight for each dose (equivalent to 1.5 g of total TG/kg). The first dose was administered immediately after 15-min hypoxia, and the second at 1 hr after start of the reperfusion period.

Protocol 3: Dose Response, Timing and Specificity of n-3 TG.

Two types of n-3 containing lipid emulsions either Tri-DHA or Tri-EPA (0.1 g n-3 TG/kg or 0.375 g n-3 TG/kg body weight for each dose) were administered twice to non-fasting rodents according to the amount of DHA and EPA in the mixed n-3 TG emulsions. See Table 1. The first dose was initially administered immediately after 15-min hypoxia, and the second after 1 hr of reperfusion. Then in different sets of experiments, the efficacy of Tri-DHA emulsions was determined, with the initial injection administered at four-time points (0 hr, or at 1-hr, 2-hr or 4-hr after H/I), 0.375 g n-3 TG/kg body weight for each dose. For the immediate treatment of 0 hr, the first dose was injected immediately after 15-min hypoxia, with a second injection after 1 hr of reperfusion, whereas in the "delayed" treatments, the first dose was given after the $1^{st}$ or $2^{nd}$ or $4^{th}$ hr of reperfusion and a second dose was administered 1 hr after the $1^{st}$ dose.

Measurement of Blood TG and Glucose Levels

Blood samples for blood TG were directly taken from left ventricle of hearts under isoflurane inhalation from a separate cohort of non-fasting, 10-day-old mice. Samples were taken over a 5 hr period after a single i.p. injection of either 0.75 g n-3 TG/kg commercially available n-3 rich TG (DHA and EPA) emulsions or saline. Total plasma TG was enzymatically measured by GPO-HMMPS, glycerol blanking method (Wako Chemicals USA, Inc., Richmond, Va.). For glucose levels, blood samples were taken from mouse tails from a separate cohort of non-fasting 10-day-old mice. Samples were taken at two time points from each mouse. The first sample was taken at time zero before surgery and TG injection, and the second at about 10 min after H/I and TG injection (approximately 100 min after surgery as described under the Unilateral Cerebral H/I protocol above). Blood glucose levels were electrochemically measured in mg/dL by a glucose meter (OneTouch Ultra, LifeScan, Inc., Milpitas, Calif.).

Measurement of Cerebral Blood Flow (CBF) by Laser Doppler Flowmetry (LDF)

In a cohort of neonatal C57BL/6J mice pups subjected to carotid artery ligation and recovery as described above, relative CBF was measured during hypoxia in ipsilateral (right) hemispheres using a laser Doppler flow meter (Periflux 5000). In these mice, in preparation for CBF measurement the scalp was dissected under isoflurane anesthesia and Doppler probes were attached to the skull (2 mm posterior and 2 mm lateral to the bregma) using fiber optic extensions. Only local anesthesia (1% lidocaine) was used postoperatively. Mice were then placed into a hypoxia chamber (8% $O_2$/92% $N_2$). Changes in CBF in response to hypoxia were recorded for 20 min and expressed as percentage of the pre-hypoxia level for n-3 treated and saline treated neonatal mice.

Measurement of Bleeding Time after n-3 TG Injection

Bleeding times were measured in mice after severing a 3-mm segment of the tail.[7] Two doses of saline were administered vs. n-3 TG in a similar time frame as the original protocol: an initial injection followed by a second injection at 2 hr later. Bleeding times were measured at 45 min after the second dose. The amputated tail was immersed in 0.9% isotonic saline at 37° C., and the time required for the stream of blood to stop was defined as the bleeding time. If no cessation of bleeding occurred after 10 min, the tail was cauterized and 600 s was recorded as the bleeding time.

Long-Term Assessment of Brain Tissue Death

A long-term assessment of cerebral injury was performed at 8 wk after neonatal H/I insult. This cohort of mice at p10 underwent unilateral H/I followed by post H/I injections with either 0.375 g Tri-DHA/kg (n=6) or saline (n=5) as described above. At 8 wk after H/I, mice were sacrificed by decapitation. Brains were removed, and embedded in Tissue Tek-OTC-compound (Sakura Fineteck, Torrance, Calif.) with subsequent snap freezing in dry ice-chilled isopentane (−30° C.), and stored at −80° C. For analysis, coronal sections (10 μm every 500 μm) were cut serially in a Leica cryostat and mounted on Superfrost slides (Thermo Scientific, Illinois). Sections were processed for Nissl staining by using Cresyl Violet Acetate (Sigma-Aldrich, St. Louis, Mo.). Using Adobe Photoshop and NIH Image J imaging applications, 9 sections from each brain containing both the right and left hemispheres were traced for brain tissue area. As previously described[8] the area of left control or contralateral hemisphere which had not had injury was given a value in 100% for each animal. The brain area remaining in the right injured ipsilateral hemisphere was then compared to the left hemisphere, and the difference was taken as the percent right brain tissue loss, for each animal.

Statistical Analysis

Data are presented as mean±SEM. Plasma TG levels were compared at each time point after i.p. injection of n-3 TG emulsion. Student t tests were used for 2-group comparisons. 1-way ANOVA, followed by Bonferroni procedure for post hoc analysis to correct for multiple comparisons, was used to compare the differences among the emulsions on the infarct areas across coronal sections. Statistical significance, which was analyzed by using SPSS software 16.0 (SPSS Inc., Chicago, Ill.), was determined at $p<0.05$.

B. Results of In Vivo Administration of n-3 Tri-DHA after Cerebral Hypoxic-Ischemia Reduced Reperfusion Damage Effects of on-3 Tri-DHA on Blood Triglyceride, Blood Glucose Levels, Bleeding Time and Cerebral Blood Flow after H/L TG levels of saline-injected mice remained constant over 5 hr after i.p. injection reflecting normal blood TG levels in neonates. Further there was no difference in blood glucose levels treated with n-3 TG compared to controls (FIG. 17). After H/I insult, blood glucose levels decreased similarly, about 30% or more, in all groups ($p<0.05$). There was no difference in capillary bleeding times in n-3 treated mice (437±82 sec) as compared to saline controls (418±90 sec). Further, very similar blood flow levels were maintained in neonatal H/I mice whether they were saline treated or n-3 treated in this model.

n-3 TG but not n-6 TG Protected the Brain Against H/I Injury

Figure 18A:
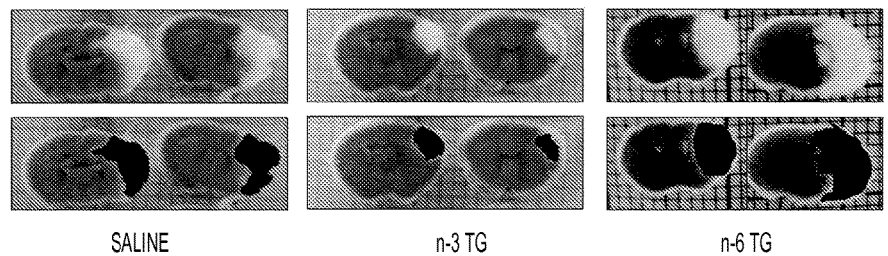
FIG. 18A-18C illustrate TTC stained coronal sections of mouse brain and quantification of injury after H/I.

Coronal sections of brains were stained with TTC to quantify the extent of post H/I brain injury and the effect of n-3 TG [and n-6 THG] injection. FIG. 3A shows representative images of neonatal mouse brain from saline treated, n-6 TG-emulsion-treated and n-3 TG90-DHA30 emulsion-treated mice with pre-and-post injection after H/I, respectively. In all H/I animals, tissue death was localized to the right hemisphere (ipsilateral to ligation) as illustrated by the white areas in the upper panels of FIG. 18A. The image in the lower panels, demonstrated tracings of the infarcted areas for quantifying infarct volume using NIH Image J. The brains from saline treated animals exhibited a consistent pannecrotic lesion involving both cortical and subcortical regions ipsilateral to the ligation. In the majority of the animals the neuroprotection after n-3 TG injection was most marked in the subcortical area, whereas saline treated mice had large cortical and subcortical infarcts.

Figure 18B:
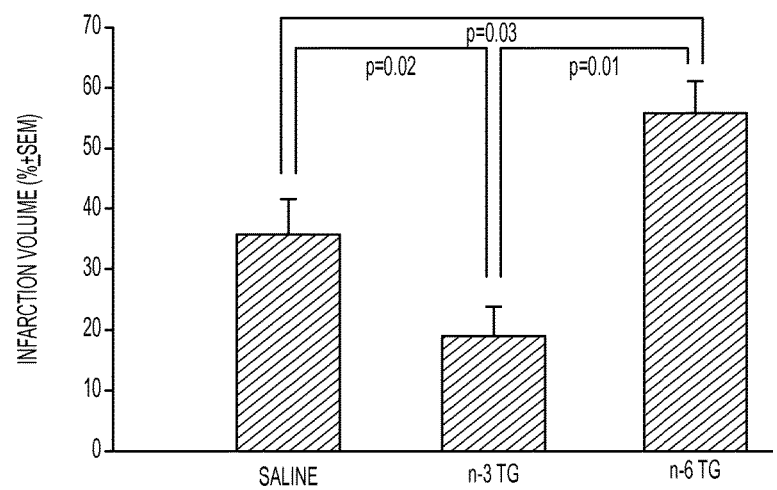

Infarct volume was substantially decreased in n-3 TG treated mice (n=28) compared to saline treated littermates (control) (n=27), 19.9±4.4% vs. 35.1±5.1%, respectively ($p=0.02$). See FIG. 18B. There was a significant increase in infarct volume with n-6 TG emulsion injection compared to saline control ($p=0.03$) and the n-3 TG groups ($p<0.01$).

Because alpha-tocopherol is a component of the TG emulsions (present in low concentrations to prevent FA oxidation) TTC staining was used to compare the extent of cerebral H/I injury in alpha-tocopherol treated and saline treated neonatal mice. There was no significant difference in infarct volume between brains in alpha-tocopherol injected mice compared to saline treated mice (data not shown).

Figure 18C:
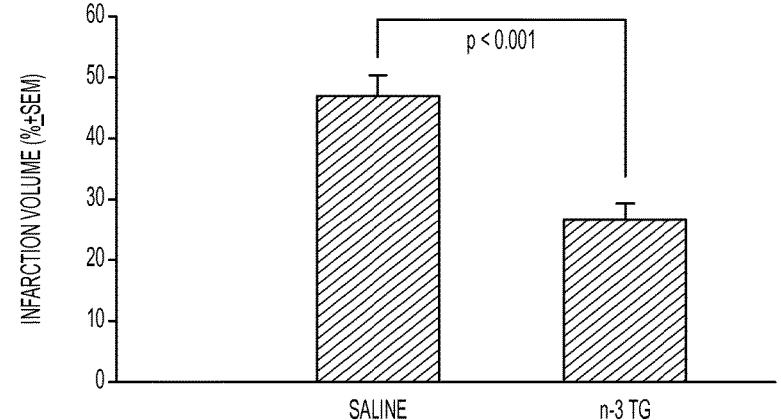

It was then determined if n-3 TG90-DHA30 were effective if injected only after H/I (without injection prior to H/I. See FIG. 18C. Similarly, the smaller n-3 TG90-DHA30 associated lesions were mainly subcortical (data not shown). Compared to saline controls in the immediate post-H/I treatment the total infarct area was significantly reduced almost 50% in the n-3 TG90-DHA30 post H/I-treated group.

DHA but not EPA is Neuroprotective after H/I

Figure 19A:
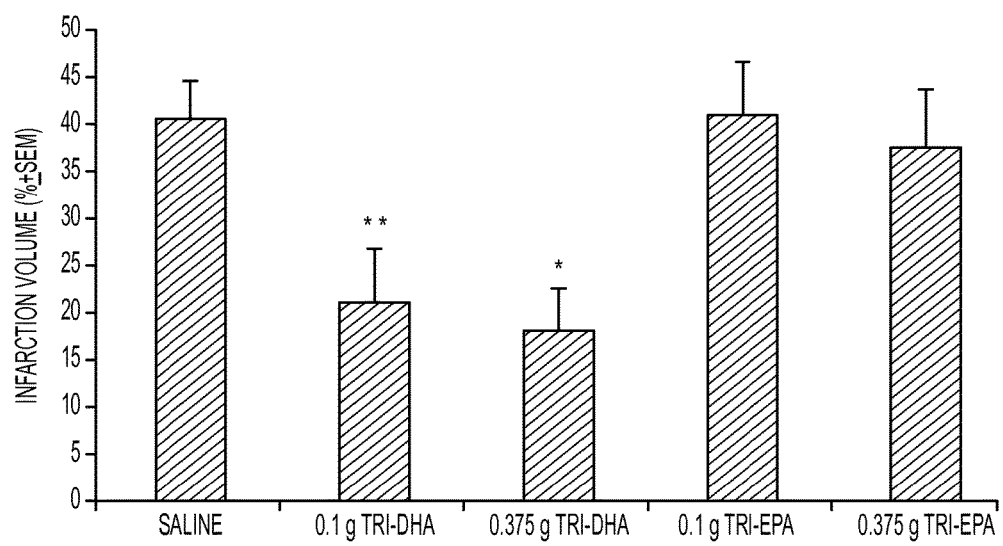
FIG. 19A-19B illustrate the effect of Tri-DHA versus Tri-EPA on cerebral infarct volume after H/I.
Figure 19B:
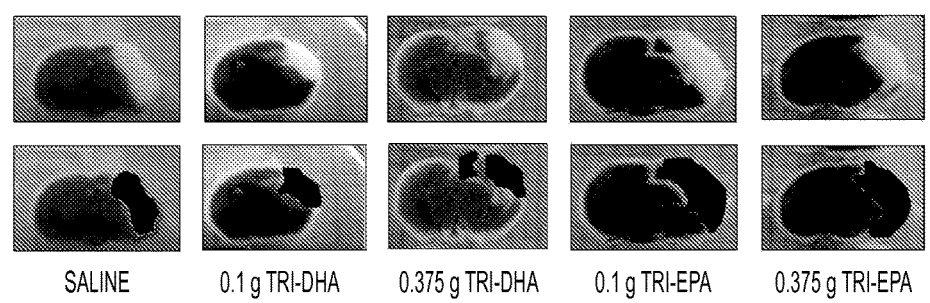

To determine possible differences in neuroprotection of EPA vs. DHA, the extent of brain injury was studied using the post-H/I treatment protocol administering 99% DHA (n-3 99% Tri-DHA) vs. 99% EPA (n-3 99% Tri-EPA) emulsions in two dosages (0.1 g TG/kg vs. 0.375 g TG/kg). No statistical differences in brain infarct volume between the two doses 0.1 g TG/kg and 0.375 g TG/kg in the 99% Tri-DHA-treated groups were observed. However, compared to saline control, total infarct size was reduced by a mean of 48% and 55% by treatment with 0.1 and 0.375 g 99% Tri-DHA/kg, respectively. See FIG. 19A-19B. Neuroprotection was not observed with 99% Tri-EPA injection at either of the two doses compared with saline treatment.

Figure 20:
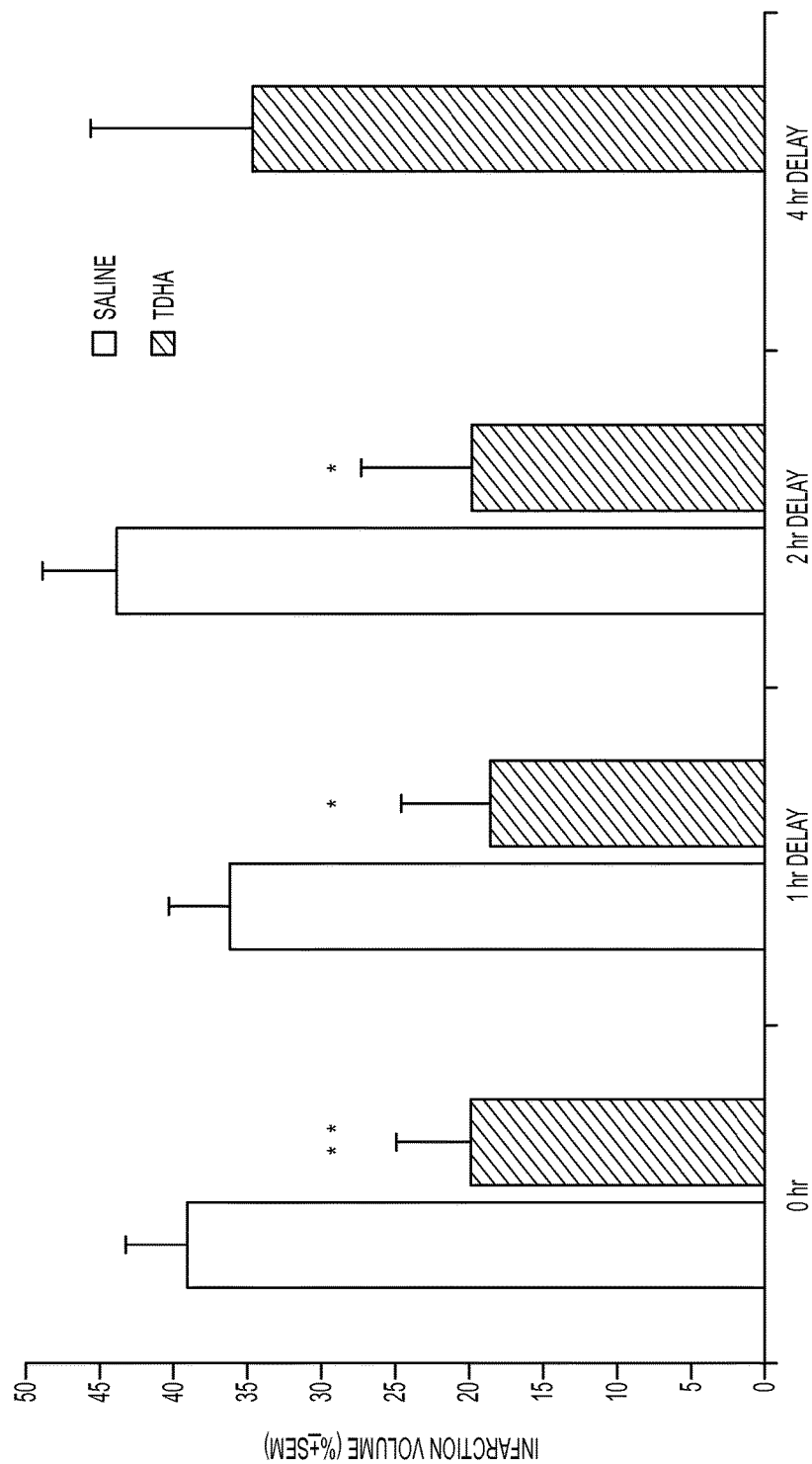
FIG. 20 is a bar graph that illustrates the effects of delayed treatment with Tri-DHA on cerebral infarct volume after H/I. Mice were subjected to 15-min ischemia followed by 24-hr reperfusion and received 2 i.p. administrations at four-time points (immediate [0.1 hr], delayed 1-hr [1.2 hr], or 2-hr [2.3 hr] or 4-hr [4.5 hr] treatments). Each bar represents the mean±SEM of 5-7 independent experiments. * p<0.05; ** p<0.001 vs. saline control (n=10-20 in each group).

To better approximate realistic timelines for neuroprotection after stroke for humans delayed treatment protocols were performed in an effort to study the therapeutic window of Tri-DHA emulsions. No protective effect from TG90-DHA30 administration after a 4-hr delay in treatment was noted when compared with saline group. However, TG90-DHA30 administered at 0 hr immediately post H/I, and then delayed 1-hr and 2-hr post stroke showed similar reduced (~50%) brain infarct volumes compared to saline treated animals. FIG. 20 shows right brain tissue loss in saline- vs Tri-DHA-treated animals. This substantial protection occurred mainly in subcortical areas similar to the findings described above.

Long-Term Neuroprotection

Figure 21:
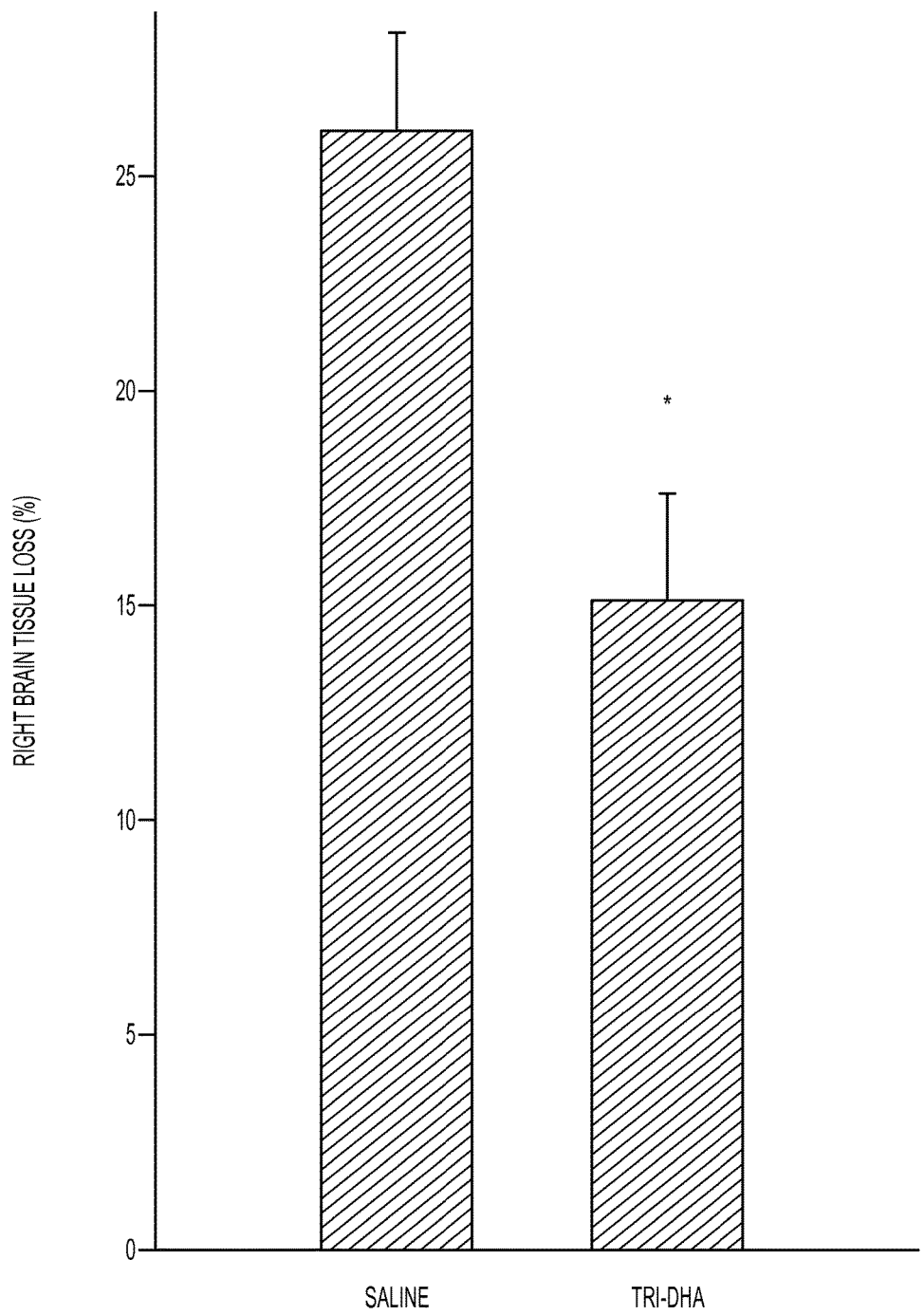
FIG. 21 illustrates the long-term effect of Tri-DHA on cerebral tissue death at 8 wk after H/I. Mice were subjected to 15-min H/I and received 2 i.p. administrations of 0.375 g Tri-DHA/kg (n=6) vs. saline (n=5). Right brain tissue loss in relation to the contralateral hemisphere was calculated and expressed as a percentage. Each bar represents the mean±SEM. * p<0.05.
Figure 22A:
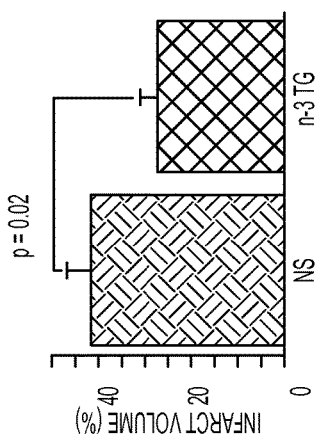
FIG. 22A-22B illustrate acute n-3 TG injection which decreased brain $Ca^{2+}$ induced opening of mitochondrial permeability transition pores (mPTP) after H/I. After H/I and after n-3 TG injection, mitochondrial function is maintained.
Figure 22B:
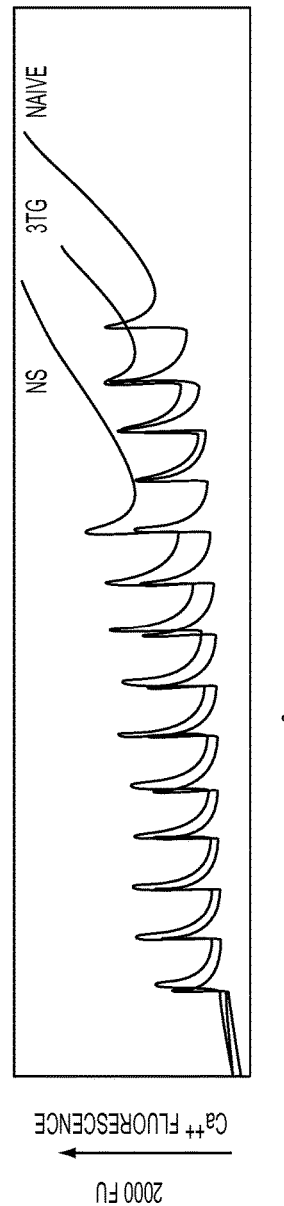

Coronal brain sections of adult mice were processed for Nissl staining (FIG. 6) to examine the effects of H/I and TG90-DHA30 treatment on brain and neuronal cell loss for long-term outcome at 8 wk after H/I insult. As compared to the left control (contralateral hemisphere), the injured areas of the right hemisphere display gross neuronal cell loss. As shown in FIG. 21, brain tissue loss was markedly increased by 1.67 fold in the right hemisphere of saline-treated mice (n=5) as compared to TG90-DHA30 treated mice (n=6), 25.0±2.4% vs. 15.0±2.5%, respectively ($p=0.02$). Thus, neuroprotection after injury and TG90-DHA30 injection that are observed 24 hr after H/I can be demonstrated histologically almost 2 months after the initial stroke insult.

REFERENCES CITED FROM EXAMPLE 4

1. Oliveira F L, Rumsey S C, Schlotzer E, Hansen I, Carpentier Y A, et al. (1997) Triglyceride hydrolysis of soy oil vs fish oil emulsions. JPEN J Parenter Enteral Nutr 21: 224-229.
2. Qi K, Seo T, Al-Haideri M, Worgall T S, Vogel T, et al. (2002) Omega-3 triglycerides modify blood clearance and tissue targeting pathways of lipid emulsions. Biochemistry 41: 3119-3127.
3. Qi K, Al-Haideri M, Seo T, Carpentier Y A, Deckelbaum R J (2003) Effects of particle size on blood clearance and tissue uptake of lipid emulsions with different triglyceride compositions. JPEN J Parenter Enteral Nutr 27: 58-64.
4. Schwiegelshohn B, Presley J F, Gorecki M, Vogel T, Carpentier Y A, et al. (1995) Effects of apoprotein E on intracellular metabolism of model triglyceride-rich particles are distinct from effects on cell particle uptake. J Biol Chem 270: 1761-1769.
5. Ten V S, Bradley-Moore M, Gingrich J A, Stark R I, Pinsky D J (2003) Brain injury and neurofunctional deficit in neonatal mice with hypoxic-ischemic encephalopathy. Behav Brain Res 145: 209-219.
6. Liszczak™, Hedley-Whyte E T, Adams J F, Han D H, Kolluri V S, et al. (1984) Limitations of tetrazolium salts in delineating infarcted brain. Acta Neuropathol 65: 150-157.
7. Denis C, Methia N, Frenette P S, Rayburn H, Ullman-Cullere M, et al. (1998) A mouse model of severe von Willebrand disease: defects in hemostasis and thrombosis. Proc Natl Acad Sci USA 95: 9524-9529.
8. Seo T, Blaner W S, Deckelbaum R J (2005) Omega-3 fatty acids: molecular approaches to optimal biological outcomes. Curr Opin Lipidol 16: 11-18.
9. Bruno A, Biller J, Adams H P, Jr., Clarke W R, Woolson R F, et al. (1999) Acute blood glucose level and outcome from ischemic stroke. Trial of ORG 10172 in Acute Stroke Treatment (TOAST) Investigators. Neurology 52: 280-284.

Example 5: In Vivo Cerebral Hypoxia/Ischemia Treatment with 20% n-3 TG Emulsion Reduces Reperfusion Damage A. 60 min. Hypoxia in Mice Postnatal day 19-21 Wistar rats of both genders were subjected to unilateral (right) carotid artery ligation. See Rice, J. E., 3rd, R. C. Vannucci, et al. (1981), "The influence of immaturity on hypoxic-ischemic brain damage in the rat," *Ann Neurol* 9(2): 131-41 and Vannucci, S. J., L. B. Seaman, et al. (1996), "Effects of hypoxia-ischemia on GLUT1 and GLUT3 glucose transporters in immature rat brain," *Journal of Cerebral Blood Flow & Metabolism* 16(1): 77-81.

Immediately after ligation, six rats were given 50 mg 20% omega-3 lipid-based emulsion (0.25 cc)(a 20% long chain omega-3 triglyceride-based formula having >45% of total omega-3 fatty acid as eicosapentaenoic acid (EPA) and docosahexaenoic acid (DHA)) via orogastric feeding tube, and six control rats were given 0.25 cc water, both enterally. The 20% omega-3 lipid-based emulsion was made placing 20 gm of omega-3 triglyceride in 100 ml of water, and emulsifying with 1.2 gm of egg yolk lecithin. Rats were allowed to recover for 2 hours and then they underwent hypoxia-ischemia for 60 minutes of 8% oxygen at a constant temperature. The six pre-treated rats were given another dose of 50 mg omega-3 lipid-based emulsion immediately after the hypoxia-ischemia and control rats were given 0.25 cc water. All rats were euthanized at 72 hours of reperfusion. The brains were removed and cut into 2 mm sections and stained with 2, 3, 5, Triphenyl-2H-tetrazolium chloride (TTC). TTC is a vital die that stains cells red that have respiring mitochondria. Dead tissue (infarct) appears white. The sections were scored as follows:

0—no evidence of edema or cell death
1—edema without cell death
2—edema with minimal cell death
3—edema with significant cell death All rats survived 60 minutes of hypoxia-ischemia. Six of the six control rats had edema and/or cell death with a mean score of 2+/−0.83 (standard deviation), while two of the six treated rats had damage with a mean score of 0.42+/−0.62 (p<0.005).

B. 65 min Hypoxia

Postnatal day 19-21 Wistar rats of both genders were subjected to unilateral (right) carotid artery ligation. Immediately after ligation, six rats were given 50 mg 20% omega-3 lipid-based emulsion (0.25 cc)(20% omega-3 fatty acid based formula having >40% of total omega-3 fatty acid as EPA and DHA) via orogastric feeding tube and six control rats were given 0.25 cc water, both enterally. The emulsion was made as described in Example 1. The rats recovered for two hours, and then underwent hypoxia-ischemia for 65 minutes of 8% oxygen at a constant temperature. The six pre-treated rats were given another dose of 50 mg omega-3 lipid-based emulsion immediately after the hypoxia-ischemia and control rats were given 0.25 cc water. All rats were euthanized at 72 hours of reperfusion. The brains were removed and cut into 2 mm sections and stained with 2, 3, 5, Triphenyl-2H-tetrazolium chloride (TTC). The sections were scored as above.

The 65 or 60 minutes of hypoxia-ischemia produced damage in all rats. Four of the six control rats survived with a mean score of 2.75+/−0.50, while five of the six treated rats survived with a mean score of 1.70+/=0.76 (p<0.05).

C. Treatment of Rats with Omega-3 Triglyceride Lipid Emulsion Prior to 60 Minutes of Hypoxia Postnatal day 19-21 Wistar rats were subjected to unilateral (right) carotid artery. Immediately after ligation, six rats were given 50 mg of a 20% omega-3 lipid-based emulsion (0.25 cc), and six control rats were given 0.25 cc water, both enterally. The emulsion was as described above in Example 1. Rats were allowed to recover for two hours, and then underwent hypoxia-ischemia for 60 minutes of 8% oxygen at a constant temperature. The six pre-treated rats were given another dose of 50 mg omega-3 triglyceride lipid emulsion immediately after the hypoxia/ischemia and control rats were given 0.25 cc water. At 72 hours of reperfusion, the rats were euthanized and their brains removed, cut into 2 mm sections and stained with 2,3,5 triphenyl-2H-tetrazolium chloride (TTC). The damage in each animal was then given a score from 0 (no damage) to 4 (>60% ipsilateral hemisphere infarcted). All of the vehicle-treated animals suffered brain damage, with a mean damage score of 2.00+0.89; the omega-3 triglyceride lipid emulsion-treated rats were significantly less damaged, having a mean damage score 0.33+0.52, p<0.05. The size of brain infarcts was determined by TTC staining. Note received enteral administration of TG emulsion.

These results show that when omega-3 triglycerides were administered either immediately before and/or after hypoxia-ischemia they confer a significant neuroprotection.

Very similar results were obtained when the omega-3 triglycerides were injected parenterally.

D. Treatment Following Hypoxic Ischemia

Post-natal day 19-21 rat pups were subjected to unilateral carotid artery ligation and 60 minutes of hypoxic ischemia, according to the previously described protocol. On four separate occasions, rats were treated by parenteral injection of omega-3 lipid-based emulsion (100 mg) immediately after the insult, and again at four hours after the insult. The emulsion was as described above in Example 1. Brain damage was evaluated by TTC staining at 72 hours of reperfusion. In each instance, administration of the omega-3 lipid-based oil emulsion provided greater than 50% protection, i.e. reduction of tissue damage.

A total of 14 control subjects (saline-treated) and 21 treated subjects (omega-3 lipid-based emulsion treated) were included in the experiment. Mean damage scores were: 1.93±0.22 (SEM), control, 0.78±0.16 emulsion-treated; p<0.0001 by two-tailed test. Thus, in addition to the significance of the overall protection, it can be seen that 40% of the treated animals were 100% protected (no damage at all, compared to 1/14 untreated; 40% suffered only mild damage, compared to 1/14 mildly damaged untreated animals. These results indicate that treatment following hypoxic-ischemia provides a neuroprotective benefit as indicated by a reduction of tissue damage.

Preliminary experiments conducted in the adult mouse show a comparable level of neuroprotection from hypoxic-ischemic damage. (Data not shown.)

Fatty acyl composition analyses of brain lipids (by gas liquid chromatography) after hypoxia/ischemia showed no relative differences between infarcted brain versus non infarcted brain indicating that effects of acute administration of omega-3 emulsions were not dependent on fatty acid compositional changes in brain membranes. In the infarcted areas, however, absolute concentrations of all fatty acids fell to similar degrees by about 15% (μg fatty acid per gram wet brain) indicating brain edema. This decrease did not occur with administration of omega-3 emulsions indicating that these omega-3 fatty acids prevented the brain edema as well as infarction.

The invention has been described with reference to specific embodiments. It will, however, be evident that various modifications and changes may be made thereto without departing from the broader spirit and scope of the invention. The specification and drawings are, accordingly, to be regarded in an illustrative rather than a restrictive sense. The invention is illustrated herein by the experiments described above and by the following examples, which should not be construed as limiting. The contents of all references, pending patent applications and published patents, cited throughout this application are hereby expressly incorporated by reference. Although specific terms are employed, they are used as in the art unless otherwise indicated.

REFERENCES

Roger V L, Go A S, Lloyd-Jones D M et al. (2012) Heart disease and stroke statistics 2012 update: a report from the American Heart Association Circulation. 125 (1), pp. e2-e220

Murphy E and Steenbergen C. (2008) Mechanisms underlying acute protection from cardiac ischemia-reperfusion injury. Physiological Reviews, 88, 581-609.

Buja L M. (2005) Myocardial ischemia and reperfusion injury. Cardiovascular Pathology, 14, 170-175.

Redout E M, Wagner M J, Zuidwijk M J, Boer C, Musters R J, van Hardeveld C et al (2007) Right-ventricular failure is associated with increased mitochondrial complex II activity and production of reactive oxygen species. Cardiovasc Res 75:770-781.

Lopaschuk G D, Ussher J R, Folmes C D, Jaswal J S, Stanley W C. (2010) Myocardial fatty acid metabolism in health and disease. Physiol Rev.

Griendling K K, and FitzGerald G A. (2003) Oxidative stress and cardiovascular injury: Part I: Basic mechanisms and in vivo monitoring of ROS. Circulation, 108, 1912-1916.

Marczin N, El-Habashi N, Hoare G S, Bundy R E, and Yacoub M. (2003) Antioxidants in myocardial ischemia-reperfusion injury: Therapeutic potential and basic mechanisms. Archives of Biochemistry and Biophysics, 420, 222-236.

Deckelbaum R J, Torrejon C. (2012) The omega-3 fatty acid nutritional landscape: health benefits and sources. J Nutr.

Torrejon C, Jung U J, Deckelbaum R J. (2007) n-3 Fatty acids and cardiovascular disease: actions and molecular mechanisms. Prostaglandins Leukot Essent Fatty Acids.

Stanley W C, Dabkowski E R, Ribeiro R F Jr, O'Connell K A. (2012) Dietary fat and heart failure: moving from lipotoxicity to lipoprotection. Circ Res.

Lichtenstein A H, Appel I I, Brands M, et al. (2006) Diet and lifestyle recommendations revision 2006: a scientific statement from the American Heart Association Nutrition Committee. Circulation 114, 82-96.

Filion K B, El Khoury F, Bielinski M, et al. (2010) Omega-3 fatty acids in high-risk cardiovascular patients: a meta-analysis of randomized controlled trials. BMC Cardiovasc Disord 10,24.

Delgado-Lista J, Perez-Martinez P, Lopez-Miranda J, Perez-Jimenez F. (2012) Long chain omega-3 fatty acids and cardiovascular disease: a systematic review. Br J Nutr.

Skulas-Ray A C, Kris-Etherton P M, Harris W S, Vanden Heuvel J P, Wagner P R, West S G. (2011) Dose-response effects of omega-3 fatty acids on triglycerides, inflammation, and endothelial function in healthy persons with moderate hypertriglyceridemia. Am J Clin Nutr.

McKenney J M, Sica D. (2007) Role of prescription omega-3 fatty acids in the treatment of hypertriglyceridemia. Pharmacotherapy; 27:715-28.

Gruppo Italiano per lo Studio della Sopravvivenza nell'Infarto miocardico. Dietary supplementation with n-3 polyunsaturated fatty acids and vitamin E after myocardial infarction: results of the GISSI-Prevenzione trial. (1999) Lancet; 354:447-55.

Jung U J, Torrejon C, Tighe A P, Deckelbaum R J. (2008) n-3 Fatty acids and cardiovascular disease: mechanisms underlying beneficial effects. Am J Clin Nutr. 2003S-9S.

Chang C L, Deckelbaum R J. (2013) Omega-3 fatty acids: mechanisms underlying 'protective effects' in atherosclerosis. Curr Opin Lipidol. 24(4): 345-50.

Densupsoontorn N, Worgall T S, Seo T, Hamai H, Deckelbaum R J. (2007) Fatty acid supplied as triglyceride regulates SRE-mediated gene expression as efficiently as free fatty acids. Lipids. 42(10):885-91.

Caputo M, Zirpoli H, Torino G, Tecce M F. (2011) Selective regulation of UGT1A1 and SREBP-1c mRNA expression by docosahexaenoic, eicosapentaenoic, and arachidonic acids. J Cell Physiol. 226(1): 187-93.

Rauch B, Schiele R, Schneider S, Diller F, Victor N, Gohlke H, Gottwik M, Steinbeck G, Del Castillo U, Sack R, Worth H, Katus H, Spitzer W, Sabin G, Senges J; OMEGA Study Group. (2010) OMEGA, a randomized, placebo-controlled trial to test the effect of highly purified omega-3 fatty acids on top of modern guideline-adjusted therapy after myocardial infarction. Circulation. 122(21): 2152-9.

Williams J J, Mayurasakorn K, Vannucci S J, Mastropietro C, Bazan N G, Ten V S, Deckelbaum R J. (2013) N-3 fatty acid rich triglyceride emulsions are neuroprotective after cerebral hypoxic-ischemic injury in neonatal mice. PLoS One; 8(2):e56233.

Kaga S, Zhan L, Altaf E, and Maulik N. (2006) Glycogen synthase kinase-3beta/beta-catenin promotes angiogenic and anti-apoptotic signaling through the induction of VEGF, Bcl-2 and survivin expression in rat ischemic preconditioned myocardium. Journal of Molecular and Cellular Cardiology, 40, 138-147.

Sugden P H. (2003) Ras, Akt, and mechanotransduction in the cardiac myocyte. Circulation Research, 93, 1179-1192.

Bellot G, Garcia-Medina R, Gounon P, Chiche J, Roux D, Pouysségur J, Mazure N M. (2009) Hypoxia-induced autophagy is mediated through hypoxia-inducible factor induction of BNIP3 and BNIP3L via their BH3 domains. Mol Cell Biol. 29(10):2570-81.

Vacek T P, Vacek J C, Tyagi N, Tyagi S C. (2012) Autophagy and heart failure: a possible role for homocysteine. Cell Biochem Biophys. 62(1):1-11.

Jung U J, Torrejon C, Chang C L, Hamai H, Worgall T S, Deckelbaum R J. (2012) Fatty acids regulate endothelial lipase and inflammatory markers in macrophages and in mouse aorta: a role for PPARγ. Arterioscler Thromb Vasc Biol. 32(12):2929-37.

Abdillahi M, Ananthakrishnan R, Vedantham S, Shang L, Zhu Z, Rosario R, Zirpoli H, Bohren K M, Gabbay K H, Ramasamy R. (2012) Aldose reductase modulates cardiac glycogen synthase kinase-3β phosphorylation during ischemia-reperfusion. Am J Physiol Heart Circ Physiol. 303(3): H297-308.

Khairallah R J, Kim J, O'Shea K M, O'Connell K A, Brown B H, Galvao T, Daneault C, Des Rosiers C, Polster B M, Hoppel C L, Stanley W C. (2012) Improved mitochondrial function with diet-induced increase in either docosahexaenoic acid or Arachidonic acid in membrane phospholipids. PLoS One.

Lehman J J, Kelly D P. (2002) Gene regulatory mechanisms governing energy metabolism during cardiac hypertrophic growth. Heart Fail Rev. 7(2): 175-85.

Lei L, Mason S, Liu D, Huang Y, Marks C, Hickey R, Jovin I S, Pypaert M, Johnson R S, Giordano F J. (2008) Hypoxia-inducible factor-dependent degeneration, failure, and malignant transformation of the heart in the absence of the von Hippel-Lindau protein. Mol Cell Biol. 28(11):3790-803.

Narravula S, Colgan S P. (2001) Hypoxia-inducible factor 1-mediated inhibition of peroxisome proliferator-activated receptor alpha expression during hypoxia. J Immunol. 15; 166(12): 7543-8.

Sugden M C, Warlow M P, Holness M J. (2012) The involvement of PPARs in the causes, consequences and mechanisms for correction of cardiac lipotoxicity and oxidative stress. Curr Mol Pharmacol. 5(2): 224-40.

Duan S Z, Ivashchenko C Y, Russell M W, Milstone D S, Mortensen R M. (2005) Cardiomyocyte-specific knockout and agonist of peroxisome proliferator-activated receptor-gamma both induce cardiac hypertrophy in mice. Circ Res. 97(4):372-9.

Son N H, Park T S, Yamashita H, Yokoyama M, Huggins L A, Okajima K, Homma S, Szabolcs M J, Huang L S, Goldberg I J. (2007) Cardiomyocyte expression of PPAR-gamma leads to cardiac dysfunction in mice. J Clin Invest. 117(10):2791-801.

Krishnan J, Suter M, Windak R, Krebs T, Felley A, Montessuit C, Tokarska-Schlattner M, Aasum E, Bogdanova A, Perriard E, Perriard J C, Larsen T, Pedrazzini T, Krek W (2009) Activation of a HIF-1/PPARγ axis underlies the integration of glycolytic and lipid anabolic pathways in pathologic cardiac hypertrophy. Cell Metab. 9(6): 512-24.

Cross D A, Alessi D R, Cohen P, Andjelkovich M, Hemmings B A (1995) Inhibition of glycogen synthase kinase-3 by insulin mediated by protein kinase B. Nature. 378: 785-789.

Fujio Y, Nguyen T, Wencker D, Kitsis R N, Walsh K. (2000) Akt promotes survival of cardiomyocytes in vitro and protects against ischemia-reperfusion injury in mouse heart. Circulation, 101: 660-667

Mullonkal C J, Toledo-Pereyra L H. (2007) Akt in ischemia and reperfusion. Journal of Investigative Surgery. 20: 195-203.

Pattingre S, Tassa A, Qu X, Garuti R, Liang X H, Mizushima N, Packer M, Schneider M D, Levine B. (2005) Bcl-2 antiapoptotic proteins inhibit Beclin 1-dependent autophagy. Cell. 122(6): 927-39.

National Heart, Lung, and Blood institute computation based on National Center for Health Statistics annual data.

Circulation: Heart Disease and Stroke Statistics—2013 Update: A Report From the American Heart Association.

Brunet A, Datta S R and Greenberg M E (2001) Transcription-dependent and -independent control of new survival b) the PI3K-Akt signaling pathway, Curr Opin Neurobiol. 11(3): 297-305.

Xu Z, Kim S. Huh J (2013) Zinc plays a critical role in the cardioprotective effect of post-conditioning by enhancing the activation of the RISK pathway' in rat hearts, J Mol Cell Cardiol. 66C: 12-17, Barros K V, Carvalho P O, Cassulino A P, Andrade I, West A L, Miles E A, Calder P C, Silveira V L (2013) Fatty acids in plasma, white and red blood cells, and tissues after oral or intravenous administration of fish oil in rats. Clin Nutr. 2(6): 993-8.

Rodrigo R, Prieto J C, Castillo R. (2013) Cardioprotection against ischemia-reperfusion by vitamins C and E plus n-3 fatty acids: molecular mechanisms and potential clinical application. Cell Biochem Funct. 124: 1-15.

Castillo R L, Arias C, Farías J G. (2013) Omega 3 chronic supplementation attenuates myocardial ischaemia-reperfusion injury through reinforcement of antioxidant defense system in rats. Cell Biochem Funct. doi: 10.1002/cbf.3012. [Epub ahead of print].

Gao J Y, Yasuda S, Tsuburaya R, Ito Y, Shiroto T, Hao K, Aizawa K, Kikuchi Y, Ito K, Shimokawa H (2011) Long-term treatment with eicosapentaenoic acid ameliorates myocardial ischemia-reperfusion injury in pigs in vivo. —Involvement of Rho-kinase pathway inhibition- Circ J. 75(8):1843-51.

Hoogeveen E K, Geleijrise J M, Kromhout D, Giltay E J (2013) No effect of n-3 fatty acids on high-sensitivity C-reactive protein after myocardial infarction: The Alpha Omega Trial. Eur J Prev Cardiol.

Chen Z, Chua C C, Ho Y S, Hamdy R C, Chua B H. (2001) Overexpression of Bcl-2 attenuates apoptosis and protects against myocardial I/R injury in transgenic mice. Am J Physiol Heart Circ Physiol 280: H2313-H2320.

Imahashi K, Schneider M D, Steenbergen C, Murphy E. (2004) Transgenic expression of Bcl-2 modulates energy metabolism, prevents cytosolic acidification during ischemia, reduces ischemia/reperfusion injury. Circ Res 95: 734-741

Murphy E, Steenbergen C. (2007) Preconditioning: the mitochondrial connection. Annu Rev Physiol, 69:51-67.

Ravingerová T, et al. (2012) PPAR-alpha activation as a preconditioning-like intervention in rats in vivo confers myocardial protection against acute ischaemia-reperfusion injury: involvement of PI3K-Akt, Can J Physiol Pharmacol. 90(8): 1135-44.

Qi K, Seo T, Al-Haideri M, Worgall T S, Vogel T, Carpenter Y A, Deckelbaum R J. (2002) Omega-3 triglycerides modify blood clearance and tissue targeting pathways of lipid emulsions. Biochemistry. 41(9): 3119-27.

Xue B, Yang Z, Wang X, Shi H. (2012) Omega-3 polyunsaturated fatty acids antagonize macrophage inflammation via activation of AMPK/SIRT1 pathway. PloS One; 7:e45990.

Akbar M, Calderon F, Wen Z, Kim H Y. (2005) Docosahexaenoic acid: a positive modulator of Akt signaling in neuronal survival. Proc Natl Acad Sci USA. 102(31): 10858-63.

Abdelrahman M, Sivarajah A, Thiemermann C. (2005) Beneficial effects of PPAR-gamma ligands in ischemia-reperfusion injury, inflammation and shock. Cardiovasc Res 65: 772-781.

Wang G, Wei J, Guan Y, Jin N, Mao J, Wang X. (2005) Peroxisome proliferator-activated receptor-gamma agonist rosiglitazone reduces clinical inflammatory responses in type 2 diabetes with coronary artery disease after coronary angioplasty. Metabolism 54: 590-597.

Ananthakrishnan, R., et al., Aldose reductase mediates myocardial ischemia-reperfusion injury in part by opening mitochondrial permeability transition pore. Am J Physiol Heart Circ Physiol, 2009. 296(2): p. H333-41.

Hwang, Y. C., et al., Central role for aldose reductase pathway in myocardial ischemic injury. FASEB J, 2004. 18(11): p. 1192-9.

Murphy E (2004) Inhibit GSK-3beta or there's heartbreak dead ahead. J Clin Invest 113: 1526-1528.

Murphy E, Steenbergen C (2005) Inhibition of GSK-3beta as a target for cardioprotection: the importance of timing, location, duration and degree of inhibition. Expert Opin Ther Targets 9: 447-456.

Juhaszova M, Zorov D B, Yaniv Y, Nuss H B, Wang S, Sollott S J (2009) Role of glycogen synthase kinase-3beta in cardioprotection. Circ Res 104: 1240-1252.

Lloyd-Jones D, Adams R J, Brown T M, Carnethon M, Dai S, et al. (2009) Heart disease and stroke statistics—2010 update: a report from the American Heart Association. Circulation 121: e46-e215.

Raju T N, Nelson K B, Ferriero D, Lynch J K (2007) Ischemic perinatal stroke: summary of a workshop sponsored by the National Institute of Child Health and Human Development and the National Institute of Neurological Disorders and Stroke. Pediatrics 120: 609-616.

Callaway J K (2001) Investigation of AM-36: a novel neuroprotective agent. Clin Exp Pharmacol Physiol 28: 913-918.

Legido A, Christos K (2000) Perinatal Hypoxic Ischemic Encephalopathy: Current and Future Treatments. International Pediatrics 15: 143-151.

Mayurasakorn K, Williams J J, Ten V S, Deckelbaum R J (2011) Docosahexaenoic acid: brain accretion and roles in neuroprotection after brain hypoxia and ischemia. Curr Opin Clin Nutr Metab Care 14: 158-167.

Calder P C (2010) Omega-3 fatty acids and inflammatory processes. Nutrients 2: 355-374.

Deckelbaum R J, Worgall T S, Seo T (2006) n-3 fatty acids and gene expression. Am J Clin Nutr 83: 1520S-1525S.

Seo T, Blaner W S, Deckelbaum R J (2005) Omega-3 fatty acids: molecular approaches to optimal biological outcomes. Curr Opin Lipidol 16: 11-18.

Bazan N G, Molina M F, Gordon W C (2011) Docosahexaenoic acid signalolipidomics in nutrition: significance in aging, neuroinflammation, macular degeneration, Alzheimer's, and other neurodegenerative diseases. Annu Rev Nutr 31: 321-351.

Perlman J M (2007) Pathogenesis of hypoxic-ischemic brain injury. Journal of Perinatology 27: S39-S46.

Belayev L, Marcheselli V L, Khoutorova L, Rodriguez de Turco E B, Busto R, et al. (2005) Docosahexaenoic acid complexed to albumin elicits high-grade ischemic neuroprotection. Stroke 36: 118-123.

Singh A K, Yoshida Y, Garvin A J, Singh I (1989) Effect of fatty acids and their derivatives on mitochondrial structures. J Exp Pathol 4: 9-15.

Oliveira F L, Rumsey S C, Schlotzer E, Hansen I, Carpentier Y A, et al. (1997) Triglyceride hydrolysis of soy oil vs fish oil emulsions. JPEN J Parenter Enteral Nutr 21: 224-229.

Adolph M (1999) Lipid emulsions in parenteral nutrition. Ann Nutr Metab 43: 1-13.

Vannucci S J, Hagberg H (2004) Hypoxia-ischemia in the immature brain. J Exp Biol 207: 3149-3154.

Pavlakis S G, Hirtz D G, DeVeber G (2006) Pediatric stroke: Opportunities and challenges in planning clinical trials. Pediatr Neurol 34: 433-435.

Ten V S, Bradley-Moore M, Gingrich J A, Stark R I, Pinsky D J (2003) Brain injury and neurofunctional deficit in neonatal mice with hypoxic-ischemic encephalopathy. Behav Brain Res 145: 209-219.

Qi K, Seo T, Al-Haideri M, Worgall T S, Vogel T, et al. (2002) Omega-3 triglycerides modify blood clearance and tissue targeting pathways of lipid emulsions. Biochemistry 41: 3119-3127.

Qi K, Al-Haideri M, Seo T, Carpentier Y A, Deckelbaum R J (2003) Effects of particle size on blood clearance and tissue uptake of lipid emulsions with different triglyceride compositions. JPEN J Parenter Enteral Nutr 27: 58-64.

Granot E, Schwiegelshohn B, Tabas I, Gorecki M, Vogel T, et al. (1994) Effects of particle size on cell uptake of model triglyceride-rich particles with and without apoprotein E. Biochemistry 33: 15190-15197.

Schwiegelshohn B, Presley J F, Gorecki M, Vogel T, Carpentier Y A, et al. (1995) Effects of apoprotein E on intracellular metabolism of model triglyceride-rich particles are distinct from effects on cell particle uptake. J Biol Chem 270: 1761-1769.

Liszczak T M, Hedley-Whyte E T, Adams J F, Han D H, Kolluri V S, et al. (1984) Limitations of tetrazolium salts in delineating infarcted brain. Acta Neuropathol 65: 150-157.

Denis C, Methia N, Frenette P S, Rayburn H, Ullman-Cullere M, et al. (1998) A mouse model of severe von Willebrand disease: defects in hemostasis and thrombosis. Proc Natl Acad Sci USA 95: 9524-9529.

Niatsetskaya Z V, Sosunov S A, Matsiukevich D, Utkina-Sosunova I V, Ratner V I, et al. (2012) The oxygen free radicals originating from mitochondrial complex I contribute to oxidative brain injury following hypoxia-ischemia in neonatal mice. J Neurosci 32: 3235-3244.

Bruno A, Biller J, Adams H P, Jr., Clarke W R, Woolson R F, et al. (1999) Acute blood glucose level and outcome from ischemic stroke. Trial of ORG 10172 in Acute Stroke Treatment (TOAST) Investigators. Neurology 52: 280-284.

Caspersen C S, Sosunov A, Utkina-Sosunova I, Ratner V I, Starkov A A, et al. (2008) An isolation method for assessment of brain mitochondria function in neonatal mice with hypoxic-ischemic brain injury. Dev Neurosci 30: 319-324.

Berman D R, Mozurkewich E, Liu Y, Barks J (2009) Docosahexaenoic acid pretreatment confers neuroprotection in a rat model of perinatal cerebral hypoxia-ischemia. Am J Obstet Gynecol 200: 305 e301-306.

Williams J J, Bazan N G, Ten V S, Vannucci S J, Mastropietro C, et al. (2009) n-3 fatty acids are neuroprotective after cerebral hypoxia-ischemia in rodent models. FASEB J 23: 334.335 (Abstract).

Qi K, Seo T, Jiang Z, Carpentier Y A, Deckelbaum R J (2006) Triglycerides in fish oil affect the blood clearance of lipid emulsions containing long- and medium-chain triglycerides in mice. J Nutr 136: 2766-2772.

Pan H C, Kao T K, Ou Y C, Yang D Y, Yen Y J, et al. (2009) Protective effect of docosahexaenoic acid against brain injury in ischemic rats. J Nutr Biochem 20: 715-725.

Huang J, Mocco J, Choudhri T F, Poisik A, Popilskis S J, et al. (2000) A modified transorbital baboon model of reperfused stroke. Stroke 31: 3054-3063.

Mayurasakorn K, Williams J J, Ten V S, Deckelbaum R J (2011) n-3 but not n-6 fatty acids prevent brain death after hypoxic ischemic injury. FASEB J 25 777.710 (Abstract).

Grimsgaard S, Bonaa K H, Hansen J B, Nordoy A (1997) Highly purified eicosapentaenoic acid and docosahexaenoic acid in humans have similar triacylglycerol-lowering effects but divergent effects on serum fatty acids. Am J Clin Nutr 66: 649-659.

Stanley W C, Khairallah R J, Dabkowski E R (2012) Update on lipids and mitochondrial function: impact of dietary n-3 polyunsaturated fatty acids. Curr Opin Clin Nutr Metab Care 15: 122-126.

Khairallah R J, Sparagna G C, Khanna N, O'Shea K M, Hecker P A, et al. (2010) Dietary supplementation with docosahexaenoic acid, but not eicosapentaenoic acid, dramatically alters cardiac mitochondrial phospholipid fatty acid composition and prevents permeability transition. Biochim Biophys Acta 1797: 1555-1562.

Belayev L, Khoutorova L, Atkins K D, Bazan N G (2009) Robust docosahexaenoic acid-mediated neuroprotection in a rat model of transient, focal cerebral ischemia. Stroke 40: 3121-3126.

Bazan N G (2012) Neuroinflammation and Proteostasis are Modulated by Endogenously Biosynthesized Neuroprotectin D1. Mol Neurobiol 46: 221-226.

Marcheselli V L, Hong S, Lukiw W J, Tian X H, Gronert K, et al. (2003) Novel docosanoids inhibit brain ischemia-reperfusion-mediated leukocyte infiltration and pro-inflammatory gene expression. J Biol Chem 278: 43807-43817.

Mukherjee P K, Marcheselli V L, Serhan C N, Bazan N G (2004) Neuroprotectin D1: a docosahexaenoic acid-derived docosatriene protects human retinal pigment epithelial cells from oxidative stress. Proc Natl Acad Sci USA 101: 8491-8496.

Belayev L, Khoutorova L, Atkins K D, Eady T N, Hong S, et al. (2011) Docosahexaenoic Acid Therapy of Experimental Ischemic Stroke. Transl Stroke Res 2: 33-41.

Terpstra A H (2001) Differences between humans and mice in efficacy of the body fat lowering effect of conjugated linoleic acid: role of metabolic rate. J Nutr 131: 2067-2068.

Blaxter K (1989) Energy metabolism in animals and man: Cambridge University Press, Cambridge, U K.

Miller A T (1986) Energy Metabolism. F.A. Davis Company, Philadelphia, Pa.

Lewandowski C, Barsan W (2001) Treatment of acute ischemic stroke. Ann Emerg Med 37: 202-216.

Blondeau N, Petrault O, Manta S, Giordanengo V, Gounon P, et al. (2007) Polyunsaturated fatty acids are cerebral vasodilators via the TREK-1 potassium channel. Circ Res 101: 176-184.

NINDS (1995) Tissue plasminogen activator for acute ischemic stroke. The National Institute of Neurological Disorders and Stroke rt-PA Stroke Study Group. N Engl J Med 333: 1581-1587.

NINDS (1997) Generalized efficacy of t-PA for acute stroke. Subgroup analysis of the NINDS t-PA Stroke Trial. Stroke 28: 2119-2125.

Dirnagl U, Iadecola C, Moskowitz M A (1999) Pathobiology of ischaemic stroke: an integrated view. Trends Neurosci 22: 391-397.

Ten V S, Starkov A (2012) Hypoxic-ischemic injury in the developing brain: the role of reactive oxygen species originating in mitochondria. Neurol Res Int 2012: 542976.

Williams J J, Deckelbaum R J, Mayurasakorn K, Ten V S (2011) n-3 Fatty acids protect brain against hypoxia-ischemia (HI) by attenuation of oxidative injury and mitochondrial dysfunction FASEB J 25: 105.104 (Abstract).

Lim S N, Huang W, Hall J C, Ward R E, Priestley J V, et al. (2010) The acute administration of eicosapentaenoic acid is neuroprotective after spinal cord compression injury in rats. Prostaglandins Leukot Essent Fatty Acids 83: 193-201.

Ward R E, Huang W, Curran O E, Priestley J V, Michael-Titus A T (2010) Docosahexaenoic acid prevents white matter damage after spinal cord injury. J Neurotrauma 27: 1769-1780.

King V R, Huang W L, Dyall S C, Curran O E, Priestley J V, et al. (2006) Omega-3 fatty acids improve recovery, whereas omega-6 fatty acids worsen outcome, after spinal cord injury in the adult rat. J Neurosci 26: 4672-4680.

What is claimed is:
1. A method comprising
 (a) providing an oil in water emulsion comprising
  (i) a perfusion buffer suitable for organ or tissue preservation and transplantation,
  (ii) 0.5% to 7% of an omega-3 oil by weight in grams per 100 ml of perfusion buffer, wherein the omega-3 oil comprises
   1) from about 10% to about 99% and omega-3 diglyceride, omega-3 triglyceride or combinations thereof by weight per total weight of the omega-3 oil, and at least about 20% to about 99% of the total acyl groups of the diglycerides and triglycerides comprise EPA, DHA, or combinations thereof, and
   2) less than 10% omega-6 fatty acids by weight per total weight of the omega-3 oil,
  (iii) less than 10% omega-6 oil by weight in grams per 100 ml of perfusion buffer, and

(iv) wherein the mean diameter of lipid droplets in the emulsion is from about 100 nm to less than about 5 microns, and (b) either perfusing or reperfusing an isolated organ or tissue ex vivo with the emulsion at a temperature of −5° C. to 37° C. for a duration of 1 hour to 72 hours to preserve the organ or tissue until it is transplanted into a recipient or is otherwise used.

2. The method of claim 1, wherein the organ and tissue is selected from the group comprising liver, lung, pancreas, skin, heart, heart valve, bone, bone marrow, blood vessels, lymph nodes, intestine, teeth, gingiva, small bowel, colon, appendages, scalp, epithelium or blood for transfusion.

3. The method of claim 1, wherein the organ is a heart, liver, kidney, pancreas, or lung.

4. A method for preserving or preparing an isolated organ or tissue for transplant, comprising either perfusing or reperfusing the organ or tissue ex vivo at a temperature of −5° C. to 37° C. for a duration of 1 hour to 72 hours until it is transplanted into a recipient or is otherwise used, with an omega 3 emulsion comprising (i) 0.5% to 7% of an omega-3 oil by weight in grams per 100 ml of perfusion buffer, wherein the omega-3 oil comprises 1. from about 10% to about 99% and omega-3 diglyceride, omega-3 triglyceride or combinations thereof by weight per total weight of the omega-3 oil, and at least about 20% to about 99% of the total acyl groups of the diglycerides and triglycerides comprise EPA, DHA, or combinations thereof, and 2. less than 10% omega-6 fatty acids by weight per total weight of the omega-3 oil, (ii) less than 10% omega-6 oil by weight in grams per 100 ml of perfusion buffer, and (iii) wherein the mean diameter of lipid droplets in the emulsion is from about 100 nm to less than about 5 microns.

5. The method of claim 1, wherein the duration of time is about 6 hours.

6. The method of claim 1, wherein the temperature is from −5° C. to 10° C.

7. The method of claim 1, wherein the temperature is 0° C. to 4° C.

8. The method of claim 1, wherein the temperature is 4° C. to 37° C.

* * * * *